United States Patent
Karp et al.

(10) Patent No.: US 10,041,046 B2
(45) Date of Patent: Aug. 7, 2018

(54) COMPOSITIONS AND METHODS FOR EPITHELIAL STEM CELL EXPANSION AND CULTURE

(71) Applicants: The Brigham and Women's Hospital, Inc., Boston, MA (US); Massachusetts Institute of Technology, Cambridge, MA (US)

(72) Inventors: Jeffrey Michael Karp, Brookline, MA (US); Xiaolei Yin, Quincy, MA (US); Marc David Succi, Boston, MA (US); Robert Samuel Langer, Newton, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/775,560

(22) PCT Filed: Mar. 11, 2014

(86) PCT No.: PCT/US2014/023197
§ 371 (c)(1),
(2) Date: Sep. 11, 2015

(87) PCT Pub. No.: WO2014/159356
PCT Pub. Date: Oct. 2, 2014

(65) Prior Publication Data
US 2016/0194604 A1 Jul. 7, 2016

Related U.S. Application Data

(60) Provisional application No. 61/783,245, filed on Mar. 14, 2013.

(51) Int. Cl.
*C12N 5/071* (2010.01)

(52) U.S. Cl.
CPC .......... *C12N 5/068* (2013.01); *C12N 5/0679* (2013.01); *C12N 2501/065* (2013.01); *C12N 2501/11* (2013.01); *C12N 2501/155* (2013.01); *C12N 2501/415* (2013.01); *C12N 2501/42* (2013.01); *C12N 2501/727* (2013.01); *C12N 2501/73* (2013.01); *C12N 2513/00* (2013.01)

(58) Field of Classification Search
CPC .......... C12N 2501/11; C12N 2501/155; C12N 2501/415; C12N 2501/42; C12N 5/068
See application file for complete search history.

(56) References Cited

U.S. PATENT DOCUMENTS

| | | |
|---|---|---|
| 5,059,591 A | 10/1991 | Janoff et al. |
| 5,421,818 A | 6/1995 | Arenberg |
| 5,474,529 A | 12/1995 | Arenberg |
| 5,476,446 A | 12/1995 | Arenberg |
| 5,731,144 A | 3/1998 | Toothman et al. |
| 5,731,424 A | 3/1998 | Toothman et al. |
| 5,837,681 A | 11/1998 | Magal |
| 6,045,528 A | 4/2000 | Arenberg et al. |
| 6,124,449 A | 6/2000 | Gold et al. |
| 6,090,383 A | 7/2000 | Dasch et al. |
| 6,177,434 B1 | 1/2001 | Kopke et al. |
| 6,419,928 B1 | 7/2002 | Dasch et al. |
| 6,476,031 B1 | 11/2002 | Chakravarty et al. |
| 6,509,318 B1 | 1/2003 | Bhatnagar et al. |
| 6,593,290 B1 | 7/2003 | Gao |
| 6,943,191 B1 | 9/2005 | Narayanan et al. |
| 7,030,125 B2 | 4/2006 | Munchhof et al. |
| 7,087,626 B2 | 8/2006 | Beight et al. |
| 7,151,169 B2 | 12/2006 | Thompson et al. |
| 7,223,766 B2 | 5/2007 | Dugar et al. |
| 7,387,614 B2 | 6/2008 | Staecker |
| 7,498,031 B2 | 3/2009 | Fujioka et al. |
| 7,514,445 B2 | 4/2009 | Freyne et al. |
| 7,723,486 B2 | 5/2010 | Ledbetter et al. |
| 8,071,591 B2 | 12/2011 | Nomura et al. |
| 8,207,216 B2 | 6/2012 | Kozikowski et al. |
| 8,298,825 B1 | 10/2012 | Hochedlinger et al. |

(Continued)

FOREIGN PATENT DOCUMENTS

| | | |
|---|---|---|
| CA | 2268331 A1 | 5/1998 |
| CN | 1319968 C | 10/2005 |

(Continued)

OTHER PUBLICATIONS

Itoh et al., False HDAC inhibition by aurone compound. Chemical and Pharmaceutical Bulletin, vol. 64 (2016) pp. 1124-1128.*
Brigande, J.V. and Heller, S., "Quo vadis, hair cell regeneration?" *Nat. Neurosci.*, 12(6): 679-685 (2009).
Chai, R., et al., "Dynamic Expression of Lgr5, a Wnt Target Gene, in the Developing and Mature Mouse Cochlea," *J Assoc. Res. Otolaryngology*, 12(4): 455-469 (2011).
Chai, R., et al., "Wnt signaling induces proliferation of sensory precursors in the postnatal mouse cochlea," *Proceedings Nat. Acad. Sci.*, 109(21): 8167-8172 (2012).
Chen, F-Q., et al., "Aminoglycoside-induced histone deacetylation and hair cell death in the mouse cochlea," *J. Neurochem.*, 108(5): 1226-1236 (2009).
Drottar, M., et al., "The Histone Deacetylase Inhibitor Sodium Butyrate Protects Against Cisplatin-Induced Hearing Loss in Guinea Pigs," *Laryngoscope*, 116(2): 292-296 (2006).

(Continued)

*Primary Examiner* — Kara Johnson
(74) *Attorney, Agent, or Firm* — Hamilton, Brook, Smith & Reynolds, P.C.

(57) ABSTRACT

Described are cell culture solutions and systems for epithelial stem cell and organoid cultures, formation of epithelial constructs and uses of the same in transplantation. A single layer of epithelial cells that actively self-renews and is organized into crypts and villi clothes the intestine. It has been recently shown that the renewal of intestinal epithelium is driven by Lgr5+ intestinal stem cells (ISC) that reside at the base of these crypts (Barker et al., 2007). Lgr5+ stem cells can be isolated and cultured in vitro to form organoids containing crypt-vellus structures that recapitulates the native intestinal epithelium (Sato et al., 2009).

19 Claims, 45 Drawing Sheets

(56) References Cited

U.S. PATENT DOCUMENTS

| | | | |
|---|---|---|---|
| 8,377,886 | B2 | 2/2013 | Susztak et al. |
| 8,575,122 | B2 | 11/2013 | Lichter et al. |
| 8,686,042 | B2 | 4/2014 | Gil et al. |
| 8,771,754 | B2 | 7/2014 | Hallahan |
| 9,347,042 | B2 | 5/2016 | Shimmura et al. |
| 2003/0028905 | A1 | 2/2003 | Knaus et al. |
| 2004/0006030 | A1 | 1/2004 | Monia et al. |
| 2004/0015781 | A1 | 1/2004 | Brown et al. |
| 2004/0038856 | A1 | 2/2004 | Chakravarty et al. |
| 2004/0138188 | A1 | 7/2004 | Higgins et al. |
| 2004/0147574 | A1 | 7/2004 | Munchhof |
| 2004/0204431 | A1 | 10/2004 | Scarborough et al. |
| 2005/0032835 | A1 | 2/2005 | Pandey et al. |
| 2005/0227936 | A1 | 10/2005 | McSwiggen et al. |
| 2005/0245508 | A1 | 11/2005 | Weller et al. |
| 2005/0245520 | A1 | 11/2005 | Dodic et al. |
| 2005/0287127 | A1 | 12/2005 | Li et al. |
| 2005/0287128 | A1 | 12/2005 | Guerciolini et al. |
| 2006/0003929 | A1 | 1/2006 | Bier et al. |
| 2006/0229266 | A1 | 10/2006 | Kumar et al. |
| 2007/0066632 | A1 | 3/2007 | Hart et al. |
| 2007/0088080 | A1 | 4/2007 | Gordillo et al. |
| 2007/0155722 | A1 | 7/2007 | Li et al. |
| 2007/0167918 | A1 | 7/2007 | Reed et al. |
| 2008/0015161 | A1 | 1/2008 | Vornlocher et al. |
| 2008/0108656 | A1 | 5/2008 | Pandey et al. |
| 2009/0036382 | A1 | 2/2009 | Bressan et al. |
| 2009/0270497 | A1 | 10/2009 | Buggy |
| 2010/0292205 | A1 | 11/2010 | Lefker et al. |
| 2011/0135756 | A1 | 6/2011 | Owens et al. |
| 2011/0166060 | A1 | 7/2011 | Simons et al. |
| 2011/0305674 | A1 | 12/2011 | Edge et al. |
| 2012/0196312 | A1 | 8/2012 | Sato et al. |
| 2013/0324594 | A1 | 12/2013 | Guthrie |
| 2017/0071937 | A1 | 3/2017 | Karp et al. |
| 2017/0226477 | A1 | 8/2017 | Karp et al. |
| 2017/0349884 | A1 | 12/2017 | Karp et al. |

FOREIGN PATENT DOCUMENTS

| | | |
|---|---|---|
| CN | 101341138 A | 1/2009 |
| CN | 103361300 A | 10/2013 |
| EP | 0945464 A1 | 9/1999 |
| EP | 1739087 A1 | 1/2007 |
| EP | 1961748 A2 | 8/2008 |
| EP | 2636731 A1 | 9/2013 |
| EP | 2765188 A1 | 8/2014 |
| WO | WO 96/40094 A1 | 12/1996 |
| WO | WO 98/19700 A1 | 5/1998 |
| WO | WO 99/58128 A1 | 11/1999 |
| WO | WO 00/12497 A2 | 3/2000 |
| WO | WO 00/31135 A1 | 6/2000 |
| WO | WO 00/59939 A1 | 10/2000 |
| WO | WO 01/85685 A1 | 11/2001 |
| WO | WO 02/094833 A1 | 11/2002 |
| WO | WO 03/037891 A1 | 5/2003 |
| WO | WO 03/097639 A1 | 11/2003 |
| WO | WO 2004/013135 A1 | 2/2004 |
| WO | WO 2004/021989 A2 | 3/2004 |
| WO | WO 2004/026307 A1 | 4/2004 |
| WO | WO 2004/026865 A1 | 4/2004 |
| WO | WO 2004/026871 A1 | 4/2004 |
| WO | WO 2004/067530 A1 | 8/2004 |
| WO | WO 2005/009939 A1 | 2/2005 |
| WO | WO 2005/039570 A1 | 5/2005 |
| WO | WO 2006/018633 A1 | 2/2006 |
| WO | WO 2006/018967 A1 | 2/2006 |
| WO | WO 2006/100490 A1 | 9/2006 |
| WO | WO 2007/018818 A1 | 2/2007 |
| WO | WO 2007/048857 A1 | 5/2007 |
| WO | WO 2007/102770 A1 | 9/2007 |
| WO | WO 2008/010852 A2 | 1/2008 |
| WO | WO 2008/076556 A2 | 6/2008 |
| WO | WO 2008/077138 A1 | 6/2008 |
| WO | WO 2009/017453 A1 | 2/2009 |
| WO | WO 2009/017455 A1 | 2/2009 |
| WO | WO 2009/032667 A1 | 3/2009 |
| WO | WO 2010/060088 A2 | 5/2010 |
| WO | WO 2010/068955 A2 | 6/2010 |
| WO | WO 2010/075551 A1 | 7/2010 |
| WO | WO 2010/104205 A1 | 9/2010 |
| WO | WO 2011/019957 A1 | 2/2011 |
| WO | WO 2011/079841 A1 | 7/2011 |
| WO | WO 2011/089416 A1 | 7/2011 |
| WO | WO 2011/116930 A1 | 9/2011 |
| WO | WO 2011/143511 A2 | 11/2011 |
| WO | WO 2012/103012 A1 | 8/2012 |
| WO | WO 2013/051722 A1 | 4/2013 |
| WO | WO 2013/124413 A1 | 8/2013 |
| WO | WO 2014/003098 A1 | 1/2014 |
| WO | WO 2014/013255 A1 | 1/2014 |
| WO | WO 2014/039908 A1 | 3/2014 |
| WO | WO 2014/050779 A1 | 4/2014 |
| WO | WO 2014/059383 A1 | 4/2014 |
| WO | WO 2014/083132 A1 | 6/2014 |
| WO | WO 2014/159356 A1 | 10/2014 |
| WO | WO 2015/168149 A2 | 11/2015 |
| WO | WO 2016/037016 A1 | 3/2016 |

OTHER PUBLICATIONS

Provenzano, M.J. and Domann, F.E., "A role for epigenetics in hearing: Establishment and maintenance of auditory specific gene expression patterns," *Hearing Res.*, 233(1-2): 1-13 (2007).

Yin, X., et al., "Niche-independent high-purity cultures of Lgr5+ intestinal stem cells and their progeny," *Nat. Methods*, 11(1): 106-112 (2014).

Fuller, M.K., et al., "Intestinal crypts reproducibly expand in culture", *J. Surg. Res.*, 178(1):48-54 (2012).

Haggarty, S.J., et al., "Domain-Selective Small-Molecule Inhibitor of Histone Deacetylase 6 (HDAC6)-Mediated Tubulin Deacetylation", *Proc. Nat'l. Acad. Sci. USA*, 100(8): 4389-4394 (2003).

Sekine, A., et al., "Hath1 Up-Regulates Gastric Mucin Gene Expression in Gastric Cells", *Biochem. Biophys. Res. Commun.*, 344(4): 1166-71 (2006).

van Es, J.H., et al., "Intestinal stem cells lacking the Math1 tumour suppressor are refractory to Notch inhibitors", *Nat. Commun.*, 1(18): 1-5 (2010).

Voytik-Harhin, S.L, et al,"Small Intestinal Submucosa: A Tissue-Derived Extracellular Matrix That Promotes Tissue-Specific Growth and Differentiation of Cells in Vitro", *Tissue Engineering*, 4(2). 157-174 (1998).

Written Opinion of the International Searching Authority for PCT/US2014/023197 "Compositions and Methods for Epithelial Stem Cell Expansion and Culture"; dated May 28, 2014.

International Search Report for PCT/US2014/023197 "Compositions and Methods for Epithelial Stem Cell Expansion and Culture"; dated May 28, 2014.

International Preliminary Report on Patentability for PCT/US2014/023197 "Compositions and Methods for Epithelial Stem Cell Expansion and Culture"; dated Sep. 15, 2015.

Barker, N., et al, "Identification of stem cells in small intestine and colon by marker gene Lgr5," *Nature*, 449: 1003-1007 (2007).

Buczacki, S.J., et al., "Intestinal label-retaining cells are secretory precursors expressing Lgr5," *Nature*, 495: 65-72 (2013).

Crosnier, C., et al., "Organizing cell renewal in the intestine: stem cells, signals and combinatorial control.," *Nature Reviews Genetics*, 7: 349-359 (2006).

Farin, H.F., et al., "Redundant sources of Wnt regulate intestinal stem cells and promote formation of Paneth cells," *Gastroenterology*, 143: 1518-1529 (2012).

Jung, P., et al., "Isolation and in vitro expansion of human colonic stem cells," *Nat. Med.*, 17, 1225-1227 (2011).

Kazanjian, A., et al., "Atonal homolog 1 is required for growth and differentiation effects of notch/gamma-secretase inhibitors on normal and cancerous intestinal epithelial cells," *Gastroenterology*, 139: 918-928 (2010).

(56) References Cited

OTHER PUBLICATIONS

Lukacs, R.U., et al., "Isolation, cultivation and characterization of adult murine prostate stem cells," *Nat. Protoc.*, 5(4):702-713 (2010).
Sato, T., et al., "Long-term expansion of epithelial organoids from human colon, adenoma, adenocarcinoma, and Barrett's epithelium," *Gastroenterology*, 141: 1762-1772 (2011).
Sato, T., et al., "Paneth cells constitute the niche for Lgr5 stem cells in intestinal crypts," *Nature*, 469: 415-418 (2011).
Scoville, et al., "Current view: intestinal stem cells and signaling," *Gastroenterology*, 134(3): 849-864 (2008).
Shi, F., et al., "Wnt-responsive Lgr5-expressing stem cells are hair cell progenitors in the cochlea," *J. Neurosci.*, 32(28): 9639-9648 (2012).
Snippert, H. J., et al., "Intestinal crypt homeostasis results from neutral competition between symmetrically dividing Lgr5 stem cells," *Cell*, 143: 134-144 (2010).
van der Flier, L.G., and Clevers, H., "Stem cells, self-renewal, and differentiation in the intestinal epithelium," *Annual Review of Physiology*, 71: 241-260 (2009).
van Es, J.H., et al., "Notch/gamma-secretase inhibition turns proliferative cells in intestinal crypts and adenomas into goblet cells," *Nature*, 435: 959-963 (2005).
VanDussen, K.L., et al., "Notch signaling modulates proliferation and differentiation of intestinal crypt base columnar stem cells," *Development*, 139: 488-497 (2012).
Yao, M., et al., "Prostate-regenerating capacity of cultured human adult prostate epithelial cells," *Cells Tissues Organs*, 191: 203-212 (2010).
Yilmaz, O.H., et al., "mTORC1 in the Paneth cell niche couples intestinal stem-cell function to calorie intake," *Nature*, 486: 490-495 (2012).
Ying, Q.L., et al., "The ground state of embryonic stem cell self-renewal," *Nature*, 453: 519-523 (2008).
Yui, S., et al., "Functional engraftment of colon epithelium expanded in vitro from a single adult Lgr5+ stem cell," *Nature Medicine*, 18(4): 618-623 (2012).
Zhang, F., et al., "Inhibitory Phosphorylation of Glycogens Synthase Kinase-3 (GSK-3) in Response to Lithium," *J. Bio. Chem.*, 278(3): 33067-33077 (2003).
Almeida, et al., "In Situ Gelling Systems: A Strategy to Improve the Bioavailability of Ophthalmic Pharmaceutical Formulations," Drug Discov. Today, 19(4):400-12, (Apr. 2014), (Epub Oct. 11, 2013).
Arnold, et al., "Zinc for Attention-Deficit/Hyperactivity Disorder: Placebo-Controlled Double-Blind Pilot Trial Alone and Combined with Amphetamine," Journal of Child and Adolescent Psychopharmacology, vol. 21(1):1-19 (Jan. 2011).
Bermingham, et al., "Math 1: An Essential Gene for the Generation of Inner Ear Hair Cells," Science, 284:1837-1841 (Jun. 11, 1999).
Bohl, et al., "Development of a Specially Tailored Local Drug Delivery System for the Prevention of Fibrosis After Insertion of Cochlear Implants Into the Inner Ear," Journal of Materials Science Materials in Medicine, vol. 23:2151-2162 (2012).
Byfield, et al., "Lateral Signaling Enhances TGF-β Response Complexity," Trends Cell Biol., 14(3):107-111 (Mar. 2004).
Chen,G. et al., "Preliminary Study on Brain-Targeted Drug Delivery Via Inner Ear," Yao xue xue bao = Acta pharmaceutica Sinica, 42:1102-1106 (2007).
Chen, et al., "Inner Ear Drug Delivery Via a Reciprocating Perfusion System in the Guinea Pig," Journal of Controlled Release : Official Journal of the Controlled Release Society, 110:1-19 (2005).
Fujioka, et al., "Development of Auditory-Specific Brain Rhythm in Infants," European Journal of Neuroscience, 33:521-529 (Jan. 13, 2011).
Gale, J. and Jagger, D., "Cochlear Supporting Cells," Chapter 11 in Oxford Handbook of Auditory Science: The Ear, 31 pages (2010).
Gupta, et al., "Fast-Gelling Injectable Blend of Hyaluronan and Methylcellulose for Intrathecal, Localized Delivery to the Injured Spinal Cord," Biomaterials, 27:2370-2379 (2006).

Harding, G.W. et al, "The effect of an age-related hearing loss gene (Ahl) on noise-induced hearing loss and cochlear damage from low-frequency noise," *Hearing Research*, 204:90-100 (2005).
Herraiz, et al., "Intratympanic Drug Delivery for the Treatment of Inner Ear Diseases," Acta Otorrinolaringologica Espanola, 61(3):225-232 (2010).
Hoskison, et al., "Drug Delivery to the Ear," Therapeutic Delivery, 4(1):115-124 (Jan. 2013).
Huang, et al., "Systematic and Integrative Analysis of Large Gene Lists Using DAVID Bioinformatics Resources," Nature Protocols, 4(1):44-57 (2009) (pub. online, Dec. 18, 2008).
Izumikawa, et al., "Auditory Hair Cell Replacement and Hearing Improvement by Atoh1 Gene Therapy in Deaf Mammals," Nat Med., 11(3):271-276 (Mar. 2005).
Kim, et al., "Development of a Drug Delivery System for the Inner Ear Using Poly(amino acid)-Based Nanoparticles," Drug Delivery, 22(3):367-374 (2015).
Lajud, S.A., et al., "A Regulated Delivery System for Inner Ear Drug Application," Journal of Controlled Release : Official Journal of the Controlled Release Society, 166:268-276 (2013).
Lehner, et al., "A Totally Implantable Drug Delivery System for Local Therapy of the Middle and Inner Ear," Ear, Nose, & Throat Journal, 76(8):567-570 (1997).
Li, et al., "A Novel Aerosol-Mediated Drug Delivery System for Inner Ear Therapy: Intratympanic Aerosol Methylprednisolone Can Attenuate Acoustic Trauma," IEEE Transactions on Bio-Medical Engineering, 60(9):2450-2460 (2013).
Lumpkin, et al., "Math1-Driven GFP Expression in the Developing Nervous System of Transgenic Mice," Gene Expr Patters, 3(4):389-395 (Aug. 2003).
Mills, D. M., "Determining the Cause of Hearing Loss: Differential Diagnosis Using a Comparison of Audiometric and Otoacoustic Emission Responses," Ear and Hearing, 27(5):508-525 (2006).
Mimura, T. et al., "Topical Ocular Drug Delivery to Inner Ear Disease and Sinusitis," Southern Medical Journal, 99(11):1287-1289 (2006).
Mundada, A.S. et al., "In Situ Gelling Polymers in Ocular Drug Delivery Systems: A Review," Critical Reviews in Therapeutic Drug Carrier Systems, 26(1):85-118 (2009). (Impact Factor-3.99).
Nakagawa, et al., "Local Drug Delivery to the Inner Ear Using Biodegradable Materials," Therapeutic Delivery, 2(6):807-814 (Jun. 2011).
Oshima, et al., "Phylogenetic Relationships Among Mycoplasmas Based on the Whole Genomic Information," J. Mol. Evol., 65(3):249-258 (Sep. 2007), (Epub Aug. 9, 2007).
Paasche, et al., "Technical Report: Modification of a Cochlear Implant Electrode for Drug Delivery to the Inner Ear," Otology & Neurotology, 24:222-227 (2003).
Pararas, et al., "Microsystems Technologies for Drug Delivery to the Inner Ear," Advanced Drug Delivery Reviews, 64:1650-1660 (2012).
Pararas, et al., "Kinetics of Reciprocating Drug Delivery to the Inner Ear," Journal of Controlled Release : Official Journal of the Controlled Release Society, 152:270-277 (2011).
Paulson, et al., "A Novel Controlled Local Drug Delivery System for Inner Ear Disease," Otology/Basic and Clinical Research; The Laryngoscope, vol. 118:706-711 (2008).
Peer, et al., "Nanocarriers as an Emerging Platform for Cancer Therapy," Nature Nanotechnology, 2:751-760 (2007).
Plontke, et al. "Randomized Double Blind, Placebo Controlled Trial on the Safety and Efficacy of Continuous Intratympanic Dexamethasone Delivered Via a Round Window Catheter for Severe to Profound Sudden Idiopathic Sensorineural Hearing Loss After Failure of Systemic Therapy," The Laryngoscope, 119:359-369 (2009).
Plontke, et al., "Technical Note on Microcatheter Implantation for Local Inner Ear Drug Delivery: Surgical Technique and Safety Aspects," Otology & Neurotology, 27(7):912-917 (2006).
Plontke, S. K., "Evaluation of the Round Window Niche Before Local Drug Delivery to the Inner Ear Using a New Mini-Otoscope," Otology & Neurotology, 32(1):183-185 (2011).

(56) References Cited

OTHER PUBLICATIONS

Plontke, et al., "Pharmacokinetic Considerations in Intratympanic Drug Delivery to the Inner Ear," Acta Oto-Rhino-Laryngologica Belgica, 56(4):369-370 (2002).
Plontke, et al., "Transtympanic Endoscopy for Drug Delivery to the Inner Ear Using a New Microendoscope," Advances in Oto-Rhino-Laryngology, 59:149-155 (2002).
Pritz, et al., "Nanomedicine Strategies for Drug Delivery to the Ear," Nanomedicine, 8(7):1155-1172 (Jul. 2013).
Purow, B., "Notch Inhibition as a Promising New Approach to Cancer Therapy," Advances in Experimental Medicine and Biology, 727:305-319 (2012).
Raphael, Y., "Evidence for Supporting Cell Mitosis in Response to Acoustic Trauma in the Avian Inner Ear," Journal of Neurocytology, 21:663-671 (1992).
Richardson, et al., "Novel Drug Delivery Systems for Inner Ear Protection and Regeneration After Hearing Loss," Expert Opinion on Drug Delivery, 5(10):1059-1076 (Sep. 2008).
Rivera, et al., "Drug Delivery to the Inner Ear: Strategies and their Therapeutic Implications for Sensorineural Hearing Loss," Current Drug Delivery, 9(3):231-242 (May 2012).
Roy, et al., "Strategies for Drug Delivery to the Human Inner Ear by Multifunctional Nanoparticles," Nanomedicine, 7(1):55-63 (2012).
Roy, et al., "Cell-Specific Targeting in the Mouse Inner Ear Using Nanoparticles Conjugated with a Neurotrophin-Derived Peptide Ligand: Potential Tool for Drug Delivery," International Journal of Pharmaceutics, 390:214-224 (2010).
Ryals, et al., "Return of Function After Hair Cell Regeneration," Hearing Research, 297:113-120 (2013).
Sakamoto, T. et al., "Inner Ear Drug Delivery System from the Clinical Point of View," Acta Oto-Laryngologica, 130:sup563:101-104 (2010).
Salt, et al., "Dependence of Hearing Changes on the Dose of Intratympanically Applied Gentamicin: A Meta-Analysis Using Mathematical Simulations of Clinical Drug Delivery Protocols," The Laryngoscope, 118(10):1793-1800 (Oct. 2008).
Salt, A., "Guest Editorial: Drug Delivery for Treatment of Inner Ear Disease: Current State of Knowledge," Ear and Hearing, vol. 31, p. 155 (2010).
Sataloff, R. T. et al., "Differential Diagnosis of Occupational Hearing Loss," Occupational Health & Safety, 70(9):126-129 (Sep. 2001).
Staecker, et al., "Drug Delivery to the Inner Ear Using Gene Therapy," Otolaryngologic Clinics of North America, vol. 37, pp. 1091-1108, 2004.
Staecker, et al., "Developments in Delivery of Medications for Inner Ear Disease," Expert Opinion on Drug Delivery, 10(5):639-650 (2013).
Surovtseva, et al., "Prestin Binding Peptides as Ligands for Targeted Polymersome Mediated Drug Delivery to Outer Hair Cells in the Inner Ear," International Journal of Pharmaceutics, 424:121-127 (2012).
Van Tomme, S.R. et al., "In Situ Gelling Hydrogels for Pharmaceutical and Biomedical Applications," Int. J. Pharm., 355(1-2):1-18 (2008).
Wang, Y.et al., "Dynamics of Noise-Induced Cellular Injury and Repair in the Mouse Cochlea," J. of the Assoc. of Research in Otolaryngology, 3:248-268 (2002).
Wise, A.K. et al, "Drug Delivery to the Inner Ear," Journal of Neural Engineering, 9(6):065002, 10 pages (Nov. 2012).
Wu, et al., "Modulation of Notch Signaling by Mastermind-Like (MAML) Transcriptional Co-Activators and Their Involvement in Tumorigenesis," Seminars in Cancer Biology, 14:348-356 (2004).
Yang, J. et al, "Functional Features of Trans-Differentiated Hair Cells Mediated by Atoh 1 Reveals a Primordial Mechanism," J. of Neuroscience, 32(11):3712-3725 (Mar. 2012).
Yang, J. et al, "Ectopic Hair Cell-Like Cell Induction by Math 1 Mainly Involves Direct Transdifferentiation in Neonatal Mammalian Cochlea," Neuroscience Letters, 549:7-11 (2013).
Zheng, et al., "Overexpresson of Math 1 Induces Robust Production of Extra Hair Cells in Postnatal Rat Inner Ears," Nature Neuroscience, 3(6):580-586 (Jun. 2000).
Alford, et al., "American College of Medical Genetics and Genomics Guideline for the Clinical Evaluation and Etiologic Diagnosis of Hearing Loss," Genetics in Medicine: Official Journal of the American College of Medical Genetics, vol. 16, pp. 347-355, 2014.
Barker, et al., "Lgr5$^{+ve}$ stem cells drive self-renewal in the stomach and build long-lived gastric units in vitro," Cell Stem Cell, vol. 6, 25-36, 2010.
Borenstein, J. T., "Intracochlear Drug Delivery Systems," Expert Opinion on Drug Delivery, vol. 8, No. 9, pp. 1161-1174, Sep. 2011, published online May 26, 2011.
Bramhall, N. F. et al., "Lgr5-Positive Supporting Cells Generate New Hair Cells in the Postnatal Cochlea", Stem Cell Reports, 2(3): 311-322 (2014).
Byfield, et al., "SB-505124 Is a Selective Inhibitor of Transforming Growth Factor-β Type I Receptors ALK4, ALK5, and ALK7," Molecular Pharmacology, vol. 65, No. 3, pp. 744-752, Mar. 2004.
Callahan, et al., "Identification of Novel Inhibitors of the Transforming Growth Factor Betal (TGF-beta1) Type 1 Receptor (ALK5)," J. Med. Chem., vol. 45., No. 5, pp. 999-1001, Feb. 28, 2002.
Cox, et al., "Spontaneous Hair Cell Regeneration in the Neonatal Mouse Cochlea in Vivo," Development, vol. 141, No. 4, pp. 816-829, Feb. 2014.
Dai, et al., "Human Serum and Glucocorticoid-Inducible Kinase-Like Kinase (SGKL) Phosphorylates Glycogen Syntheses Kinase 3 Beta (GSK-3beta) at Serine-9 Through Direct Interation," Biolchem. Biophys. Res. Commun., vol. 293, No. 4, pp. 1191-1196, May 17, 2002.
Davies, et al., "The Interaction Between β-Catenin, GSK3β and APC After Motogen Induced Cell-Cell Dissociation, and Their Involvement in Signal Transduction Pathways in Prostate Cancer," International Journal of Oncology, vol. 18, No. 4, pp. 843-847, Apr. 1, 2001.
Davis, et al, "Mesodermal Fate Decisions of a Stem Cell: the Wnt Switch," Cell Mol Life Sci., 65(17):2658-74 (2008) (abstract only).
Dumont, et al., "Targeting the TGFβ Signaling Network in Human Neoplasia," Cancer Cell, vol. 3, No. 6, pp. 531-536, Jun. 2003.
Engleder, et al., "Preclinical Evaluation of Thermoreversible Triamcinolone Acetonide Hydrogels for Drug Delivery to the Inner Ear," International Journal of Pharmaceutics, vol. 471, No. 1-2, pp. 297-302, Aug. 25, 2014.
Espinoza, et al., "Phosphorylation by Glycogen Synthase Kinase-3β Down-Regulates Notch Activity, a Link for Notch and Wnt Pathways," Journal of Biological Chemistry, vol. 278, No. 34, pp. 32227-32235, Aug. 22, 2003.
Foltz, et al., "Glycogen Synthase Kinase-3β Modulates Notch Signaling and Stability," Current Biology, vol. 12, No. 12, pp. 1006-1011, Jun. 25, 2002.
Fu, et al., "SM16, an Orally Active TFG-β Type I Receptor Inhibitor Prevents Myofibroblast Induction and Vascular Fibrosis in the Rat Carotid Injury Model," Arteriosclerosis, Thrombosis and Vascular Biology, vol. 28, No. 4, pp. 665-671, Jan. 17, 2008.
Garcia-Berrocal Jr., et al., "Alternatives to Systemic Steroid Therapy for Refractory Immune-Mediated Inner Ear Disease: A Physiopathologic Approach," Eur. Arch. Otorhinolarynqol, vol. 263, No. 11, pp. 977-982, Nov. 2006.
Gellibert, et al., "Identification of 1, 5-Naphthyridine Derivatives as a Novel Series of Potent and Selective TGF-Beta Type 1 Receptor Inhibitors," J. Med. Chem., vol. 47, No. 18, pp. 4494-4506, Aug. 26, 2004.
Haegebarth, et al., "Wnt Signaling, Lgr5, and Stem Cells in the Intestine and Skin," The American Jounral of Pathology, vol. 174, No. 3, pp. 715-721, Mar. 2009.
Halder, et al., "A Specific Inhibitor of TGF-β Receptor Kinase, SB-431542, As a Potent Antitumor Agent for Human Cancers," Neoplasia, vol. 7, No. 5, pp. 509-521, May 2005.
Hong, et al., "Human Dynamin-Like Protein Interacts with the Glycogen Synthase Kinase 3β," Biochem. Biophys. Res. Commun., vol. 249, No. 3, pp. 697-703, Aug. 28, 1998.

(56) References Cited

OTHER PUBLICATIONS

Huang, et al., "Directed, Efficient, and Versatile Modifications of the *Drosophila* Genome by Genomic Engineering," PNAS, vol. 106, No. 20, pp. 8284-9290, May 19, 2009.

Huang, et al., "RAD18 Transmits DNA Damage Signaling to Elicit Homologous Recombination Repair," Nat. Cell. Biol., vol. 11, No. 5, pp. 592-603, May 2009.

Isaacson, et al., "Differential Diagnosis and Treatment of Hearing Loss," American Family Physician, vol. 18, pp. 1125-1132, 2003.

Jeon, et al., "Notch Signaling Alters Sensory or Neuronal Cell Fate Specification of Inner Ear Stem Cells," Journal Neurosci, vol. 31, No. 23, pp. 8351-8358, Jun. 8, 2011.

Kanzaki, et al., "Novel in Vivo Imaging Analysis of an Inner Ear Drug Delivery System in Mice: Comparison of Inner Ear Drug Concentrations Over Time After Transtympanic and Systemic Injections," PloS One, vol. 7:e48480, 2012.

Kawamoto, Tadafumi, "Use of a New Adhesive Film for the Preparation of Multi-Purpose Fresh-Frozen Sections from Hard Tissues, Whole-Animals, Insects and Plants," Arch Histol Cytol, vol. 66, No. 2, pp. 123-143, Apr. 2003.

Koch, et al., "Stem cells living with a Notch," The Company of Biologists Ltd, Development, vol. 140, pp. 689-704, 2013.

Kujawa, et al., "Conditioning-Related Protection from Acoustic Injury: Effects of Chronic Deefferentation and Sham Surgery," J. Neurophysiol., vol. 78, pp. 3095-3106 (1997).

Lanford, et al., "Notch Signaling Pathway Mediates Hair Cell Development in Mammalian Cochlea,"Nature Genetics, vol. 21, pp. 289-292, Mar. 1999.

Lasak, et al., "Hearing Loss: Diagnosis and Management," Primary Care, vol. 41, pp. 19-31, 2014.

Li, et al., "Interaction of Glycogen Synthase Kinase 3β with the DF3/MUC1 Carcinoma-Associated Antigen and β-Catenin," Molecular and Cellular Biology, vol. 18, No. 12, pp. 7216-7224, Dec. 1998.

Li, et al., "Retinoic Acid Stimulates Chondrocyte Differentiation and Enhances Bone Morphogenetic Protein Effects through Induction of Smad1 and Smad5," Endocrinology, vol. 144, No. 6, pp. 2514-2523, Feb. 3, 2003.

Liu, et al. "Identification of Stage-Specific Markers During Differentiation of Hair Cells From Mouse Inner Ear Stem Cells or Progenitor Cells in Vitro," Int. J. Biochem. Cell. Biol., vol. 60, pp. 99-111, Mar. 2015.

Liu, et al., "In vivo Notch reactivation in differentiating cochlear hair cells induces Sox2 and Prox1 expression but does not disrupt hair cell maturation," Dev Dyn., vol. 241, pp. 684-696, Apr. 2012.

Lu, Z., et al., "The Influence of Glycogen Synthase Kinase 3 in Limiting Cell Addition in the Mammalian Ear," pp. 1059-1075, published online in Wiley InterScience (www.interscience.wiley.com) May 9, 2008.

Maison, et al., "Olivocochlear Innervation in the Mouse: Immunocytochemical Maps, Crossed Versus Uncrossed Contributions, and Transmitter Colocalization," J. Comp. Neurol., vol. 455, No. 3, pp. 406-416, Jan. 13, 2003.

Mak, et al., "The Tuberin-Hamartin Complex Negatively Regulates β-Catenin Signaling Activity," The Journal of Biological Chemistry, vol. 278, No. 8, 5947-5951, Feb. 2003.

Martinez-Monedero, et al., "Differentiation of Inner Ear Stem Cells to Functional Sensory Neurons," Developmental Neurobiology, vol. 68, No. 5, pp. 669-684, Apr. 2008.

McCall, et al., "Drug Delivery for Treatment of Inner Ear Disease: Current State of Knowledge," Ear and Hearing, vol. 31, No. 2, pp. 156-165, Apr. 2010.

Meng, et al., "Gamma-Secretase Inhibitors Abrogate Oxaliplatin-Induced Activation of the Notch-1 Signaling Pathway in Colon Cancer Cells Resulting in Enhanced Chemosensitivity," Cancer Research, vol. 69, pp. 573-582, 2009.

Mikulec, et al., "Permeability of the Round Window Membrane is Influenced by the Composition of Applied Drug Solutions and by Common Surgical Procedures," Otol. Neurotol. vol. 29, No. 7, pp. 1020-1026, Oct. 2008.

Mizutari, et al., "Notch Inhibition Induces Cochlear Hair Cell Regeneration and Recovery of Hearing after Acoustic Trauma," Neuron, vol. 77, No. 1, pp. 58-69, Jan. 2013.

Mizutari, et al., "Spontaneous Recovery of Cochlear Fibrocytes After Severe Degeneration Caused by Acute Energy Failure," Frontiers in Pharmacology, vol. 5, No. 198, pp. 1-3, Aug. 26, 2014.

Nakamura, et al., "Axin, An Inhibitor of the Wnt Signalling Pathway, Interacts with β-Catenin, GSK-3β and APC and Reduces the β-Catenin Level," Genes Cells, vol. 3, No. 6, pp. 395-403, Jun. 1998.

Olsauskas-Kuprys, et al., "Gamma Secretase Inhibitors of Notch Signaling," OncoTargets and Therapy, vol. 6, pp. 943-955, 2013.

Peterson, et al., "Oral Administration of GW788388, An Inhibitor of TGF-β Type I and II Receptor Kinases, Decreases Renal Fibrosis," Kidney International, vol. 73, pp. 705-715, (2008), published online Dec. 12, 2007.

Plontke, et al., "1D-and 3D-Computer Simulation for Experimental Planning and Interpretation of Pharmacokinetic Studies in the Inner Ear After Local Drug Delivery," Altex, vol. 21, Suppl 3, pp. 77-85, 2004.

Plontke, et al., "Cochlear Pharmacokinetics With Local Inner Ear Drug Delivery Using a Three-Dimensional Finite-Element Computer Model," Audiology & Neuro-Otology, vol. 12, pp. 37-48, 2007.

Plontke, et al., "Simulation of Application Strategies for Local Drug Delivery to the Inner Ear," ORL Journal for Oto-Rhino-Laryngology and Its Related Specialties, vol. 68, No. 6, pp. 386-392, Oct. 26, 2006.

Sage, et al., "Essential role of retinoblastoma protein in mammalian hair cell development and hearing," Proc. Natl. Acad. Sci. USA, vol. 103, pp. 7345-7350, May 2006.

Sage, et al., "Proliferation of Functional Hair Cells in Vivo in the Absence of the Retinoblastoma Protein," Science, vol. 307, pp. 1114-1118, Feb. 18, 2005.

Salt, et al., "Distribution of Dexamethasone and Preservation of Inner Ear Function Following Intratympanic Delivery of a Gel-Based Formulation," Audiology & Neuro-otology, vol. 16, pp. 323-335, 2011.

Salt, et al., "Local Inner Ear Drug Delivery and Pharmacokinetics," Drug. Discov. Today, vol. 10, No. 19, pp. 1299-1306, Oct. 1, 2005.

Salt, et al., "Principles of Local Drug Delivery to the Inner Ear," Audiol. Neurotol. vol. 14, No. 6, pp. 350-360, Nov. 16, 2009.

Salvi, et al., "Hair Cell Regeneration, Repair, and Protection," Springer Handbook of Auditory Research, Vols. 1-33, 323 pages, 2008.

Sawyer, et al., "Synthesis and Activity of New Aryl- and Heteroaryl-Substituted 5, 6-Dihiydro-4H-Pyrrolo[1,2-b]Pyrazole Inhibitors of the Transforming Growth Factor-Beta Type I Receptor Kinase Domain," Bioorg. Med. Chem. Lett., vol. 14, No. 13, pp. 3581-3584, Jul. 5, 2004.

Sawyer, et al., "Synthesis and Activity of New Aryl-and Heteroaryl-Substituted Pyrazole Inhibitors of the Transforming Growth Factor-Beta Type 1 Receptor Kinase Domain," J. Med. Chem., vol. 46, No. 19, pp. 3953-3956, Sep. 11, 2003.

Schwarz-Romond, et al., "The Ankyrin Repeat Protein Diversin Recruits Casein Kinase Iε to the β-Catenin Degradation Complex and Acts in Both Canonical Wnt and Wnt/JNK Signaling," Genes, Dev., vol. 16, No. 16, pp. 2073-2084, Jun. 2002.

Seidman, M. D., "Glutamate Antagonists, Steroids, and Antioxidants as Therapeutic Options for Hearing Loss and Tinnitus and the Use of an Inner Ear Drug Delivery System," The International Tinnitus Journal, vol. 4, pp. 148-154, 1998.

Shariatmadari, M., et al., "Increased Wnt Levels in the Neural Tube Impair the Function of Adherens Junctions During Neurulation," Mol Cell Neurosci.,30(3): 437-51. Epub (2005) (abstract only).

Shi, et al., "Beta-Catenin Up-Regulates Atoh1 Expression in Neural Progenitor Cells by Interaction with an Atoh1 3' Enhancer," The Journal of Biological Chemistry, vol. 285, pp. 392-400, 2010.

Shi, et al., "Generation of Hair Cells in Neonatal Mice by β-Catenin Overexpression in Lgr5-Positive Cochlear Progenitors," Proc Natl Acad Sci USA, vol. 110, No. 34, pp. 13851-13856, Aug. 20, 2013.

Shih, et al., "Notch Signaling, Gamma-Secretase Inhibitors, and Cancer Therapy," Cancer Research, vol. 67, pp. 1879-1882, 2007.

(56) References Cited

OTHER PUBLICATIONS

Swan, et al., "Inner Ear Drug Delivery for Auditory Applications," Adv. Drug. Deliv. Rev., vol. 60, No. 15, pp. 1583-1599, Dec. 14, 2008.
Tojo, et al., "The ALK-5 Inhibitor A-83-01 Inhibits Smad Signaling and Epithelial-to-Mesenchymal Transition by Transforming Growth Factor-β," Cancer Sci., vol. 96, No. 11, pp. 791-800, Nov. 2005.
Valdimarsdottir, et al., "Functions of the TGFβ Superfamily in Human Embryonic StempCells,"APMIS, vol. 113, pp. 773-389, Nov.-Dec. 2005.
Von Kries, et al., "Hot Spots in Beta-Catenin for Interactions with LEF-1, Conductin and APC," Nat. Struct. Biol., vol. 7, No. 9, pp. 800-807, Sep. 2000.
Wang, et al., "Suppression of Androgen Receptor-Mediated Transactivation and Cell Growth by the Glycogen Synthase Kinase 3β in Prostate Cells," Journal of Biological Chemistry, vol. 279, No. 31, pp. 32444-32452, Jul. 30, 2004.
Warchol, et al., "Regenerative Proliferation in Organ Cultures of the Avian Cochlea: Identification of the Initial Progenitors and Determination of the Latency of the Proliferative Response," The Journal of Neuroscience : the Official Journal of the Society for Neuroscience, vol. 16, pp. 5466-5477, 1996.
White, et al., "Mammalian Cochlear Supporting Cells Can Divide and Trans-Differentiate Into Hair Cells," Nature, vol. 441, No. 7096, pp. 984-987, Jun. 22, 2006.
Wong, et al., "Mechanisms of sensorineural cell damage, death and survival in the cochlea," Frontiers in Aging Neuroscience, vol. 7, Article 58, pp. 1-15, Apr. 2015.
Yingling, et al., "Development of TGF-β Signalling Inhibitors for Cancer Therapy," Nature Reviews Drug Discovery, vol. 3, No. 12, pp. 1011-1022, Dec. 2004.
Yu, et al., "In vivo proliferation of postmitotic cochlear supporting cells by acute ablation of the retinoblastoma protein in neonatal mice," J Neurosci, vol. 30, pp. 5927-5936, Apr. 2010.
Yuge, I., et al., "Transplanted Human Amniotic Epithelial Cells Express Connexin 26 and Na-K-Adenosine Triphophatase in the Inner Ear," Transplantation, vol. 77, No. 9, pp. 1452-1454, 2004.
Zahnert, T., "The Differential Diagnosis of Hearing Loss," Deutsches Arzteblatt International, vol. 108, pp. 433-443, quiz 44, 2011.
Associação Brasileira de Otorrinolaringologia e Cirurgia Cérvico-facial et al., "Sensorineural Hearing Loss: Radiologic Diagnosis," Revista da Associacao Medica Brasileira, vol. 58, pp. 519-529, 2012.
Butler et al., "Rational Design and Simple Chemistry Yield a Superior, Neuroprotective HDAC Inhibitor, Tubastatin A," J. Am. Chem. Soc., vol. 132: 10842-10846 (2010).
Salt, A.; "Dexamethasone Concentration Gradients Along Scala Tympani After Application to the Round Window Membrane," Otology & Neurotology, 29(3):401-406 (2008).
Shoichet, M.S. et al., "Intrathecal Drug Delivery Strategy is Safe and Efficacious for Localized Delivery to the Spinal Cord," Progress in Brain Research, 161:385-392 (2007).

\* cited by examiner

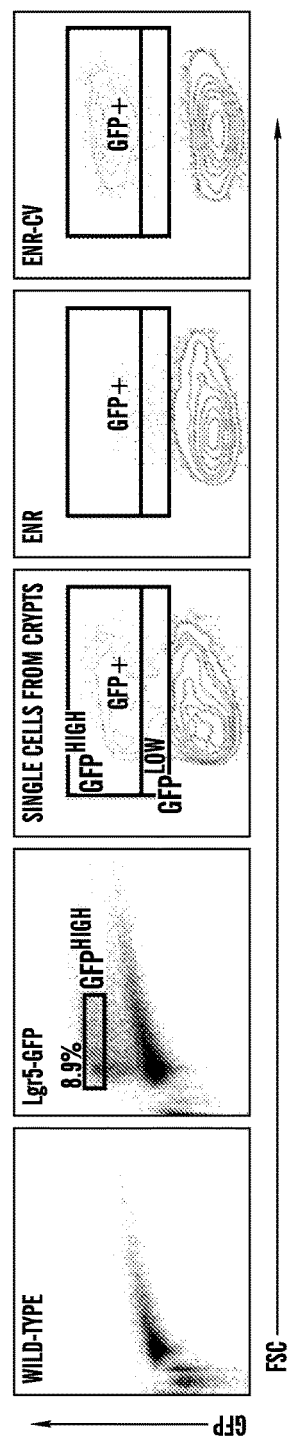
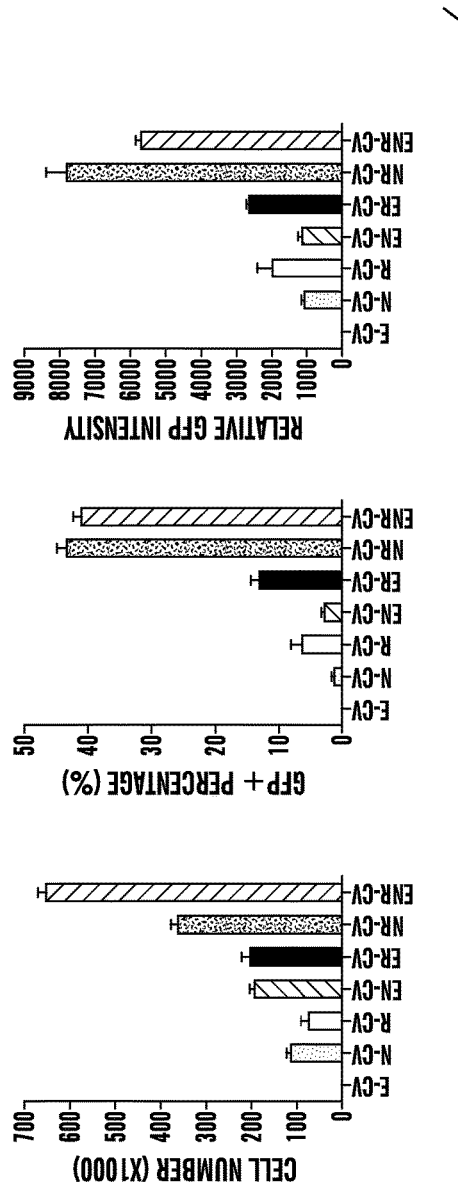
FIG. 3C
FIG. 3D

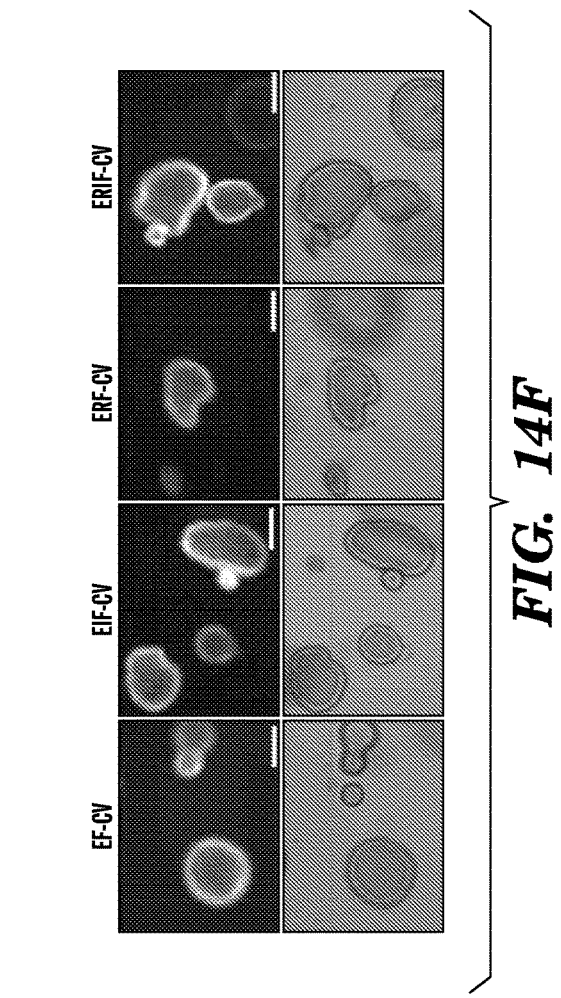
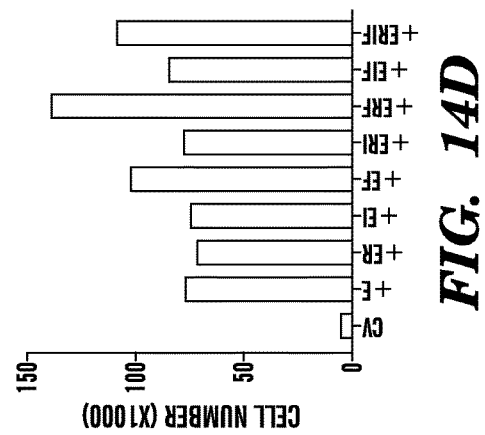
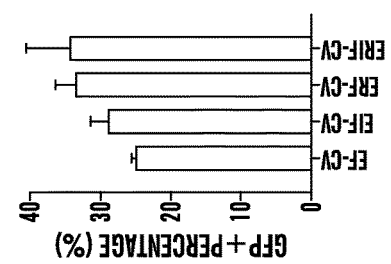
FIG. 14D
FIG. 14E
FIG. 14F

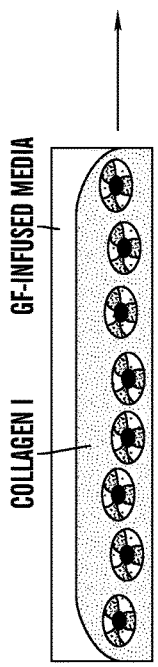 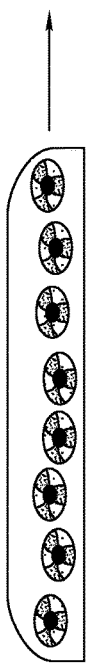  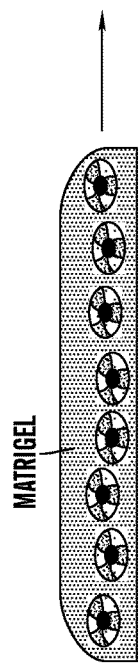
FIG. 19G    FIG. 19I    FIG. 19K    FIG. 19M
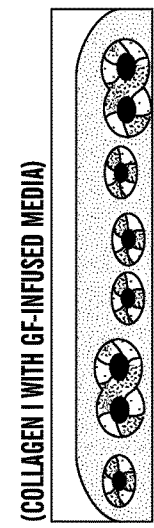  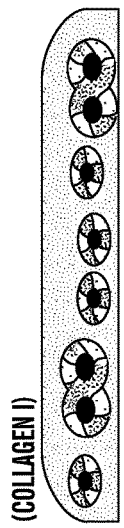 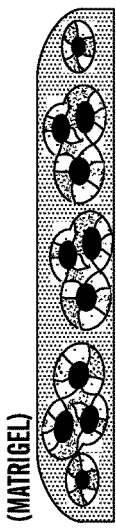
FIG. 19H    FIG. 19J    FIG. 19L    FIG. 19N

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence

```
<220> FEATURE:
<223> OTHER INFORMATION: FRATtide peptide

<400> SEQUENCE: 1

Ser Gln Pro Glu Thr Arg Thr Gly Asp Asp Asp Pro His Arg Leu Leu
1               5                   10                  15

Gln Gln Leu Val Leu Ser Gly Asn Leu Ile Lys Glu Ala Val Arg Arg
            20                  25                  30

Leu His Ser Arg Arg Leu Gln
            35
```

COMPOSITIONS AND METHODS FOR EPITHELIAL STEM CELL EXPANSION AND CULTURE

CROSS-REFERENCE TO RELATED APPLICATIONS

This application is the U.S. National Stage of International Application No. PCT/US2014/023197, filed Mar. 11, 2014, which designates the U.S., published in English, and claims benefit under 35 U.S.C. § 119(e) of U.S. Provisional Application No. 61/783,245, filed Mar. 14, 2013, the contents of which are incorporated herein by reference in its entirety.

GOVERNMENT SUPPORT

This invention was made with Government support under Grant No. R01 DE013023 awarded by the National Institutes of Health. The Government has certain rights to the invention.

INCORPORATION BY REFERENCE OF MATERIAL IN ASCII TEXT FILE

This application incorporates by reference the Sequence Listing contained in the following ASCII text file:
 a) File name: 00502283002_SEQLIST; created Mar. 22, 2016, 39 kb in size.

BACKGROUND OF THE INVENTION

A single layer of epithelial cells that actively self-renews and is organized into crypts and villi clothes the intestine. It has been recently shown that the renewal of intestinal epithelium is driven by Lgr5$^+$ intestinal stem cells (ISC) that reside at the base of these crypts (Barker et al., 2007). Lgr5$^+$ stem cells can be isolated and cultured in vitro to form organoids containing crypt-villus structures that recapitulates the native intestinal epithelium (Sato et al., 2009). While these stem cells can be expanded for multiple passages in the form of organoids, existing culture conditions provide little to no control over self-renewal and differentiation. Typical cultures consist of heterogeneous cell populations, including stem cells and differentiated cells (Sato et al., 2009). In particular, the self-renewal and proliferation of Lgr5$^+$ stem cells both in vitro and in vivo are dependent on direct cell contact between Lgr5$^+$ stem cells and another crypt cell type known as paneth cells (Snippert et al., 2010), which significantly complicates and limits the ability to control the fate of Lgr5$^+$ stem cells in culture. The inability to efficiently expand Lgr5$^+$ stem cells considerably limits the translation of this biology to therapies, where homogeneous stem cell cultures and efficient scale-up processes are essential prior to transplantation. Moreover, there remains a need to develop improved, clinically-oriented systems for transplantation of ex vivo expanded epithelial tissue into injured recipient organs.

SUMMARY OF THE INVENTION

In one aspect, the invention provides cell culture solutions.

In one embodiment, the invention provides a cell culture solution comprising an inhibitor of a Bone Morphogenic Protein, an inhibitor of Glycogen synthase kinase-3 beta, an agent that binds to the Leucine-rich repeat-containing G-protein coupled receptor 5 and a histone deacetylase inhibitor. In one embodiment, the inhibitor of Glycogen synthase kinase-3 beta can be CHIR99021, the agent that binds to the Leucine-rich repeat-containing G-protein coupled receptor 5 can be R-spondin 1, and the HDAC inhibitor can be Valproic acid.

In another embodiment, the invention provides a cell culture solution comprising an inhibitor of a Bone Morphogenic Protein, at least about 3 uM CHIR99021 and a histone deacetylase inhibitor.

In yet another embodiment, the invention provides a cell culture solution comprising an inhibitor of a Bone Morphogenic Protein, an agent that binds to the Leucine-rich repeat-containing G-protein coupled receptor 5, a Wnt agonist and a HDAC6 inhibitor.

In yet another embodiment, the invention provides a cell culture solution comprising an inhibitor of a Bone Morphogenic Protein, R-spondin 1, lithium chloride and a histone deacetylase inhibitor.

In yet another embodiment, the invention provides a histone deacetylase inhibitor that is a Pan-HDAC inhibitor. The Pan-HDAC inhibitor can be selected from the group consisting of Valproic acid, Trichostatin A, suberoylanilide hydroxamic acid and Suberohydroxamic acid (SBHA).

In yet another embodiment, the invention provides a histone deacetylase inhibitor that is an HDAC6 inhibitor. The HDAC6 inhibitor can be selected from the group consisting of Tubacin, Tubastatin A and Compound 7.

In yet another embodiment, the invention provides an inhibitor of a Bone Morphogenic Protein that can be selected from the group consisting of Noggin, Chordin, Follistatin, DAN, proteins comprising a DAN cysteine-knot domain, Sclerostin, Twisted Gastrulation, Uterine Sensitivity-Associated Gene-1, Connective-Tissue Growth Factor, Inhibin, BMP-3 and Dorsomorphin.

In yet another embodiment, the invention provides an inhibitor of Glycogen synthase kinase-3 beta that can be selected from the group consisting of CHIR99021, LiCl, BIO-acetoxime, CHIR98014, SB 216763, SB 415286, 3F8, Kenpaullone, 1-Azakenpaullone, TC-G 24, TCS 2002, AR-A014418, TCS 21311, TWS 119, BIO-acetoxime, 10Z-Hymenialdisine, GSK-3β Inhibitor II, GSK-3β Inhibitor I, GSK-3β Inhibitor XXVII, GSK-3β Inhibitor XXVI, FRATtide peptide, Cdk1/5 Inhibitor and Bikinin.

In yet another embodiment, the invention provides an agent that binds to the Leucine-rich repeat-containing G-protein coupled receptor 5 that can be selected from the group consisting of R-spondin 1, R-spondin 2, R-spondin 3 and R-spondin 4.

In yet another embodiment, the invention provides a Wnt agonist that can be selected from the group consisting of: Wnt-1/Int-1, Wnt-2/Irp (Int-I-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, Wnt-16, R-spondin 1, R-spondin 2, R-spondin 3, R-spondin 4, Norrin, CHIR99021, LiCl, BIO ((2'Z,3'E)-6-Bromoindirubin-3'-oxime), CHIR98014, SB 216763, SB 415286, 3F8, Kenpaullone, 1-Azakenpaullone, TC-G 24, TCS 2002, AR-A014418, 2-amino-4-[3,4-(methylenedioxy)benzyl-amino]-6-(3-methoxyphenyl)pyrimidine, IQ 1, DCA, QS 11, WAY-316606, (hetero)arylpyrimidines, 10Z-Hymenialdisine, TCS 21311, TWS 119, GSK-3 Inhibitor IX, GSK-3 Inhibitor IV, GSK-3β Inhibitor II, GSK-3β Inhibitor I, GSK-3β Inhibitor XXVII, GSK-3beta Inhibitor XXVI, FRATtide, Cdk1/5 Inhibitor, Bikinin, and 1-Azakenpaullone.

In yet another embodiment, the invention provides a cell culture solution comprising Noggin, R-spondin 1, CHIR99021 and an Atoh1 inhibitor. The Atoh1 inhibitor can be an inhibitory nucleic acid.

In yet another embodiment, the invention provides a cell culture solution further comprising an Epidermal Growth Factor and/or a Notch agonist. The Notch agonist can be selected from the group consisting of a Notch1 antibody (N1 Ab), Delta 1, Delta-like 3, Delta-like 4, Jagged 1, Jagged 2, DSL peptide and Delta D.

In yet another embodiment, the invention provides between about 5 to about 500 ng/ml EGF, about 5 to about 500 ng/ml Noggin, about 50 to about 1000 ng/ml R-spondin, about 0.1 to about 10 µM CHIR99021 and about 0.1 to about 5 mM Valproic acid.

In yet another aspect, the invention provides cell culture systems comprising cell culture solutions of the invention.

In one embodiment, the invention provides a cell culture system comprising:
  i) an epithelial stem cell or epithelial progenitor cell or a population of epithelial stem cells or epithelial progenitor cells;
  ii) R-spondin 1;
  iii) CHIR99021;
  iv) a histone deacetylase inhibitor; and
  v) optionally an inhibitor of a Bone Morphogenic Protein.

In another embodiment, the invention provides a cell culture system comprising:
  i) an epithelial stem cell or epithelial progenitor cell or a population of epithelial stem cells or epithelial progenitor cells;
  ii) R-spondin 1;
  iii) CHIR99021;
  iv) an Atoh1 inhibitor; and
  v) optionally an inhibitor of a Bone Morphogenic Protein.

In yet another embodiment, the invention provides a cell culture system comprising:
  i) an epithelial stem cell or epithelial progenitor cell or a population of epithelial stem cells or epithelial progenitor cells;
  ii) R-spondin 1;
  iii) lithium chloride;
  iv) a histone deacetylase inhibitor; and
  v) optionally an inhibitor of a Bone Morphogenic Protein.

In yet another embodiment, the invention provides a cell culture system comprising:
  i) an epithelial stem cell or epithelial progenitor cell or a population of epithelial stem cells or epithelial progenitor cells;
  ii) R-spondin 1;
  iii) a Wnt Agonist;
  iv) a HDAC6 inhibitor; and
  v) optionally an inhibitor of a Bone Morphogenic Protein.

In yet another embodiment, cell culture systems of the invention comprise epithelial stem cells and populations of epithelial stem cells that can comprise LGR5 positive stem cells.

In yet another embodiment, the population of epithelial stem cells or epithelial progenitor cells in the cell culture system the invention comprises at least 30%, 85%, 90%, 95% or 99% of the cells in the system.

In yet another embodiment, the invention provides a cell culture system comprising:
  i) a tumor organoid;
  ii) an agent that binds to the Leucine-rich repeat-containing G-protein coupled receptor 5;
  iii) a Wnt Agonist;
  iv) a histone deacetylase inhibitor or an Atoh1 inhibitor; and
  v) optionally an inhibitor of a Bone Morphogenic Protein.

In yet another embodiment, the invention provides a cell culture system comprising a submucosa base, a coating layer comprising collagen and a cell layer comprising any member of the group consisting of epithelial stem cells, an isolated tissue comprising epithelial stem cells, and/or epithelial organoids. The coating comprising collagen can be on top of, or surrounding, the epithelial stem cells, isolated tissue comprising epithelial stem cells, or epithelial organoids. The coating comprising collagen can also be between the SIS base and the epithelial stem cells, isolated tissue comprising epithelial stem cells, or epithelial organoids. The submucosa base can comprise SIS and can further comprise an Epidermal Growth Factor, a Bone Morphogenic Protein, an agent that binds to the Leucine-rich repeat-containing G-protein coupled receptor 5, a Wnt Agonist, Y-27632 and a histone deacetylase inhibitor. This cell culture system can further comprise cell culture solutions of the invention, including a solution comprising an inhibitor of a Bone Morphogenic Protein, an agent that binds to the Leucine-rich repeat-containing G-protein coupled receptor 5, a Wnt Agonist, Y-2763 and a histone deacetylase inhibitor.

In yet another embodiment, the invention provides a cell culture system comprising a submucosa base and epithelial stem cells, isolated tissue comprising epithelial stem cells, or epithelial organoids, wherein the submucosa base comprises an Epidermal Growth Factor, a Bone Morphogenic Protein, R-spondin 1, CHIR99021, Y-27632 and a histone deacetylase inhibitor. This cell culture system can further comprise a solution comprising an Epidermal Growth Factor, an inhibitor of a Bone Morphogenic Protein, R-spondin 1, CHIR99021, Y-27632 and a histone deacetylase inhibitor.

In yet another aspect, the invention provides methods of forming epithelial organoids from isolated epithelial stem cells.

In one embodiment, the invention provides a method of forming epithelial organoids from isolated epithelial stem cells with high efficiency, said method comprising the steps of:
  i) incubating isolated epithelial stem cells in the presence of Noggin, R-spondin 1, CHIR99021 and a histone deacetylase inhibitor; and
  ii) forming epithelial organoids from said isolated epithelial stem cells, wherein at least about 25%, 40%, 50%, 75%, 90%, of the isolated epithelial stem cells form epithelial organoids.

In another embodiment, the invention provides a method of forming epithelial organoids from a single isolated epithelial stem cell with high efficiency, said method comprising the steps of:
  i) incubating said single isolated epithelial stem cell in the presence of Noggin, R-spondin 1, CHIR99021 and a histone deacetylase inhibitor; and
  ii) forming epithelial organoids from said isolated epithelial stem cell, wherein at least about 6% of the single isolated epithelial stem cells form epithelial organoids.

In yet another aspect, the invention provides a method of determining the efficacy of a chemotherapeutic agent relative to a tumor organoid, said method comprising the steps of:
  i) incubating a tumor organoid in the presence of an inhibitor of a Bone Morphogenic Protein, R-spondin 1, a Wnt agonist, a histone deacetylase inhibitor and a chemotherapeutic agent; and ii) measuring a parameter selected from the group consisting of inhibition of cell viability, inhibition of cell proliferation, inhibition of tumor associated gene expression, activation of apoptosis and inhibition of cell survival, wherein detecting an increase in the parameter indicates efficacy of the chemotherapeutic agent relative to a tumor organoid.

In yet another aspect, the invention provides a method of forming a paneth cell in a cell culture system comprising incubating an epithelial stem cell in the presence of at least one Wnt agonist and at least one inhibitor of Notch, each in an amount sufficient to produce a paneth cell.

In one embodiment, the epithelial stem cell can be further be incubated in the presence of at least one inhibitor of a Bone Morphogenic Protein.

In another embodiment, the inhibitor of Notch is DAPT.

In yet another embodiment, the epithelial stem cell is an LGR5 positive stem cell.

In yet another aspect, the invention provides a method of forming an enterocyte in a cell culture system comprising incubating an epithelial stem cell in the presence of at least one Wnt inhibitor and at least one histone deacetylase inhibitor, each in an amount sufficient to produce an enterocyte in a cell culture system. The epithelial stem cell can be further incubated in the presence of an Epidermal Growth Factor and/or an inhibitor of a Bone Morphogenic Protein.

In one embodiment, the Wnt inhibitor can be selected from the group consisting of IWP-2, XAV-939, ICG-001, LGK-974, IWR-1-endo, KY02111, Wnt-059, DKK-1, FH-535, Box5, Peptide Pen-N3, Anti-SFRP antibody, and Anti-LRP6 antibody.

In yet another aspect, the invention provides a method of forming a goblet cell in a cell culture system comprising incubating an epithelial stem cell in the presence of at least one Wnt inhibitor and at least one Notch inhibitor, each in an amount sufficient to produce a goblet cell in a cell culture system. The epithelial stem cell can be further incubated in the presence of an Epidermal Growth Factor.

In one embodiment, the Notch inhibitor can be selected from the group consisting of DAPT, RO4929097, LY450139, LY900009, LY3039478, LY411575, YO-01027, BMS-708163, BMS-906024, Compound E, BMS-299897, SAHM1, Abeta42-Selective and SB 225002.

In yet another aspect, the invention provides a method of forming an enteroendocrine cell in a culture system comprising incubating an epithelial stem cell in the presence of at least one inhibitor of Notch and an agent that inhibits at least one of a Receptor Tyrosine Kinase, a Mitogen-activated protein (MAP) kinase or an Extracellular signal-regulated kinase (ERK), each in an amount sufficient to produce an enteroendocrine cell in a cell culture system. The epithelial stem cell can be further incubated in the presence of an Epidermal Growth Factor, an agent that binds to the Leucine-rich repeat-containing G-protein coupled receptor 5 and/or an inhibitor of a Bone Morphogenic Protein. The MAP kinase can be Mitogen-activated protein kinase kinase (MEK).

In one embodiment, the agent that inhibits the MAP kinase can be selected from the group consisting of AS-703026, PD0325901, PD98059, Selumetinib, SL-327, U0126, TAK-733 and Trametinib.

In another embodiment, the agent that inhibits an RTK can be selected from the group consisting of Gefitinib, AG 99, Erlotinib, Afatinib, Lapatinib, WZ4002 and AG-18.

In yet another embodiment, the agent that inhibits an ERK can be AS-703026 or PD0325901.

In yet another aspect, the invention provides a method of forming intestinal epithelial cells in a subject in need thereof, comprising administering to the subject a Wnt agonist and a histone deacetylase inhibitor in an amount sufficient to form intestinal epithelial cells in the subject. The Wnt agonist can be CHIR99021 and the histone deacetylase inhibitor can be Valproic acid. The CHIR99021 can be administered in an amount of about 0.1 mg/kg/day to about 100 mg/kg/day and the Valproic acid can be administered in an amount of about 1 mg/kg/day to about 1000 mg/kg/day.

In yet another aspect, the invention provides a method of forming intestinal epithelial cells in a subject in need thereof, comprising administering to the subject a Wnt agonist and a Notch agonist in an amount sufficient to form intestinal epithelial cells in the subject.

In yet another aspect, the invention provides a method of treating an intestinal disorder, the method comprising administering to the subject a Wnt agonist and a histone deacetylase inhibitor or a Wnt agonist and a Notch agonist. In some embodiments, the intestinal disorder is selected from the group consisting of: enterocolitis; viral infections, such as non-specific enteritis or specific viral enteritis; diverticulitis; bacterial enterocolitis, such as *salmonellosis*, shigellosis, *campylobacter* enterocolitis, or yersinia enterocolitis; protozoan infections such as amebiasis; helminthic infection; and pseudomembraneous colitis and pulmonary complications in cystic fibrosis and chronic obstructive pulmonary disease; appendicitis; atrophic gastritis; Barrett's esophagus; pneumonitis; cervicitis; chronic interstitial nephritis; colitis; colonic diverticulitis; conjunctivitis; contact dermatitis; Curling's ulcers; Cushing's ulcers; cystitis; gangrene; gingivitis; mastitis; esophagitis; pancreatitis; panniculitis; phlegmonous gastritis; glomerulonephritis; and autoimmune diseases including, but not limited to, inflammatory bowel disease, ulcerative colitis, Crohn's disease, Addison's disease and glomerulonephritis (e.g., crescentic glomerulonephritis, proliferative glomerulonephritis).

Other features and advantages of the invention will be apparent from the following detailed description and figures, and from the claims.

BRIEF DESCRIPTION OF THE DRAWINGS

The following Detailed Description, given by way of example, but not intended to limit the invention to specific embodiments described, may be understood in conjunction with the accompanying figures, incorporated herein by reference.

FIG. 2A depicts GFP and bright field images of small intestinal crypts cultured for 6 days in the presence of ENR (EGF, Noggin and R-spondin1), ENR+VPA (ENR-V), ENR+CHIR (ENR-C) and ENR+VPA+CHIR (ENR-CV). Apoptotic cells are visible in the lumen with autofluorescence (red arrows), and white arrows indicate specific Lgr5-GFP at the base of crypts. Scale Bar: 100 µm. FIG. 2B depicts quantification of cell proliferation and GFP expression of crypts cultured in multiple conditions. Crypts were cultured in 24 well plates for 6 days and dissociated into single cells using Accutase. Live cell numbers in each well were counted as an indicator of cell proliferation. Lgr5-GFP expression was measured by flow cytometry analysis. Error bars indicate S.D. of triplicate wells. Experiments were performed 3 times and showed similar results. FIGS. 2C and 2D depict flow cytometry analysis of GFP expression of single Lgr5-GFP cells after 7 days of culture under multiple conditions as indicated. Error bars indicate S.D. of triplicate wells. FIG. 2E depicts GFP and brightfield images of single Lgr5-GFP cells following 9 days of culture. Scale Bar: 100 µm. FIG. 2F depicts representative images of 4,000 FACS isolated single Lgr5-GFP cells cultured under multiple conditions for 7 days and FIG. 2G depicts quantification of colony numbers. Error bars indicate S.D. of triplicate wells. FIG. 2H depicts the metaphase spread of a cell cultured in the CV condition for 80 days having a normal karyotype (2n=40). (Unless otherwise indicated, in all panels: *P<0.001; P<0.01; *P<0.05; NS P>0.05.)

FIGS. 3A-3G depict cell growth and GFP expression as a function of culture conditions. FIGS. 3A and 3B depict colony numbers and live single cell numbers, respectively, from triplicate wells enumerated at each time point. Error bars indicate S.D. In FIG. 3A, the series are, from left to right, Day 0, Day 2, Day 4, Day 6, Day 8, and Day 10. FIG. 3C depicts FACS sorting of freshly isolated single Lgr5-GFP+ cells. A GFP$^{high}$ single cell population was collected. Representative FACS analysis and the gating strategy to define the GFP+ cell population is shown. Freshly isolated single cells from crypts showed two discriminated GFP$^{high}$ and GFP$^{low}$ populations while cultured cells did not show discriminated GFP$^{high}$ and GFP$^{low}$ populations, so all GFP+ cells were gated for analysis. Note that the ENR-CV cultured cells showed a single GFP+ population that was GFP highly positive. The GFP-population represents Lgr5- cells as well as Lgr5+/GFP– cells (i.e. GFP silenced stem cells), which is present in all unsorted crypt cultures, but not in sorted single Lgr5-GFP cell cultures (See FIG. 2C). A total of 10,000 live cells were analyzed for each sample. FIG. 3D depicts growth factor requirements for self-renewal of Lgr5+ stem cells in the CV culture condition. Crypts were cultured for 6 days in the presence of CHIR and VPA, with EGF, Noggin, R-spondin 1 and their combinations, as indicated. E: EGF (50 ng/ml); N: Noggin (100 ng/ml); R: R-spondin 1 (500 ng/ml); C: CHIR (3 µM); V: VPA (1 mM). FIG. 3E depicts crypts cultured for 6 days in multiple conditions as indicated. GFP and brightfield images are shown. Scale bars: 200 µm. FIG. 3F depicts morphology and Lgr5-GFP expression of colon crypts cultured in ENR, ENR-C and ENR-CV conditions. FIG. 3G depicts isolated number of organoids formed at day 5 in the presence of EGF, Noggin and R-spondin 1 or R-spondin 2 at multiple concentrations. All scale bars: 200 µm.

FIG. 4B depicts quantification of cell proliferation and GFP expression of crypts cultured under multiple conditions. Crypts were cultured for 6 days in 24-well plates and dissociated into single cells. Live cell numbers in each well were counted and the percentage of GFP+ cells was analyzed by flow cytometry. Error bars indicate S.D. of triplicate wells.

FIG. 5A depicts single isolated Lgr5-GFP+ cells cultured for 9 days in CV condition. Scale bars: 200 µm. FIG. 5B depicts 1500 FACS sorted single Lgr5+ cells cultured in Matrigel under conditions as indicated. Representative images from day 7 cultures are shown. FIG. 5C indicates quantification of colony numbers. Error bars indicate S.D. or triplicate wells. FIG. 5D shows sorted single Lgr5+ stem cells seeded in 48-well plates. Viable cell numbers were quantified at 12 hours after plating. Colony numbers were counted at day 7 and colony-forming efficiency was quantified. V: VPA; C: CHIR; W: Wnt3a at 100 ng/ml. Error bars indicate S.D. of 3 triplicate wells. Experiments were performed 3× and showed similar results.

In FIGS. 6B and 6C, only crypt domains contain Ki67 positive cells or incorporate EdU in the ENR condition (Upper panels) while Ki67 or EdU is present throughout the cell aggregates in the CV condition (Lower panels). FIG. 6D depicts quantitative real-time PCR analysis of relative mRNA expression of markers for mature intestinal epithelial cells cultured for 6 days under conditions as indicated (Intestinal Alkaline phosphatase [Alpi] for enterocytes, Mucin 2 [Muc2] for goblet cells, Chromogranin A [ChgA] for enteroendocrine cells, Lysozyme [Lyz] for Paneth cells, and Lgr5 for intestinal stem cells). ENR-CV (D40) indicates cells that were cultured in the CV condition for 40 days. Scale bars: 50 µm. In FIG. 6D, the series are, from left to right, Alpi, Muc2, ChgA, Lyz, and Lgr5.

FIG. 7A depicts staining of differentiation markers (Alp for enterocytes, Muc2 for goblet cells (white arrows) and mucin secreted by goblet cells, ChgA for enteroendocrine cells and Lyz for Paneth cells) of cells transferred from CV condition to ENR condition and cultured for 4 days. DAPI was used to stain nuclei and GFP indicates the presence of stem cells. FIG. 7B shows real-time RT-PCR analysis of relative mRNA expression of mature intestinal epithelial markers from cells cultured under multiple conditions. Cells were initially cultured from single cells in the CV condition for 6 days. Cell colonies were then harvested, washed and re-plated into several wells of 24 well plates and cultured for 4 days in Matrigel under multiple conditions as indicated. ENR was added in all conditions and the cells cultured with ENR alone were used as controls. I: IWP-2 (2 µM), D: DAPT (10 µM), C: CHIR (3 µM), V: VPA (1 mM). Error bars indicate S.D. FIG. 7C depicts Alp staining of cells cultured under multiple conditions. There is a clear morphology change of cells in the ID and CD conditions, which resembles goblet cells and Paneth cells. Scale bars: 50 µm. FIG. 7D depicts immunocytochemistry staining of differentiation markers. Cells cultured under CD and ID conditions were used for Mucin 2 (Muc2), Chromogranin A (ChgA) and Lysozyme (Lyz) staining Three dimensional reconstructed confocal images are shown. Scale bars: 50 µm.

FIG. 8A depicts staining of organoids cultured in ENR condition. The left panel depicts Alp staining of enterocytes. Prior to staining, the organoid was cut open under a dissecting microscope by using a sharp blade and the luminal content was removed. The middle panel depicts Muc2 staining of goblet cells (arrows) as well as mucin secreted by goblet cells, and the right panel depicts ChgA staining of enteroendocrine cells. GFP+ cells indicate Lgr5+ stem cells. FIG. 8B provides a scheme of the differentiation protocol. Single Lgr5+ stem cells were cultured in the CV condition for 4-6 days to form colonies. Cell colonies were then harvested, washed, embedded within fresh Matrigel and cultured under multiple conditions. FIG. 8C depicts morphology of cell colonies transferred from the CV condition to the ENR condition and cultured for 4 days (upper panels). Colonies continuously cultured in the CV condition are shown as a control (lower panels). FIG. 8D depicts morphology of differentiated cells with low and high magnification images for each condition. Note the clear change in morphology for most cells in the CD and ID conditions, which reflects formation of Paneth cells and goblet cells, respectively. FIG. 8E depicts Alp staining of colonies cultured in IV condition. Apical (left panel) and homogeneous (right panel) staining of Alp are shown. FIG. 8F depicts Muc2 staining of colonies cultured in ID and CD conditions. All scale bars: 50 µm.

FIG. 9A depicts morphology and Lgr5-GFP expression of crypts cultured in multiple conditions for 6 days. C: CHIR (3 µM); Li: LiCl (5 mM); W: Wnt3a (100 nM). FIG. 9B depicts cell numbers and percentage of GFP+ cells for 6 day crypt cultures. The data is representative of three independent experiments. FIG. 9C shows 6 day cultures of crypts in ENR-C(Control) condition or together with HDAC inhibitors. FIG. 9D depicts quantification of GFP percentage, total live cell number and relative GFP intensity of cells in FIG. 9C. FIG. 9E depicts the effects of VPA and TSA on cell proliferation and GFP expression at multiple concentrations. FIG. 9F depicts the effects of nicotinamide (Ni) in combination with Wnt3a (W, 100 ng/ml) or CHIR (C, 3 µM). Shown are cell numbers and percentage of GFP+ cells of crypts cultured for 6 days in multiple conditions. (Unless otherwise indicated, in all panels: Error bars indicate S.D. or triplicate wells. *$P<0.001$; $P<0.01$; *$P<0.05$; NS $P>0.05$.)

FIG. 11A depicts VPA rescuing GFP expression following Notch inhibition. Crypts were cultured in ENR-C condition with or without DAPT (D, 5 µM) and varying concentration of VPA (V, 0.25-4 mM) for 3 days. Scale bars: 200 µm. FIGS. 11B and 11C depict crypts cultured in the ENR (FIG. 11B) or ENR+CHIR (FIG. 11C) conditions for 4 days followed by addition of VPA at different concentrations for another 24 hours. The expression of Notch1, Hes1 and Atoh1 were analyzed by Real-time RT-PCR. FIG. 11D depicts analysis of Notch1, Hes1 and Atoh1 expression by Real-time RT-PCR in crypts after 6 days of culture. In FIG. 11B-11C, the series are, from left to right, 0, 0.5, 1, 2, and 3. In FIG. 11D, the series are, from left to right, ENR, ENR-V, ENR-C, and ENR-CV.

FIG. 13A depicts brightfield and GFP images of isolated cochlea sensory epithelium derived from an Lgr5-GFP mouse at post natal day 2. FIG. 13B depicts isolated cochlea sensory epithelium dissociated into single cells and cultured in multiple conditions for 11 days. E: EGF; N: Noggin; R: R-spondin 1; C: CHIR99021, V: VPA. Scale bars: 100 µm.

FIGS. 14A-14F depict the combination of CHIR and VPA promoting the proliferation and GFP expression of Lgr5+ stem/progenitor cells from the mouse inner ear. FIG. 14A depicts GFP expression of inner ear epithelial cells. FIG. 14B depicts quantification of GFP expression and cell number. FIG. 14C depicts brightfield and GFP images. FIG. 14D depicts cell number of 8 day cultures of inner ear stem cells in multiple conditions as indicated. FIG. 14E depicts GFP percentage of 8 day cultures of inner ear stem cells in multiple conditions as indicated. FIG. 14F depicts morphology and GFP expression of Lgr5-GFP inner ear stem cells cultured in multiple conditions. All scale bars: 200 µm.

FIGS. 19A-19N depict a schematic of seeding (left) and post-incubation organoid growth (right) in culture systems evaluated. FIGS. 19A and 19B depict a typical submucosal seeding method (herein referred to as "bare patch"), which supports monolayer growth and organoid dissociation. FIG. 19E, inset, depicts each organoid individually encased in a soft gel as well as SIS base layer. FIGS. 19G and 19H depict typical collagen suspension with GFs (EGF, Noggin, R-spondin 1, Y-27632, Valproic Acid, CHIR) added directly to culture media. FIGS. 19I and 19J depict typical collagen suspension with GFs (EGF, Noggin, R-spondin 1, Y-27632, Valproic Acid, CHIR) embedded in the gel. FIGS. 19K and 19L depict typical collagen suspension without additional GFs added to culture media. FIGS. 19M and 19N depict typical Matrigel suspension without additional GFs added to media (experimental control).

FIG. 25A depicts proliferation of human intestinal epithelial cells cultured in multiple conditions. Freshly isolated human small intestinal crypts were cultured in multiple conditions as indicated. EGF, Noggin, R-spondin1 were present in all conditions. Cell numbers were quantified at day 9 after seeding. C: CHIR, V: VPA, used at 0.5-1.5 mM, Ni: Nicotinamide. FIG. 25B depicts LGR5 expression of cells cultured in multiple conditions as in FIG. 15A. VPA was used at 1 mM.

DETAILED DESCRIPTION OF THE INVENTION

Definitions

Figure 1:
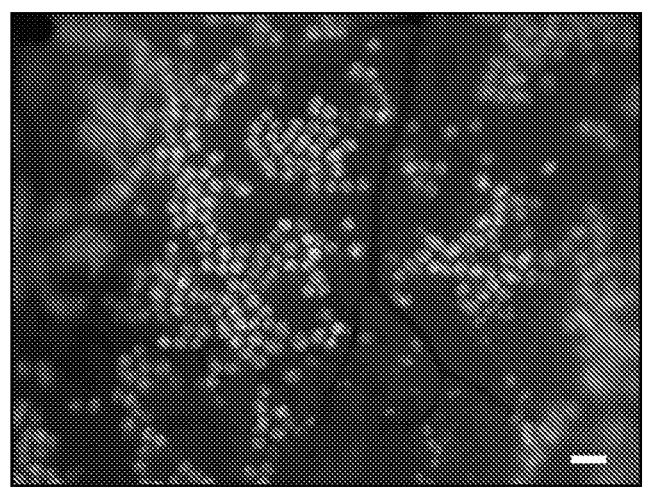
FIG. 1 depicts scattered expression of Lgr5-GFP in vivo. Small intestine was harvested from Lgr5-GFP mice and directly imaged under fluorescence microscopy. While all areas of the small intestine were covered by crypts, approximately half of these crypts contained GFP+ cells. Scale bar: 100 µm.

As used herein, an "antibody" is any immunoglobulin polypeptide, or fragment thereof, having immunogen binding ability.

As used herein, an "agonist" is an agent that causes an increase in the expression or activity of a target gene or protein, respectively. An agonist can bind to and activate its cognate receptor in some fashion, which directly or indirectly brings about this physiological effect on the target gene or protein.

As used herein, an "inhibitor" is an agent that causes a decrease in the expression or activity of a target gene or protein, respectively. An "antagonist" can be an inhibitor, but is more specifically an agent that binds to a receptor, and which in turn decreases or eliminates binding by other molecules.

As used herein, an "inhibitory nucleic acid" is a double-stranded RNA, siRNA, shRNA, or antisense RNA, or a portion thereof, or a mimetic thereof, that when administered to a mammalian cell results in a decrease in the expression of a target gene. Typically, a nucleic acid inhibitor comprises at least a portion of a target nucleic acid molecule, or an ortholog thereof, or comprises at least a portion of the complementary strand of a target nucleic acid molecule. Typically, expression of a target gene is reduced by 10%, 25%, 50%, 75%, or even 90-100%.

By "anti-sense" is meant a nucleic acid sequence, regardless of length, that is complementary to the coding strand or mRNA of a nucleic acid sequence. As referred to herein, a "complementary nucleic acid sequence" is a nucleic acid sequence capable of hybridizing with another nucleic acid sequence comprised of complementary nucleotide base pairs. By "hybridize" is meant pair to form a double-stranded molecule between complementary nucleotide bases (e.g., adenine (A) forms a base pair with thymine (T), as does guanine (G) with cytosine (C) in DNA) under suitable conditions of stringency. (See, e.g., Wahl, G. M. and S. L. Berger (1987) Methods Enzymol. 152:399; Kimmel, A. R. (1987) Methods Enzymol. 152:507). In one embodiment, an antisense RNA is introduced to an individual cell, tissue or organanoid. The anti-sense nucleic acid may contain a modified backbone, for example, phosphorothioate, phosphorodithioate, or other modified backbones known in the art, or may contain non-natural internucleoside linkages.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or culture system. Such siRNAs are used to downregulate mRNA levels or promoter activity.

As used herein, a "fragment" is a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids As used herein, the term "stem cell" refers to a multipotent cell having the capacity to self-renew and to differentiate into multiple cell lineages.

As used herein, the term "epithelial stem cell" refers to a multipotent cell which has the potential to become committed to multiple cell lineages, including cell lineages resulting in epithelial cells.

As used herein, the term "progenitor cell" refers to a lineage-restricted cell derived from a stem cell.

As used herein, the term "epithelial progenitor cell" refers to a multipotent cell which has the potential to become restricted to cell lineages resulting in epithelial cells.

As used herein, the term "self-renewal" refers to the process by which a stem cell divides to generate one (asymmetric division) or two (symmetric division) daughter cells with development potentials that are indistinguishable from those of the mother cell. Self-renewal involves both proliferation and the maintenance of an undifferentiated state.

As used herein, the term "engraft" or "engraftment" refers to the process of stem or progenitor cell incorporation into a tissue of interest in vivo through contact with existing cells of the tissue.

As used herein, the term "isolated" refers to a material that is free to varying degrees from components which normally accompany it as found in its native state. "Isolate" denotes a degree of separation from original source or surroundings.

As used herein, a "population" of cells is any number of cells greater than 1, but is preferably at least $1 \times 10^3$ cells, at least $1 \times 10^4$ cells, at least at least $1 \times 10^5$ cells, at least $1 \times 10^6$ cells, at least $1 \times 10^7$ cells, at least $1 \times 10^8$ cells, at least $1 \times 10^9$ cells, or at least $1 \times 10^{10}$ cells.

As used herein, the term "organoid" or "epithelial organoid" refers to a cell cluster or aggregate that resembles an organ, or part of an organ, and possesses cell types relevant to that particular organ.

As used herein, a "subject" is a vertebrate, including any member of the class mammalia.

As used herein, a "mammal" refers to any mammal including but not limited to human, mouse, rat, sheep, monkey, goat, rabbit, hamster, horse, cow or pig.

A "non-human mammal", as used herein, refers to any mammal that is not a human.

As used herein, "increasing" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, for example, as compared to the level of a reference.

As used herein, "increases" also means increases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a as compared to the level of a reference standard.

As used herein, "decreasing" refers to decreasing by at least 5%, for example, 5, 6, 7, 8, 9, 10, 15, 20, 25, 30, 35, 40, 45, 50, 55, 60, 65, 70, 75, 80, 85, 90, 95, 99 or 100%, for example, as compared to the level of reference.

As used herein, "decreases" also means decreases by at least 1-fold, for example, 1, 2, 3, 4, 5, 6, 7, 8, 9, 10, 15, 20, 30, 40, 50, 60, 70, 80, 90, 100, 200, 500, 1000-fold or more, for example, as compared to the level of a reference.

As used herein, the term "reference" means a standard or control condition (e.g., untreated with a test agent or combination of test agents).

As used herein, the term "eliminate" means to decrease to a level that is undetectable.

As used herein, the term "synergy" or "synergistic effect" is an effect which is greater than the sum of each of the effects taken separately; a greater than additive effect.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure. Unless otherwise defined, all technical and scientific terms used herein have the same meaning as commonly understood by one of ordinary skill in the art to which this invention belongs. In case of conflict, the present specification, including definitions, will control.

Methods and Compositions of the Invention

I. Cell Culture Solutions and Systems

Cell culture solutions and systems to promote homogeneous epithelial stem cell cultures, efficient epithelial organoid formation and scale-up of the same for use in transplantation have now been discovered.

Cell culture solutions comprising an inhibitor of a Bone Morphogenic Protein, an inhibitor of Glycogen synthase kinase-3 beta (GSK3 β) an agent that binds to the Leucine-rich repeat-containing G-protein coupled receptor 5 (LGR5) and a histone deacetylase inhibitor can be utilized to form epithelial cell colonies from isolated epithelial stem cells. In specific embodiments, at least about 25%, about 40%, about 50%, about 75%, about 90% to about 100% of isolated epithelial stem cells form epithelial cell colonies in the presence of this cell culture solution. In addition, at least about 6% of single isolated epithelial stem cells form epithelial cell colonies in the presence of this cell culture solution. Combinations of 1, 6-[[2-[[4-(2,4-Dichlorophenyl)-5-(5-methyl-1H-imidazol-2-yl)-2-pyrimidinyl]amino]ethyl]amino]-3-pyridinecarbonitrile "CHIR99021" (Ring et al., 2003), an inhibitor of Glycogen synthase kinase-3 beta and valproic acid, a histone deacetylase inhibitor, have synergistic effects on colony forming efficiency.

Bone Morphogenic Proteins (BMPs) are members of the TGF-beta superfamily and comprise metalloproteases implicated in embryonic patterning among diverse species as well as post-embryonic cell signaling Inhibitors of BMPs include, for example, agents that bind to a BMP molecule to form a complex wherein the BMP activity is decreased or eliminated, for example by preventing or inhibiting the binding of the BMP molecule to a BMP receptor. Alternatively, the inhibitor is an agent that acts as an antagonist or reverse agonist. This type of inhibitor binds to a BMP receptor and prevents binding of a BMP to the receptor. An example of a latter agent is an antibody that binds a BMP receptor and prevents binding of BMP to the antibody-bound receptor. Inhibitors of BMPs are well known in the art (Rider et al., 2010) and can include, but are not limited to, Noggin, Chordin, Follistatin (Schneyer et al., 1994), DAN, proteins comprising a DAN cysteine-knot domain (including Cerberus and Gremlin), Sclerostin, Twisted Gastrulation, Uterine Sensitivity-Associated Gene-1, Connective-Tissue Growth Factor (Abreu et al., 2002), Inhibin (Wiater and Vale, 2003), BMP-3 (Gamer et al., 2005), Dorsomorphin (Yu et al., 2008) and derivatives, including DMH1 (Hao et al., 2010) and LDN-193189 (Cuny et al., 2008).

Glycogen synthase kinase-3 (GSK3) is a proline-directed serine-threonine kinase that was initially identified as a phosphorylating and inactivating glycogen synthase having two known isoforms, alpha (GSK3A) and beta (GSK-3β). Wnt agonists comprising GSK-3β inhibitors are well known in the art and include, but are not limited to, 1, 6-[[2-[[4-(2,4-Dichlorophenyl)-5-(5-methyl-1H-imidazol-2-yl)-2-pyrimidinyl]amino]ethyl]amino]-3-pyridinecarbonitrile "CHIR99021" (Ring et al., 2003), LiCl (Klein et al., 1996), BIO-acetoxime ((2'Z,3'E)-6-Bromoindirubin-3'-oxime) (Meijer et al., 2003), N6-[2-[[4-(2,4-Dichlorophenyl)-5-(1H-imidazol-2-yl)-2-pyrimidinyl]amino]ethyl]-3-nitro-2,6-pyridinediamine "CHIR98014" (Ring et al., 2003), 3-(2,4-Dichlorophenyl)-4-(1-methyl-1H-indol-3-yl)-1H-pyrrole-2,5-dione "SB 216763" also known as GSK-3 Inhibitor IV (Coghlan et al., 2000), 3-[(3-Chloro-4-hydroxyphenyl)amino]-4-(2-nitrophenyl)-1H-pyrrol-2,5-dione "SB 415286" (Coghlan et al., 2000), 5-ethyl-7,8-dimethoxy-1H-pyrrolo[3,4-c]-isoquinoline-1,3-(2H)-dione "3F8" (Zhong et al., 2009), 9-Bromo-7,12-dihydro-indolo[3,2-d][1]benzazepin-6(5H)-one "Kenpaullone" (Schultz et al., 1999; Zaharevitz et al., 1999), 9-Bromo-7,12-dihydro-pyrido[3',2':2,3]azepino[4,5-b]indol-6(5H)-one "1-Azakenpaullone" (Schultz et al., 1999; Zaharevitz et al., 1999), N-(3-Chloro-4-methylphenyl)-5-(4-ni¬ trophenyl)-1,3,4-oxadiazol-2-amine "TC-G 24" (Khanfar et al., 2010), 2-Methyl-5-[3-[4-(methylsulfinyl)phenyl]-5-benzofuranyl]-1,3,4-oxadiazole "TCS 2002" (Saitoh et al., 2009), N-[(4-Methoxyphenyl)methyl]-N'-(5-nitro-2-thiazolyl)urea "AR-A 014418" (Bhat et al., 2003), 3-[5-[4-(2-Hydroxy-2-methyl-1-oxopropyl)-1-piperazinyl]-2-(trifluoromethyl)phenyl]-4-(1H-indol-3-yl)-1H-pyrrole-2,5-dione "TCS 21311" (Thoma et al., 2011), 3-[[6-(3-aminophenyl)-7H-pyrrolo[2,3-d]pyrimidin-4-yl]oxy]-phenol"TWS 119" (Ding et al., 2003), ((2'Z,3'E)-6-Bromoindirubin-3'-acetoxime) "BIO-acetoxime" also known as GSK-3 Inhibitor IX (Meijer et al., 2003), 4-(2-Amino-4-oxo-2-imidazolin-5-ylidene)-2-bromo-4,5,6,7-tetrahydropyrrolo[2,3-c]azepin-8-one "10Z-Hymenialdisine" (Breton et al., 1997), 2-[(3-iodophenyl)methylsulfanyl]-5-pyridin-4-yl-1,3,4-oxadiazole, also known as GSK-3β Inhibitor II (Wada, 2009), 4-Benzyl-2-methyl-1,2,4-thiadiazolidine-3,5-dione, also known as GSK-3β Inhibitor I (Wada, 2009), 3-Amino-6-(4-((4-methylpiperazin-1-yl)sulfonyl)phenyl)-N-(pyridin-3-yl)pyrazine-2-carboxamide, HCl, also known as GSK-3β Inhibitor XXVII (US Patent Pub. No. 2006/0173014), 4,5-bis(1-Methyl-1H-indol-3-yl)-1,2-dihydropyrazol-3-one, also known as GSK-3β Inhibitor XXVI (Chen et al, 2011), FRATtide peptide SQPETRT-GDDDPHRLLQQLVLSGNLIKEAVRRLHSRRLQ (SEQ ID NO: 1) (Bax et al., 2001), 3-Amino-1H-pyrazolo[3,4-b]quinoxaline "Cdk1/5 Inhibitor" (Andreani et al., 1996, 2000; Katoh et al., 2011) and 4-((5-Bromo-2-pyridinyl)amino)-4-oxobutanoic acid "Bikinin" (De Rybel et al., 2009). Preferably, the inhibitor of GSK-3β is CHIR99021.

Leucine-rich repeat-containing G-protein coupled receptor 5 (LGR5 receptor) is known for its restricted crypt expression and marking of stem cells in multiple adult tissues and cancers. Agents that bind to the LGR5 receptor include but are not limited to R-spondins (Kim et al., 2006; Nam et al., 2006), such as R-spondin 1, R-spondin 2, R-spondin 3 and R-spondin 4. Preferably, the agent that binds to the LGR5 receptor is R-spondin 1.

In alternative embodiments, lithium chloride (LiCl) can be substituted for CHIR99021 or at least about 3 uM CHIR99021 can be substituted for R-spondin 1.

Histones are nuclear proteins that bind DNA and form nucleosomes. They are directly involved with both the packaging of DNA into chromosomes and the regulation of transcription. Histone acetylation/deacetylation is a major factor in regulating chromatin structural dynamics during transcription. Histone deacetylase inhibitors, which decrease or eliminate histone deacetylation, are well known in the art and can include, but are not limited to, Pan-HDAC inhibitors, such as Valproic acid, Trichostatin A, suberoylanilide hydroxamic acid and Suberohydroxamic acid (SBHA), and HDAC6 inhibitors, such as Tubacin, Tubastatin A and Compound 7.

In alternative embodiments, an Atoh1 inhibitor can augment, or be substituted for, a Histone deacetylase inhibitor. Atoh1 inhibitors include, for example, inhibitory nucleic acids that cause a decrease or elimination in the expression of Atoh1 Inhibitory nucleic acids that target Atoh1 are known in the art (Shi et al., 2010).

Cell culture solutions can optionally include an Epidermal Growth Factor and/or a Notch agonist. Epidermal Growth Factor is a cell signaling molecule involved in diverse cellular functions, including cell proliferation, differentiation, motility, and survival, and in tissue development. Notch proteins are single-pass transmembrane receptors that regulate cell fate decisions during development. A Notch agonist includes, for example, an agent that increases Notch activity in a cell. Notch agonists are well known in the art and can include, but are not limited to, a Notch1 antibody (N1 Ab), Delta 1, Delta-like 3, Delta-like 4, Jagged 1, Jagged 2, DSL peptide and Delta D.

In specific embodiments, the cell culture solution comprises between about 5 to about 500 ng/ml EGF, about 5 to about 500 ng/ml Noggin, about 50 to about 1000 ng/ml R-spondin, about 0.1 to about 10 μM CHIR99021 and about 0.1 to about 5 mM Valproic acid.

In other embodiments, the combination of a Wnt agonist and an HDAC6 inhibitor in the cell culture solution is preferred. Accordingly, a cell culture solution can comprise an inhibitor of a Bone Morphogenic Protein, R-spondin 1, a Wnt agonist and a HDAC6 inhibitor.

Wnt proteins are extracellular signaling molecules involved in the control of embryonic development. Wnt agonists are well known in the art and include, but are not limited to, Wnt-1/Int-1(Nusse et al., 1982), Wnt-2/Irp (Int-I-related Protein) (Wainwright et al., 1988), Wnt-2b/13 (Katoh et al., 1996), Wnt-3/Int-4 (Katoh et al., 2001), Wnt-3a (Saitoh et al., 2001), Wnt-4 (Smolich et al., 1993), Wnt-5a (Burrus et al., 1995), Wnt-5b (Burrus et al., 1995), Wnt-6 (Burrus et al., 1995), Wnt-7a (Smolich et al., 1993), Wnt-7b (Burrus et al., 1995), Wnt-8a/8d (Saitoh et al., 2001), Wnt-8b (Lako et al., 1998), Wnt-9a/14 (Bergstein et al., 1997), Wnt-9b/14b/15 (Bergstein et al., 1997), Wnt-10a (Wang et al., 1996), Wnt-10b/12 (Wang et al., 1996), Wnt-11 (Lako et al., 1998), Wnt-16 (Bergstein et al., 1997; Fear et al., 2000), R-spondin 1, R-spondin 2, R-spondin 3, R-spondin 4, Norrin (Planutis et al., 2007), CHIR99021, LiCl, BIO ((2'Z,3'E)-6-Bromoindirubin-3'-oxime), CHIR98014, SB 216763, SB 415286, 3F8, Kenpaullone, 1-Azakenpaullone, TC-G 24, TCS 2002, AR-A 014418, 2-amino-4-[3,4-(methylenedioxy)benzyl-amino]-6-(3-methoxyphenyl)pyrimidine (Liu et al., 2005), 2-[2-(4-Acetylphenyl)diazenyl]-2-(3,4-dihydro-3,3-dimethyl-1(2H)-isoquinolinylidene)acetamide "IQ 1" (Miyabayashi et al., 2007), (3α,5β,12α,20R)-3,12-dihydroxycholan-24-oic acid "DCA" (Pai et al., 2004), (2S)-2-[2-(Indan-5-yloxy)-9-(1,1'-biphenyl-4-yl)methyl)-9H-purin-6-ylamino]-3-phenyl-p-ropan-1-ol "QS 11" (Zhang et al., 2007), piperidinyl diphenylsulfonyl sulfonamide 1 "WAY-316606" (Bodine et al., 2009), (hetero)arylpyrimidines (Gilbert et al., 2010), 10Z-Hymenialdisine, TCS 21311, TWS 119, GSK-3β Inhibitor II, GSK-3β Inhibitor I, GSK-3β Inhibitor XXVII, FRATtide, Cdk1/5 Inhibitor and Bikinin.

Cell culture systems comprise a cell culture solution of the invention and an epithelial organoid, epithelial stem cell or epithelial progenitor cell, or a population of epithelial stem cells or epithelial progenitor cells. Epithelial organoids are known in the art (Yao et al., 2010; Lukacs et al., 2010). Epithelial stem cells include, but are not limited to, stem cells of the intestine, stomach, lung, pancreas, and colon. Epithelial stem cells also include LGR5 positive stem cells, derived from sources including but not limited to intestine, inner ear, brain, kidney, liver, retina, stomach, pancreas, breast, hair follicle, ovary, adrenal medulla, skin, thymus, taste buds, mammory glands, carcinomas and tumors. Epithelial stem cells also include quiescent precursors of LGR5 positive stem cells that express LGR5 (Buczacki et al., 2013). A population of epithelial stem cells or epithelial progenitor cells in a cell culture system can comprise, for example, at least 10%, 20%, 30%, 40%, 50%, 60%, 70%, 80%, 90%, 95%, 99%, or 100% of the cells in the system. Preferably, the population of epithelial stem cells or epithelial progenitor cells is maintained during repeated passages.

In specific embodiments, human epithelial stem cells can be cultured in the presence of additional components including Nicotinamide or a Sirt1 specific HDAC inhibitor such as EX527.

In specific embodiments, epithelial stem cells derived from the inner ear can be cultured in the presence of a Wnt agonist, a histone deacetylase inhibitor, an Epidermal Growth Factor, a basic Fibroblast Growth Factor and optionally, a Bone Morphogenic Protein.

Cell culture systems can comprise additional components, including, but not limited to, a submucosa base and a coating comprising collagen to form 3-dimensional tissue constructs suitable for transplantation. The collagen coating can be overlaid upon and/or surround the selected epithelial tissue or cell type as well as being placed between the selected epithelial tissue or cell type and the submucosa base. Selected epithelial tissue or cell types include, but are not limited to, epithelial stem cells, isolated tissue comprising epithelial stem cells, or epithelial organoids.

Small intestinal submucosa (SIS) is a common, biocompatible and clinically utilized scaffold (de la Fuente et al., 2003; Ueno et al., 2007; Schultz et al., 2002; Kehoe et al., 2012). Submucosal-based scaffolds undergo rapid neovascularization, granulation, biodegradation and are generally well-conserved in terms of protein composition across species. An improved submucosal-based culture system for 3-dimensional tissue constructs is prepared by seeding the submucosa with a preselected epithelial cell type and facilitating growth with a collagen-based overlay. Varying the composition of SIS with this overlay facilitates cell adhesion and growth on SIS, resulting in 3-dimensional expansion of submucosal-adhered cells into large, epithelial organoids. Animal-derived tissue matrix scaffolds (e.g. stomach, bladder, alimentary, respiratory, genital submucosa, and liver basement membrane) from warm-blooded vertebrates are interchangeable with SIS and thus within the scope of this disclosure.

Tissue constructs can be cultured in the presence of cell culture solutions known in the art or cell culture solutions of the invention described herein above. For example, tissue constructs can be cultured in the presence of a cell culture solution comprising an inhibitor of a Bone Morphogenic Protein, R-spondin 1, CHIR99021 and a histone deacetylase inhibitor. Additionally, the submucosa base can contain similar combinations of small molecules and/or growth factors, including, but not limited to, Epidermal Growth Factor, a Bone Morphogenic Protein, R-spondin 1, CHIR99021, Y-27632 and a histone deacetylase inhibitor.

In alternative embodiments, collagen-free epithelial cell culture systems are provided, where the submucosa base contains combinations of small molecules and/or growth factors such as Epidermal Growth Factor, a Bone Morphogenic Protein, R-spondin 1, CHIR99021, Y-27632 and a histone deacetylase inhibitor. Collagen-free tissue constructs can be cultured in the presence of cell culture solutions known in the art or as described herein above.

II. Methods Employing Cell Culture Solutions and Systems

Cell culture solutions and systems of the invention can be used to form epithelial organoids from isolated epithelial stem cells with high efficiency. In a specific embodiment, incubating isolated epithelial stem cells in the presence of Noggin, R-spondin 1, CHIR99021 and a histone deacetylase inhibitor (e.g., Valproic acid) forms epithelial cell colonies with an efficiency of at least about 25%, 35%, 40%, 50%, 60%, 70%, 80%, 90% or 100%. In another specific embodiment, single isolated epithelial stem cells incubated in the presence of Noggin, R-spondin 1, CHIR99021 and a histone deacetylase inhibitor form epithelial cell colonies with an efficiency of least about 6% to about 100%.

Epithelial stem cells maintained within cell culture solutions and systems of the invention can be subsequently directed into specific differentiation pathways, including those that result in the formation of paneth cells, enterocytes, goblet cells and enteroendocrine cells.

Paneth cells have been shown to be an important constituent of the Lgr5$^+$ stem cell niche within intestinal crypts that provide essential signals for stem cell maintenance (Sato et al., 2011b; Yilmaz et al., 2012). First incubating epithelial stem cells in the presence of a cell culture solution comprising an inhibitor of a BMP, R-spondin 1, CHIR99021 and a histone deacetylase inhibitor (e.g., valproic acid) and subsequently further incubating the epithelial stem cells in the presence of at least one Wnt agonist and at least one inhibitor of Notch (e.g., DAPT) produces paneth cells. Likewise, subsequent further incubation of an epithelial stem cell in the presence of at least one Wnt inhibitor and at least one histone deacetylase inhibitor produces enterocytes; and subsequent further incubation of an epithelial stem cell in the presence of at least one Wnt inhibitor and at least one Notch inhibitor produces goblet cells. The Wnt inhibitor can be, but is not limited to, N-(6-Methyl-2-benzothiazolyl)-2-[(3,4,6,7-tetrahydro-4-oxo-3-phenylthieno[3,2-d]pyrimidin-2-yl)thio]-acetamide ("IWP-2") (Chen, Dodge et al. 2009). The Notch inhibitor can be, but is not limited to N-[N-(3, 5-Difluorophenacetyl)-L-alanyl]-S-phenylglycine t-butyl ester ("DAPT" or "LY-374973") (Dovey, John et al. 2001), N1-[(7S)-6,7-dihydro-6-oxo-5H-dibenz[b,d]azepin-7-yl]-2, 2-dimethyl-N3-(2,2,3,3,3-pentafluoropropyl)-("RO4929097", Propanediamide) (He, Luistro et al. 2011), (S)-2-hydroxy-3-methyl-N—((S)-1((S)-3-methyl-2-oxo-2, 3,4,5-tetrahydro-1H-benzo[d]azepin-1-ylamino)-1-oxopropan-2-yl)butanamide ("LY450139") (Lanz, Hosley et al. 2004), N-[(1S)-2-[[(7S)-6,7-dihydro-5-methyl-6-oxo-5H-dibenz[b,d]azepin-7-yl]amino]-1-methyl-2-oxoethyl]-2-hydroxy-3-methyl-, (2S)-("LY900009", Butanamide) (Selleckchem: Catalog No. S7168), N-[(1S)-2-[[(7S)-6,7-dihydro-5-(2-hydroxyethyl)-6-oxo-5H-pyrido[3,2-a][3]benzazepin-7-yl]amino]-1-methyl-2-oxoethyl]-4,4,4-trifluoro-("LY3039478", Butanamide) Selleckchem: Catalog No. S7169, N-[(1S)-2-[[(7S)-6,7-dihydro-5-methyl-6-oxo-5H-dibenz[b,d]azepin-7-yl]amino]-1-methyl-2-oxoethyl]-3,5-difluoro-α-hydroxy-, (αS)-("LY411575", Benzeneacetamide) (Wehner, Cizelsky et al. 2014), 7-(S)-[N'(3,5-difluorophenylacetyl)-L-alaninyl]amino-5-methyl-5,7-dihydro-6H-dibenz[b,d]azepin-6-one ("YO-01027" (DBZ)) (Milano, McKay et al. 2004), (2R)-2-(N-(2-fluoro-4-(1,2,4-oxadiazol-3-yl)benzyl)-4-chlorophenylsulfonamido)-5,5,5- trifluoropentanamide ("BMS-708163") (Saito, Fu et al. 2014), (2R,3S)—N-[(3S)-1-Methyl-2-oxo-5-phenyl-2,3-dihydro-1H-1,4-benzodiazepin-3-yl]-2,3-bis(3,3,3-trifluoropropyl)succinamide ("BMS-906024") (Huang, Greer et al. 2009), (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide ("Compound E") (Milano, McKay et al. 2004), 2-[(1R)-1-[[(4-Chlorophenyl)sulfonyl](2,5-difluorophenyl)amino]ethyl-5-fluorobenzenebutanoic acid ("BMS-299897") (Anderson, Holtz et al. 2005), SAHM1 Calbiochem Catalogue Number: 491002, (Abeta42-Selective) Calbiochem Catalogue Number: 565792, and N-(2-Bromophenyl)-N'-(2-hydroxy-4-nitrophenyl)urea ("SB 225002") (Bakshi, Jin et al. 2009).

Subsequent further incubation of an epithelial stem cell in the presence of at least of at least one inhibitor of Notch and an agent that inhibits at least one of a Receptor Tyrosine Kinase (RTK), a Mitogen-activated protein (MAP) kinase, also refereed to as MAPK/ERK, or an Extracellular signal-regulated kinase (ERK), also referred to as MAPK/ERK, produces enteroendocrine cells. The MAP kinase can be, but is not limited to, Mitogen-activated protein kinase kinase and the agent that inhibits a MAP kinase, can be, but is not limited to, N-[(2S)-2,3-dihydroxypropyl]-3-[(2-fluoro-4-iodophenyl)amino]-4-pyridinecarboxamide ("AS-703026") (Kim, Kong et al. 2010), N-[(2R)-2,3-Dihydroxypropoxy]-3,4-difluoro-2-[(2-fluoro-4-iodophenyl)amino]-benzamide ("PD0325901") (Thompson and Lyons 2005), 5-(2-Phenyl-pyrazolo[1,5-a]pyridin-3-yl)-1H-pyrazolo[3,4-c]pyridazin-3-ylamine ("FR 180204") (Ohori, Kinoshita et al. 2005), 2-(2-amino-3-methoxyphenyl)-4H-chromen-4-one ("PD98059") (Alessi, Cuenda et al. 1995), 6-(4-bromo-2-chlorophenylamino)-7-fluoro-N-(2-hydroxyethoxy)-3-methyl-3H-benzo[d]imidazole-5-carboxamide ("Selumetinib") (Huynh, Soo et al. 2007), (Z)-3-amino-3-(4-aminophenylthio)-2-(2-(trifluoromethyl)phenyl) acrylonitrile ("SL-327") (Chen, Operana et al. 2005), (2Z, 3Z)-2,3-bis(amino(2-aminophenylthio)methylene) succinonitrile,ethanol ("U0126") (Favata, Horiuchi et al. 1998), (R)-3-(2,3-dihydroxypropyl)-6-fluoro-5-(2-fluoro-4-iodophenylamino)-8-methylpyrido[2,3-d]pyrimidine-4,7 (3H,8H)-dione ("TAK-733") (Dong, Dougan et al. 2011) and N-(3-(3-cyclopropyl-5-(2-fluoro-4-iodophenylamino)-6,8-dimethyl-2,4,7-trioxo-3,4,6,7-tetrahydropyrido[4,3-d]pyrimidin-1(2H)-yl)phenyl)acetamide ("Trametinib") (Gilmartin, Bleam et al. 2011). The agent that inhibits an RTK can be, but is not limited to, N-(3-chloro-4-fluorophenyl)-7-methoxy-6-[3-(4-morpholinyl)propoxy]-4-quinazolinamine ("Gefitinib") (Ciardiello 2000), (E)-2-Cyano-3-(3, 4-dihydroxyphenyl)-2-propenamide ("AG 99") (Gazit, Yaish et al. 1989),4-[[(2S)-2-(3-Chlorophenyl)-2-hydroxyethyl]amino]-3-[7-methyl-5-(4-morphinyl)-1H-benzimidazol-2-yl]-2 (1H)-pyridinone ("BMS 536924") (Huang, Greer et al. 2009), 5-(2-Phenyl-pyrazolo[1,5-a]pyridin-3-yl)-1H-pyrazolo[3,4-c]pyridazin-3-ol ("FR 180209") (Anastassiadis, Duong-Ly et al. 2013), N-(3-ethynylphenyl)-6,7-bis(2-methoxyethoxy)quinazolin-4-amine hydrochloride ("Erlotinib") (Kuiper, Heideman et al. 2014), (S,E)-N-(4-(3-chloro-4-fluorophenylamino)-7-(tetrahydrofuran-3-yloxy)quinazolin-6-yl)-4-(dimethylamino)but-2-enamide ("Afatinib") (Minkovsky and Berezov 2008), N-(4-(3-fluorobenzyloxy)-3-chlorophenyl)-6-(5-(((2-(methylsulfonyl) ethylamino)methyl)furan-2-yl)quinazolin-4-amine,di4-methylbenzenesulfonate ("Lapatinib") (Xia, Mullin et al. 2002), N-(3-(5-chloro-2-methoxy-4-(4-methylpiperazin-1-yl)phenylamino)pyrimidin-4-yloxy)phenyl)acrylamide ("WZ4002") (Sakuma, Yamazaki et al. 2012) and 2-[(3,4-dihydroxyphenyl)methylene]-("AG-18", Propanedinitrile) (Gazit, Yaish et al. 1989).

Cell culture solutions and systems of the invention can additionally be used to form 3-dimensional tissue constructs comprising transplantable epithelium for regenerative purposes. Such tissue constructs can be transplanted into hosts according to methods known in the art (Lloyd et al. 2006; Gupta et al. 2006; Yui et al. 2012). Tissues that are susceptible to treatment include all damaged tissues, including those which may have been damaged by disease, injury, trauma, an autoimmune reaction, or by a viral or bacterial infection. Minimally-invasive transplant techniques can be employed, including image-guided technology. Tissue constructs can be injected or implanted directly into the damaged tissue, where they may multiply and eventually differentiate into the required cell type, in accordance with their location in the body. Tissue constructs may be directly implanted or injected via colonic enema. Micronization can be employed prior to oral delivery for upper intestinal applications. Accordingly, damaged tissues particularly well suited for repair include tissues of the colon, small intestine, pancreas, esophagus and gastric system. The skilled person will be aware what the appropriate dosage of tissue constructs will be for a particular condition to be treated.

Cell culture solutions and systems of the invention can additionally be used to predict the efficacy of a chemotherapeutic agent, or combinations of chemotherapeutic agents, in vivo. Such methods are particularly relevant to use in clinical settings since many patients are treated with multiple drugs.

Tumor organoids can be formed according to methods known in the art by culturing isolated tumor cell aggregates or single cells in culture solutions of the invention (Sato et al., 2011a). Such cultures can be used as clinical models for various cancers, including but not limited to, prostate cancer, breast cancer, gastric cancer, pancreatic cancer, lung cancer, brain cancer, colon cancer, intestinal cancer and bladder cancer.

Tumor organoids can be incubated in the presence of a cell culture solution of the invention (e.g., comprising an inhibitor of a BMP, R-spondin 1, a Wnt agonist, a histone deacetylase inhibitor) and a chemotherapeutic agent(s). Next, a relevant parameter is measured and evaluated. Relevant parameters include inhibition of cell viability, inhibition cell proliferation, inhibition of tumor associated gene expression, activation of apoptosis and inhibition of cell survival. Detecting an increase in the parameter compared to a reference (e.g., control) indicates efficacy of the chemotherapeutic agent relative to the tumor organoid, which is predictive of efficacy of the chemotherapeutic agent(s) in vivo.

In general, chemotherapeutic agents are incubated with the cell culture system comprising tumor organoids in a dosage range estimated to be therapeutic and for a duration sufficient to produce a physiological effect. The incubation time can range between about 1 hour to 24 hours, or can be extended as necessary for several days or even weeks. The incubation conditions typically involve using culture solutions of the invention and maintaining temperatures of about 37° C.

A chemotherapeutic agent is any substance that is evaluated for its ability to cure, mitigate, treat, or prevent cancer in a subject and includes, but is not limited to, a chemical compound, biologic agent, protein, peptide, nucleic acid, lipid, polysaccharide, supplement, and an antibody.

Inhibition of tumor associated gene expression can be determined according to methods known in the art. For example, inhibition of tumor associated gene expression relative to a control can be detected by microchip analysis, RT-PCR, in situ hybridization, fluorescence in situ hybridization or Northern analysis Inhibition of tumor associated protein expression relative to a control can be detected by quantitative Western blot, immunohistochemistry, immunofluorescence, enzyme-linked immunosorbent assay, amino acid sequence analysis, fluorescence activated cell sorting or protein concentration assays. For example, a gastric cancer gene screening assay can be utilized to identify changes in gene expression for angiotensin, apolipoprotein E, apolipoprotein A-I, ceruloplasmin, prothrombin, fibronectin, vitamin D-binding protein, gelsolin, inter-alpha-trypsin inhibitor heavy chain H3, kininogen-1, serum paraoxonase/arylesterase 1, alpha-1-antichymotrypsin and transthyretin.

Activation of apoptosis can be determined according to methods known in the art. For example, increases in cell death relative to a control can be detected by lactate dehydrogenase release, caspase activity, annexin V staining, phosphatidylserine staining or TUNEL assay. Certain assays detect comparatively late events in the process of cell death, such as lactate dehydrogenase release. Caspase activation is a common feature of chronic toxicity and cell death. Caspase activity can be measured relatively quickly after a toxic insult (30 minutes to 4 hours) by fluorescence spectroscopy, thus lending itself to high-throughput screening techniques. Other markers and assays commonly used to monitor apoptosis or necrosis of cells can include, but are not limited to, the presence of phosphatidylserine on the outer leaflet of the plasma membrane of affected cells, annexin V staining, and terminal deoxynucleotidyltransferase nick-end labeling assay (TUNEL).

Inhibition of cell viability can be determined according to methods known in the art, including, but not limited to, differential counting of viable and dead cells using vital dyes, such as trypan blue, 4,6-diaminophenylindole (DAPI), and propidium iodide.

Inhibition of cell proliferation can be determined according to methods known in the art, including, but not limited to quantification of DNA via bromodeoxyuridine incorporation, measuring tritiated thymidine (3H-thymidine), propidium iodide staining, intracellular metabolic analysis via tetrazolium salt or AlamarBlue reduction and quantitation of intracellular ATP concentration. Further methods include direct measuring total nuclei acid content of lysed cells via spectrophotometric analysis; fluorescent tagging with anti-cdc6-Peptide Antibody, anti-Human mRNA-Binding Protein HuR Antibody (Anti-HuR Antibody), antibodies against D Cyclins and Cyclin-Dependent Kinase Inhibitors; Ki-67 antigen detection; measuring protein content via quantitative Western blot, immunohistochemistry, immunofluorescence, enzyme-linked immunosorbent assay, amino acid sequence analysis, fluorescence activated cell sorting or protein concentration assays. Commercially available kits employing the above methods include ChromaTide™ nucleotide labelling, Succinimidyl ester of carboxyfluorescein diacetate, ABSOLUTE-S™ SBIP Cell Proliferation Assay Kit, Vybrant DiI Cell-Labeling Solution, CyQUANT Cell Proliferation Assay Kit, Vybrant™ MTT Cell Proliferation Assay Kit, and FluoReporter™ Blue Fluorometric nucleic acid assay kit.

Suppression of cell survival can be determined according to methods known in the art, including clonogenic assays.

III. Methods of Promoting Expansion of Epithelial Cells or Growth of Epithelial Tissues In Vivo Epithelial stem cells, including stem cells of the intestine, stomach, lung, pancreas and colon and in particular, LGR5 positive stem cells present within intestine, inner ear, brain, kidney, liver, retina, stomach, pancreas, breast, hair follicle, ovary, adrenal medulla, skin, thymus, taste buds, and mammory glands, can be expanded in vivo through administration of a Wnt agonist and a histone deacetylase inhibitor or a Wnt agonist and a Notch agonist to a subject. These combinations promote expansion of epithelial cells resulting in growth of epithelial tissues in vivo.

In specific embodiments, intestinal epithelial cells can be formed in vivo following administration of a Wnt agonist, e.g., CHIR99021 and a histone deacetylase inhibitor, e.g., Valproic acid, or a Wnt agonist, e.g., CHIR99021 and a Notch agonist to a subject.

In some embodiments, these combinations, e.g., CHIR99021 and Valproic acid, can treat intestinal disorders in a subject, including, but not limited to, enterocolitis; viral infections, such as non-specific enteritis or specific viral enteritis; diverticulitis; bacterial enterocolitis, such as *salmonellosis*, shigellosis, *campylobacter* enterocolitis, or yersinia enterocolitis; protozoan infections such as amebiasis; helminthic infection; and pseudomembraneous colitis and pulmonary complications in cystic fibrosis and chronic obstructive pulmonary disease; appendicitis; atrophic gastritis; Barrett's esophagus; pneumonitis; cervicitis; chronic interstitial nephritis; colitis; colonic diverticulitis; conjunctivitis; contact dermatitis; Curling's ulcers; Cushing's ulcers; cystitis; gangrene; gingivitis; mastitis; esophagitis; pancreatitis; panniculitis; phlegmonous gastritis; glomerulonephritis; and autoimmune diseases including, but not limited to, inflammatory bowel disease, ulcerative colitis, Crohn's disease, Addison's disease and glomerulonephritis (e.g., crescentic glomerulonephritis, proliferative glomerulonephritis).

The dosage administered will be dependent upon the age, sex, health, and weight of the recipient, kind of concurrent treatment, if any, frequency of treatment and the nature of the effect desired. The dose ranges for the administration of the compositions of the present invention are those large enough to produce the desired effect. The doses should not be so large as to cause adverse side effects, such as unwanted cross-reactions, anaphylactic reactions, and the like. Generally, the dosage will vary with the condition and extent of the disease in the patient. Counter indications, if any, immune tolerance, and other variables will also affect the proper dosage. For instance, taking into account such factors as the age, weight, sex, species, general health/condition of the patient, the condition to be treated, timing of treatments, the LD50 of the active ingredient involved in a suitable animal model (e.g., rodent, mice), and other known factors; and such dosages can be on the order of micrograms to milligrams such as on the order of 0.5 to 500 mg/kg, or another suitable amount, or can be computed from Examples herein, e.g., considering the average weight of a typical test animal (such as mice) and the dosages administered thereto (e.g., 100 micrograms), and thus the skilled artisan can determine dosages without undue experimentation. In particular, in human subjects, CHIR99021 is administered in an amount of about 0.1 mg/kg/day to about 100 mg/kg/day and the amount of Valproic acid is administered in an amount of about 1 mg/kg/day to about 1000 mg/kg/day. In specific embodiments, the amount of Valproic acid is 15-40 mg/kg/day.

The pharmaceutical compositions of CHIR99021 and Valproic acid can be concomitantly or sequentially administered by any means that achieve their intended purpose.

For example, administration can be by topical, parenteral, subcutaneous, intravenous, intramuscular, intraperitoneal, transdermal, rectal or buccal routes. Alternatively, or concurrently, administration can be by the oral route. From the foregoing description, it will be apparent that variations and modifications may be made to the invention described herein to adopt it to various usages and conditions. Methods and materials are described herein for use in the present invention; other, suitable methods and materials known in the art can also be used. The materials, methods, and examples are illustrative only and not intended to be limiting. Such embodiments are also within the scope of the following claims. The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof. All publications, patent applications, patents, sequences, database entries, and other references mentioned herein are incorporated by reference in their entirety.

Exemplary embodiments of the invention can also be described by any one of the following numbered paragraphs:

1. A method of forming an enterocyte in a cell culture system comprising incubating an epithelial stem cell in the presence of at least one Wnt inhibitor and at least one histone deacetylase inhibitor, each in an amount sufficient to produce an enterocyte in a cell culture system.

2. The method of paragraph 1, wherein the histone deacetylase inhibitor is a Pan-HDAC inhibitor.

3. The method of paragraph 2, wherein the Pan-HDAC inhibitor is selected from the group consisting of Valproic acid, Trichostatin A, suberoylanilide hydroxamic acid and SBHA.

4. The method of paragraph 1, wherein the histone deacetylase inhibitor is an HDAC6 inhibitor.

5. The method of paragraph 4, wherein the HDAC6 inhibitor is selected from the group consisting of Tubacin, Tubastatin A and Compound 7.

6. The method of paragraph 1, wherein the Wnt inhibitor is selected from the group consisting of IWP-2, XAV-939, ICG-001, LGK-974, IWR-1-endo, KY02111, Wnt-059, DKK-1, FH-535, Box5, Peptide Pen-N3, Anti-SFRP antibody, and Anti-LRP6 antibody.

7. The method of paragraph 1, further comprising incubating the epithelial stem cell in the presence of an inhibitor of a Bone Morphogenic Protein.

8. The method of paragraph 7, wherein the Bone Morphogenic Protein is selected from the group consisting of Noggin, Chordin, Follistatin, DAN, proteins comprising a DAN cysteine-knot domain, Sclerostin, Twisted Gastrulation, Uterine Sensitivity-Associated Gene-1, Connective-Tissue Growth Factor, Inhibin, BMP-3, and Dorsomorphin.

9. The method of paragraph 1, further comprising incubating the epithelial stem cell in the presence of an Epidermal Growth Factor.

10. A method of forming a goblet cell in a cell culture system comprising incubating an epithelial stem cell in the presence of at least one Wnt inhibitor and at least one Notch inhibitor, each in an amount sufficient to produce a goblet cell in a cell culture system.

11. The method of paragraph 10, wherein the Notch inhibitor is selected from the group consisting of DAPT, RO4929097, LY450139, LY900009, LY3039478, LY411575, YO-01027, BMS-708163, BMS-906024, Compound E, BMS-299897, SAHM1, Abeta42-Selective and SB 225002.

12. The method of paragraph 10, wherein the Wnt inhibitor is selected from the group consisting of IWP-2, XAV-939, ICG-001, LGK-974, IWR-1-endo, KY02111, Wnt-059, DKK-1, FH-535, Box5, Peptide Pen-N3, Anti-SFRP antibody, Anti-LRP6 antibody, and Anti-APC antibody.

13. The method of paragraph 10, further comprising incubating the epithelial stem cell in the presence of an Epidermal Growth Factor.

14. A method of forming an enteroendocrine cell in a culture system comprising incubating an epithelial stem cell in the presence of at least one inhibitor of Notch and an agent that inhibits at least one of a Receptor Tyrosine Kinase, a Mitogen-activated protein (MAP) kinase or an Extracellular signal-regulated kinase (ERK), each in an amount sufficient to produce an enteroendocrine cell in a cell culture system.

15. The method of paragraph 14, wherein the Notch inhibitor is selected from the group consisting of DAPT, RO4929097, LY450139, LY900009, LY3039478, LY411575, YO-01027, BMS-708163, BMS-906024, Compound E, BMS-299897, SAHM1, Abeta42-Selective and SB 225002.

16. The method of paragraph 14, wherein the MAP kinase is Mitogen-activated protein kinase kinase (MEK).

17. The method of paragraph 14, wherein the agent that inhibits a MAP kinase is selected from the group consisting of AS-703026, PD0325901, PD98059, Selumetinib, SL-327, U0126, TAK-733 and Trametinib.

18. The method of paragraph 14, wherein the agent that inhibits an RTK is selected from the group consisting of Gefitinib, AG 99, Erlotinib, Afatinib, Lapatinib, WZ4002 and AG-18.

19. The method of paragraph 14, wherein the agent that inhibits an ERK is AS-703026 or PD0325901.

20. The method of paragraph 14, further comprising incubating the epithelial stem cell in the presence of an inhibitor of a Bone Morphogenic Protein.

21. The method of paragraph 20, wherein the Bone Morphogenic Protein is selected from the group consisting of Noggin, Chordin, Follistatin, DAN, proteins comprising a DAN cysteine-knot domain, Sclerostin, Twisted Gastrulation, Uterine Sensitivity-Associated Gene-1, Connective-Tissue Growth Factor, Inhibin, BMP-3, and Dorsomorphin.

22. The method of paragraph 14, further comprising incubating the epithelial stem cell in the presence of an agent that binds to the Leucine-rich repeat-containing G-protein coupled receptor 5.

23. The method of paragraph 22, wherein the agent that binds to the Leucine-rich repeat-containing G-protein coupled receptor 5 is selected from the group consisting of R-spondin 1, R-spondin 2, R-spondin 3 and R-spondin 4

24. The method of paragraph 14, further comprising incubating the epithelial stem cell in the presence of an Epidermal Growth Factor.

25. A method of forming intestinal epithelial cells in a subject in need thereof, comprising administering to the subject a Wnt agonist and a histone deacetylase inhibitor in an amount sufficient to form intestinal epithelial cells in the subject.

26. The method of paragraph 25, wherein the subject is a human.

27. The method of paragraph 25, wherein the Wnt agonist is selected from the group consisting of: Wnt-1/Int-1, Wnt-2/Irp (Int-I-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, Wnt-16, R-spondin 1, R-spondin 2, R-spondin 3, R-spondin 4, Norrin, CHIR99021, LiCl, BIO ((2'Z,3'E)-6-Bromoindirubin-3'-oxime), CHIR98014, SB 216763, SB 415286, 3F8, Kenpaullone, 1-Azakenpaullone, TC-G 24, TCS 2002, AR-A 014418, 2-amino-4-[3,4-(methylenedioxy)benzyl-amino]-6-(3-methoxyphenyl)pyrimidine, IQ 1, DCA, QS 11, WAY-316606, (hetero)arylpyrimidines, 10Z-Hymenialdisine, TCS 21311, TWS 119, GSK-3 Inhibitor IX, GSK-3 Inhibitor IV, GSK-3β Inhibitor II, GSK-3β Inhibitor I, GSK-3β Inhibitor XXVII, GSK-3beta Inhibitor XXVI, FRATtide, Cdk1/5 Inhibitor, Bikinin, and 1-Azakenpaullone.

28. The method of paragraph 25, wherein the histone deacetylase inhibitor is a Pan-HDAC inhibitor.

29. The method of paragraph 28, wherein the Pan-HDAC inhibitor is selected from the group consisting of Valproic acid, Trichostatin A, suberoylanilide hydroxamic acid and SBHA.

30. The method of paragraph 25, wherein the histone deacetylase inhibitor is an HDAC6 inhibitor.

31. The method of paragraph 30, wherein the HDAC6 inhibitor is selected from the group consisting of Tubacin, Tubastatin A and Compound 7.

32. The method of paragraph 25, wherein the Wnt agonist is CHIR99021 and the histone deacetylase inhibitor is Valproic acid.

33. The method of paragraph 32, wherein the CHIR99021 is administered in an amount of about 0.1 mg/kg/day to about 100 mg/kg/day and the Valproic acid is administered in an amount of about 1 mg/kg/day to about 1000 mg/kg/day.

34. A method of generating epithelial tissue in a subject in need thereof, comprising administering a Wnt agonist and a histone deacetylase inhibitor or a Wnt agonist and a Notch agonist to the subject in an amount sufficient to increase epithelial stem cells within the epithelial tissue, thereby generating epithelial tissue in the subject.

35. The method of paragraph 34, wherein the epithelial stem cell is a LGR5 positive stem cell present within intestine, inner ear, brain, kidney, liver, retina, stomach, pancreas, breast, hair follicle, ovary, adrenal medulla, skin, thymus, taste buds or mammary glands.

36. A method of forming intestinal epithelial cells in a subject in need thereof, comprising administering to the subject a Wnt agonist and a Notch agonist in an amount sufficient to form intestinal epithelial cells in the subject.

35. The method of paragraph 34 or 36, wherein the subject is a human.

36. The method of paragraph 34 or 36, wherein the Wnt agonist is selected from the group consisting of: Wnt-1/Int-1, Wnt-2/Irp (Int-I-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, Wnt-16, R-spondin 1, R-spondin 2, R-spondin 3, R-spondin 4, Norrin, CHIR99021, LiCl, BIO ((2'Z,3'E)-6-Bromoindirubin-3'-oxime), CHIR98014, SB 216763, SB 415286, 3F8, Kenpaullone, 1-Azakenpaullone, TC-G 24, TCS 2002, AR-A 014418, 2-amino-4-[3,4-(methylenedioxy)benzyl-amino]-6-(3-methoxyphenyl)pyrimidine, IQ 1, DCA, QS 11, WAY-316606, (hetero)arylpyrimidines, 10Z-Hymenialdisine, TCS 21311, TWS 119, GSK-3 Inhibitor IX, GSK-3 Inhibitor IV, GSK-3β Inhibitor II, GSK-3β Inhibitor I, GSK-3β Inhibitor XXVII, GSK-3beta Inhibitor XXVI, FRATtide, Cdk1/5 Inhibitor, Bikinin, and 1-Azakenpaullone.

37. The method of paragraph 34 or 36, wherein the Notch agonist is a Notch1 antibody (N1 Ab), Delta 1, Delta-like 3, Delta-like 4, Jagged 1, Jagged 2, DSL peptide and Delta D.

38. A method of treating an intestinal disorder, the method comprising administering to the subject a Wnt agonist and a histone deacetylase inhibitor or a Wnt agonist and a Notch.

39. The method of paragraph 38, wherein the subject is a human.

40. The method of paragraph 38, wherein the Wnt agonist is selected from the group consisting of: Wnt-1/Int-1, Wnt-2/Irp (Int-I-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, Wnt-16, R-spondin 1, R-spondin 2, R-spondin 3, R-spondin 4, Norrin, CHIR99021, LiCl, BIO ((2'Z,3'E)-6-Bromoindirubin-3'-oxime), CHIR98014, SB 216763, SB 415286, 3F8, Kenpaullone, 1-Azakenpaullone, TC-G 24, TCS 2002, AR-A 014418, 2-amino-4-[3,4-(methylenedioxy)benzyl-amino]-6-(3-methoxyphenyl)pyrimidine, IQ 1, DCA, QS 11, WAY-316606, (hetero)arylpyrimidines, 10Z-Hymenialdisine, TCS 21311, TWS 119, GSK-3 Inhibitor IX, GSK-3 Inhibitor IV, GSK-3β Inhibitor II, GSK-3β Inhibitor I, GSK-3β Inhibitor XXVII, GSK-3beta Inhibitor XXVI, FRATtide, Cdk1/5 Inhibitor, Bikinin, and 1-Azakenpaullone.

41. The method of paragraph 38, wherein the histone deacetylase inhibitor is a Pan-HDAC inhibitor.

42. The method of paragraph 41, wherein the Pan-HDAC inhibitor is selected from the group consisting of Valproic acid, Trichostatin A, suberoylanilide hydroxamic acid and SBHA.

43. The method of paragraph 38, wherein the histone deacetylase inhibitor is an HDAC6 inhibitor.

44. The method of paragraph 43, wherein the HDAC6 inhibitor is selected from the group consisting of Tubacin, Tubastatin A and Compound 7.

45. The method of paragraph 38, wherein the Wnt agonist is CHIR99021 and the histone deacetylase inhibitor is Valproic acid.

46. The method of paragraph 45, wherein the CHIR99021 is administered in an amount of about 0.1 mg/kg/day to about 100 mg/kg/day and the Valproic acid is administered in an amount of about 1 mg/kg/day to about 1000 mg/kg/day.

47. The method of paragraph 38, wherein the Notch agonist is a Notch1 antibody (N1 Ab), Delta 1, Delta-like 3, Delta-like 4, Jagged 1, Jagged 2, DSL peptide and Delta D.

48. The method of any of paragraphs 38-47, wherein the intestinal disorder is selected from the group consisting of: enterocolitis; viral infections, such as non-specific enteritis or specific viral enteritis; diverticulitis; bacterial enterocolitis, such as *salmonellosis*, shigellosis, *campylobacter* enterocolitis, or yersinia enterocolitis; protozoan infections such as amebiasis; helminthic infection; and pseudomembraneous colitis and pulmonary complications in cystic fibrosis and chronic obstructive pulmonary disease; appendicitis; atrophic gastritis; Barrett's esophagus; pneumonitis; cervicitis; chronic interstitial nephritis; colitis; colonic diverticulitis; conjunctivitis; contact dermatitis; Curling's ulcers; Cushing's ulcers; cystitis; gangrene; gingivitis; mastitis; esophagitis; pancreatitis; panniculitis; phlegmonous gastritis; glomerulonephritis; and autoimmune diseases including, but not limited to, inflammatory bowel disease, ulcerative colitis, Crohn's disease, Addison's disease and glomerulonephritis (e.g., crescentic glomerulonephritis, proliferative glomerulonephritis).

The invention is further described in the following examples, which do not limit the scope of the invention described in the claims.

EXAMPLES

Example 1: Self-Renewal of Lgr5+ Intestinal Stem Cells is Maintained Using a Combination of Small Molecules The self-renewal and differentiation of ISC is controlled by the coordinated regulation of several signaling pathways (Crosnier, Stamataki, & Lewis, 2006; Scoville, Sato, He, & Li, 2008; van der Flier & Clevers, 2009). In this study small molecules were identified that target relevant signaling pathways to maintain the self-renewal status of Lgr5+ stem cells and to control their differentiation independently of cues provided by other cell types.

Crypts and single Lgr5-GFP cells were isolated as previously described (Sato et al., 2009). Briefly, the proximal half of the small intestine was harvested, opened longitudinally, and washed with cold PBS to remove luminal content. The tissue was then cut into 2-4 mm pieces with scissors and further washed 5-10 times with cold PBS by pipetting up and down using a 10-ml pipette. Tissue fragments were incubated with 2 mM EDTA in PBS for 30 min on ice. After removal of EDTA, tissue fragments were washed with PBS to release crypts. Supernatant fractions enriched in crypts were collected, passed through a 70 μm cell strainer and centrifuged at 300 g for 5 minutes. The cell pellet was re-suspended with cell culture media without growth factors and centrifuged at 150 g to remove single cells. Crypts were then cultured or used for single cell isolation. To obtain single cells, crypts were incubated in culture medium for 45 minutes at 37° C. and triturated with a glass pipette. Dissociated cells were passed through 20 μm cell strainer, negative stained with propidium iodide and single viable GFP-high cells were sorted by flow cytometry (FACS Aria, BD) as previously described (Sato et al., 2009). Small intestinal crypts isolated from Lgr5-EGFP-ires-CreERT2 mice were embedded in Matrigel and cultured under conventional culture conditions in the presence of EGF, Noggin and R-spondin 1 (collectively referred to as ENR) leading to organoids with crypts and villus-like domains and GFP+ cells at the crypt tips, consistent with previous reports (Sato et al., 2009). Isolated crypts or single cells were cultured as previously described (Sato et al., 2009) with minimal modification. Briefly, crypts or single cells were entrapped in Matrigel and plated at the center of wells in a 24-well plate. After polymerization of Matrigel (growth factor reduced; BD Bioscience), 500 μl of culture medium (Advanced DMEM/F12 (Life Technologies)) was added containing growth factors including EGF (50 ng/ml, Life Technologies), Noggin (100 ng/ml, Peprotech) and R-spondin 1 (500 ng/ml, R&D) and small molecules including CHIR99021 (3 μM, Stemgent) and Valproic Acid (1 mM, Sigma-Aldrich). For comparison of different culture conditions, small molecules or growth factors were added to freshly isolated crypts immediately after plating in Matrigel to test the ability to minimize potential differentiation of the ISC within the crypts and thus sustain crypt cultures. Cell culture media was changed every other day. For single cell culture, cells were embedded in Matrigel containing Jagged-1 peptide (1 μM; AnaSpec) and Y-27632 (10 μM; Tocris) was added for the first 2 days. Cells were passaged either as cell colonies as previously described (Sato et al., 2009) or as single cells. For single cell passage, cell culture medium was removed and Accutane (Life Technologies) was added. After incubation at 37° C. for 10-20 minutes, cell colonies were dissociated into single cells by pipetting. Cells were then washed, embedded in fresh Matrigel and plated into 24-well plates. Cells cultured in the CV condition were passaged every 6 days at a 1:20 split ratio. Approximately half of the cultured crypts contained GFP+ cells, which is consistent with the in vivo GFP expression of Lgr5-GFP mice (FIG. 1).

Figure 2A:
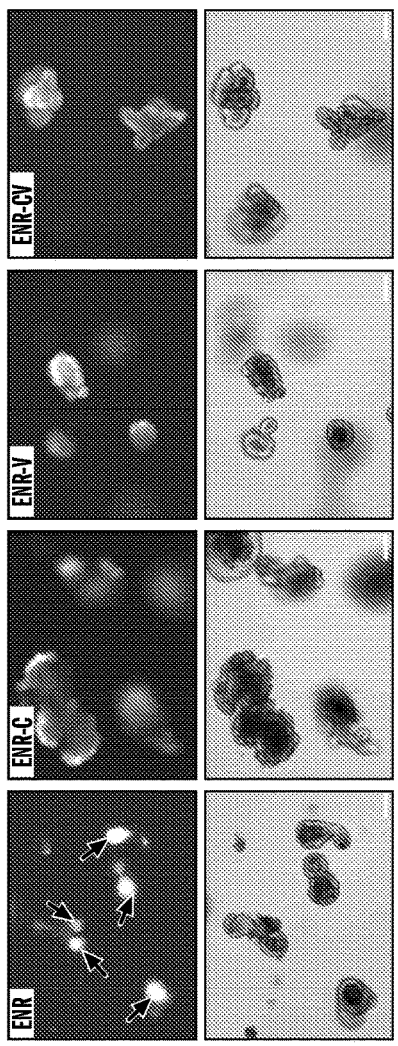
FIGS. 2A-2H show the combination of CHIR and VPA promoting the proliferation and self-renewal of Lgr5+ Stem Cells.
Figure 2B:
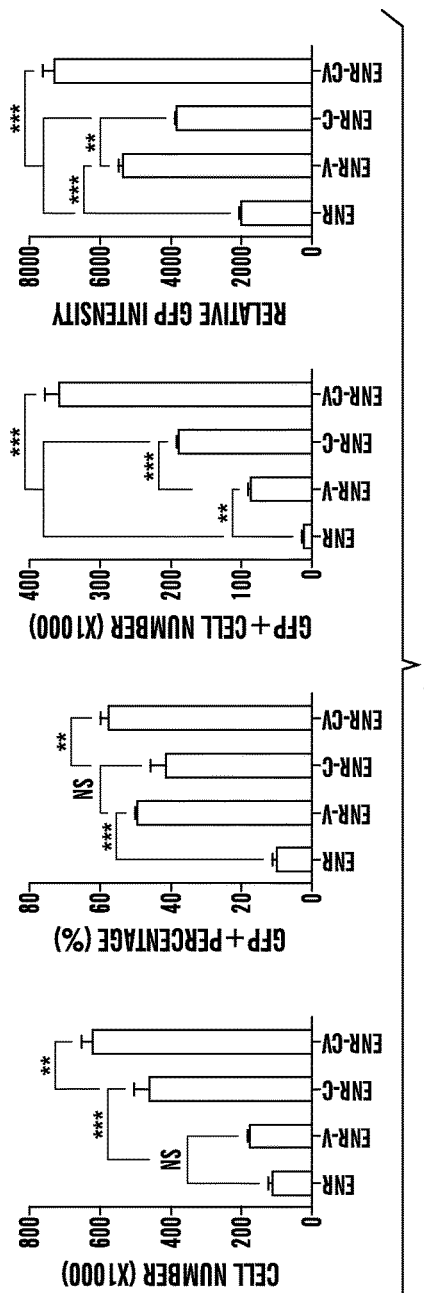
Figure 2C:
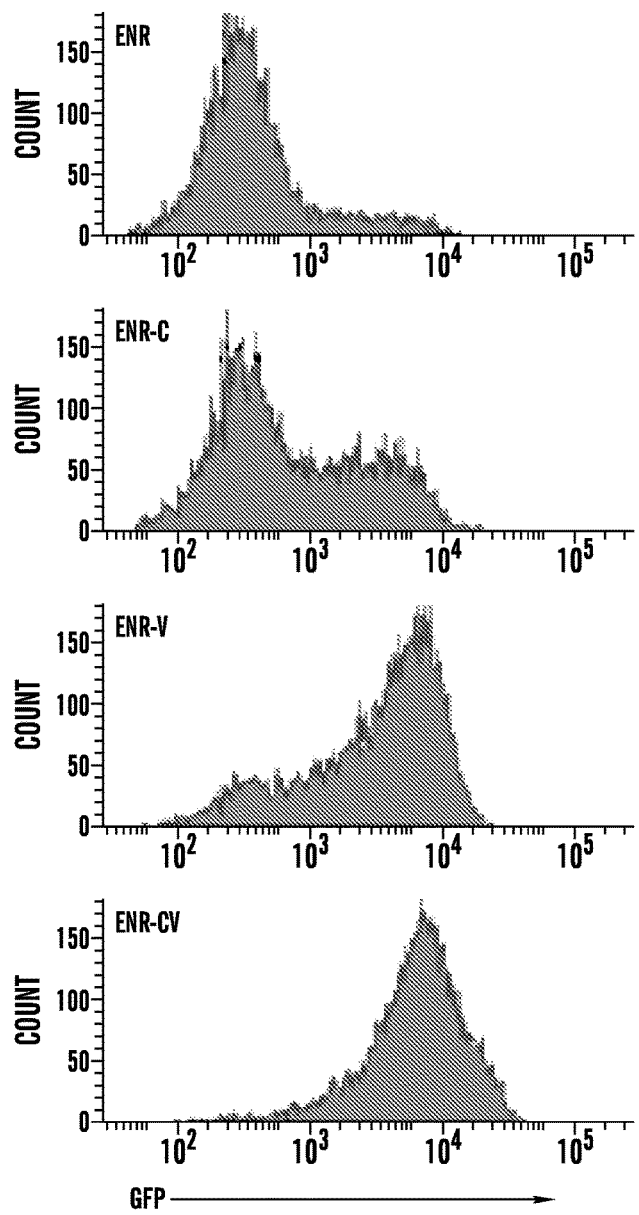
Figure 2D:
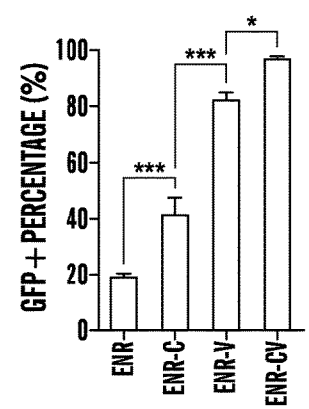
Figure 2E:
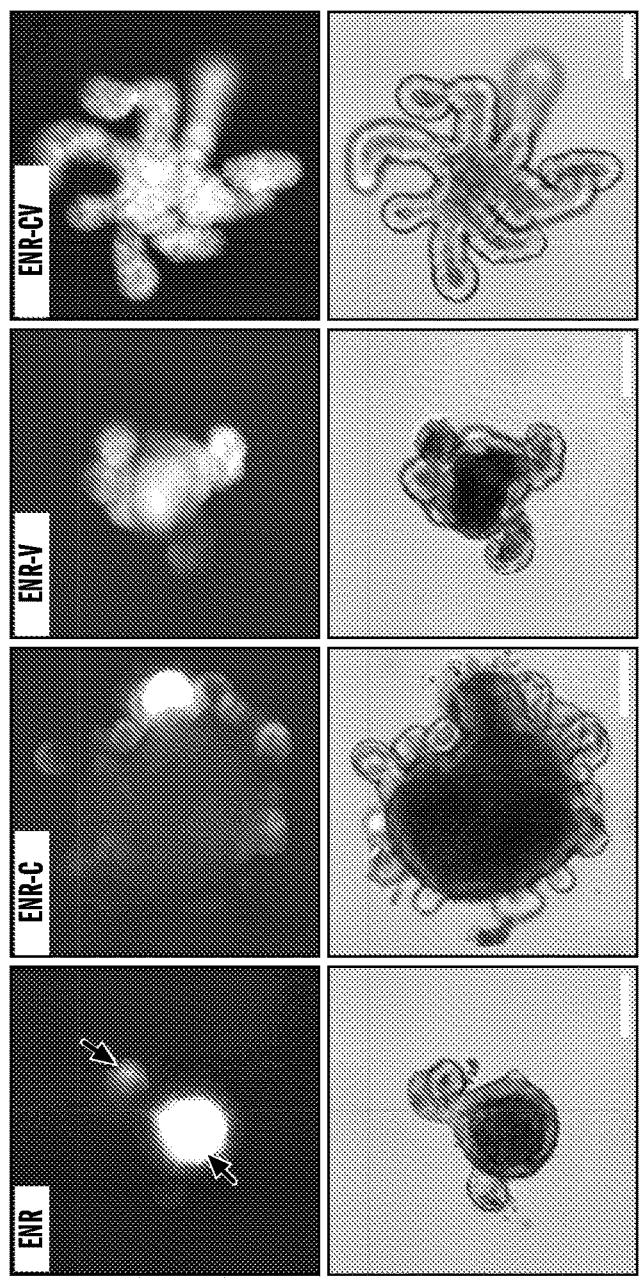

The growth factors used in the ENR condition provide essential, but not adequate cues to sustain the self-renewal of Lgr5+ stem cells. To identify factors essential to maintaining the self-renewal status of intestinal stem cells, selected small molecules that modulate signaling pathways of ISCs, such as Wnt, Notch, and BMP, were tested under the ENR condition, using the Lgr5-GFP reporter. CHIR99021 (referred to herein as CHIR or C), a GSK3β inhibitor which activates the Wnt signaling pathway, promoted the proliferation of crypt cells, as indicated by quantifying the average size of organoids and cell numbers in the culture (FIGS. 2A, 2B and 3A, 3B). CHIR increased the percentage and relative GFP intensity of GFP+ cells in the culture, indicating increased self-renewal of stem cells (FIGS. 2A and 2B). Notably, a large number of GFP negative cells still existed in the organoids (FIG. 2A), which was likely the result of insufficient maintenance of stem cell self-renewal or the result of promoting the proliferation of more mature GFP negative cells in the crypts. Valproic Acid (VPA or V), a histone deacetylase inhibitor, also significantly increased the GFP expression of GFP+ organoids, with minimal presence of GFP negative cells (FIG. 2A). Interestingly, when CHIR and VPA were combined (CV), cell proliferation as well as the percentage and relative GFP intensity of GFP expressing cells in the culture significantly increased (FIGS. 2A and 2B), with nearly pure GFP+ cells in GFP+ organoids (FIG. 2A), indicating minimal differentiation or proliferation of differentiated cells and increased self-renewal of stem cells in this culture condition.

Figure 3B:
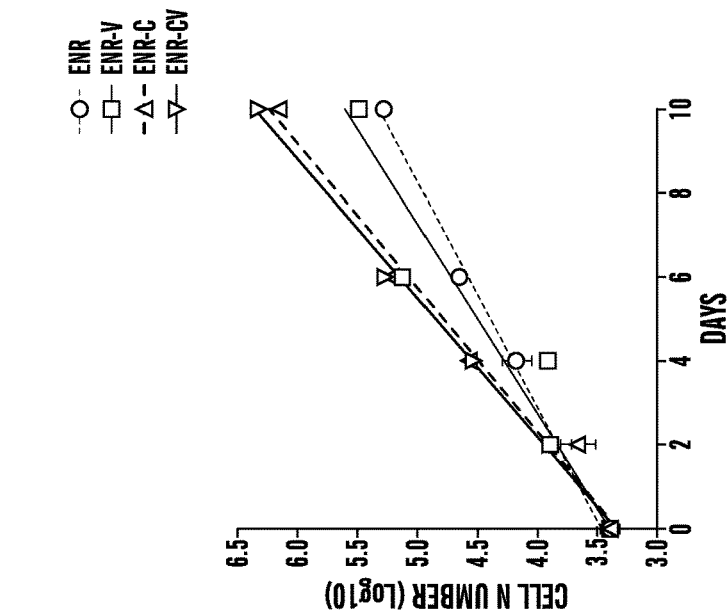
Figure 3A:
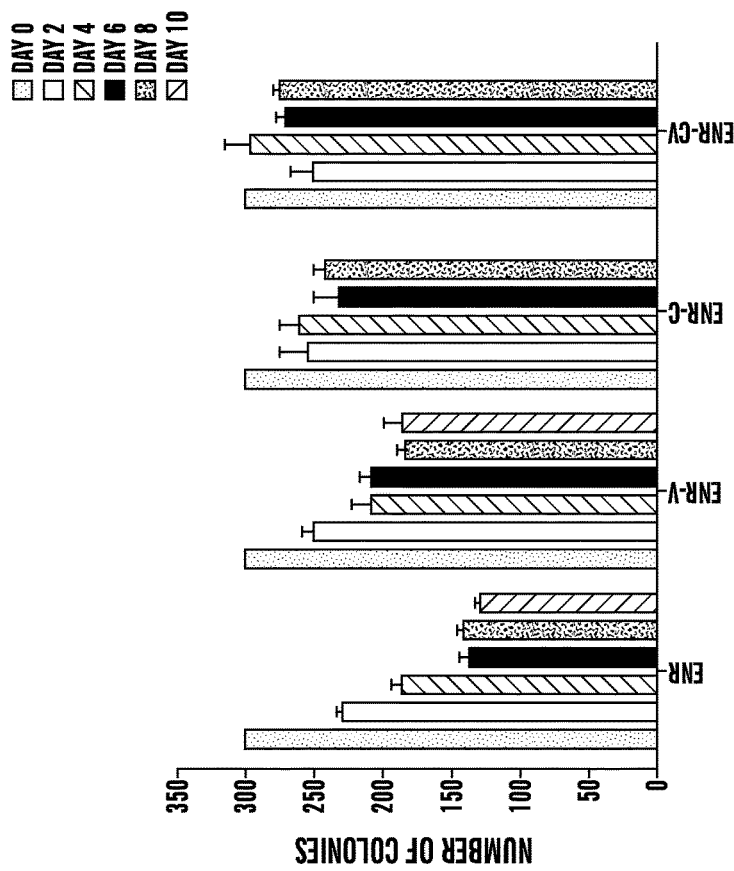
Figure 3E:
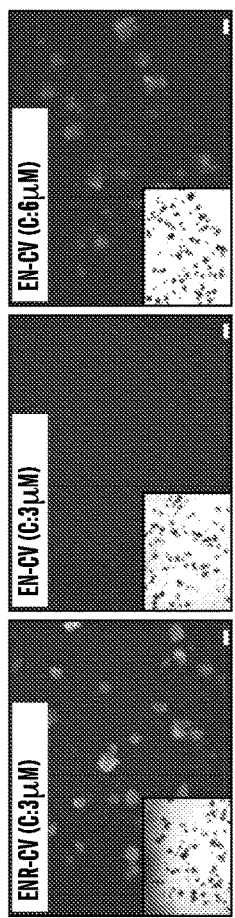
Figure 3G:
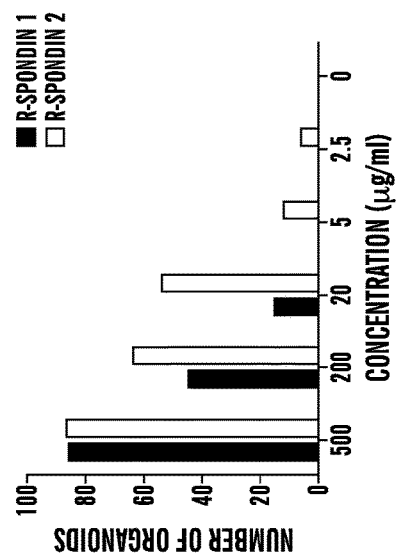
Figure 3F:
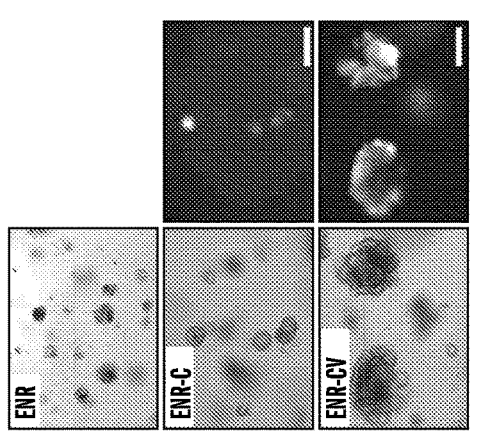
Figure 4A:
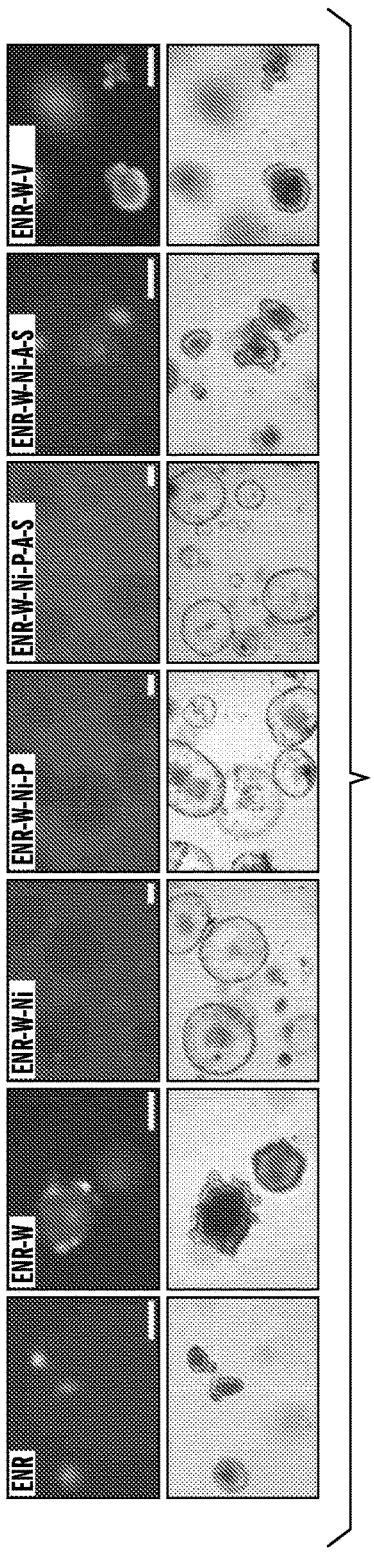
FIGS. 4A-4B depict testing of multiple culture conditions for EPHB2+ human colonic stem cells. Crypts were cultured for 6 days in multiple conditions as indicated. GFP and brightfield images are shown in FIG. 4A. W: Wnt3a (100 ng/ml); Ni: Nicotinamide (10 mM); P: PGE2 (0.02 µM); A: A-83-01 (0.5 µM); S: SB202190 (10 µM); V: Valproic Acid or VPA (1 mM). The EGF, Noggin, R-spondin 1, Wnt3a and VPA, or ENR-W-V, condition serves as a control to show increased expression of GFP. Scale bars: 200 µm.
Figure 4B:
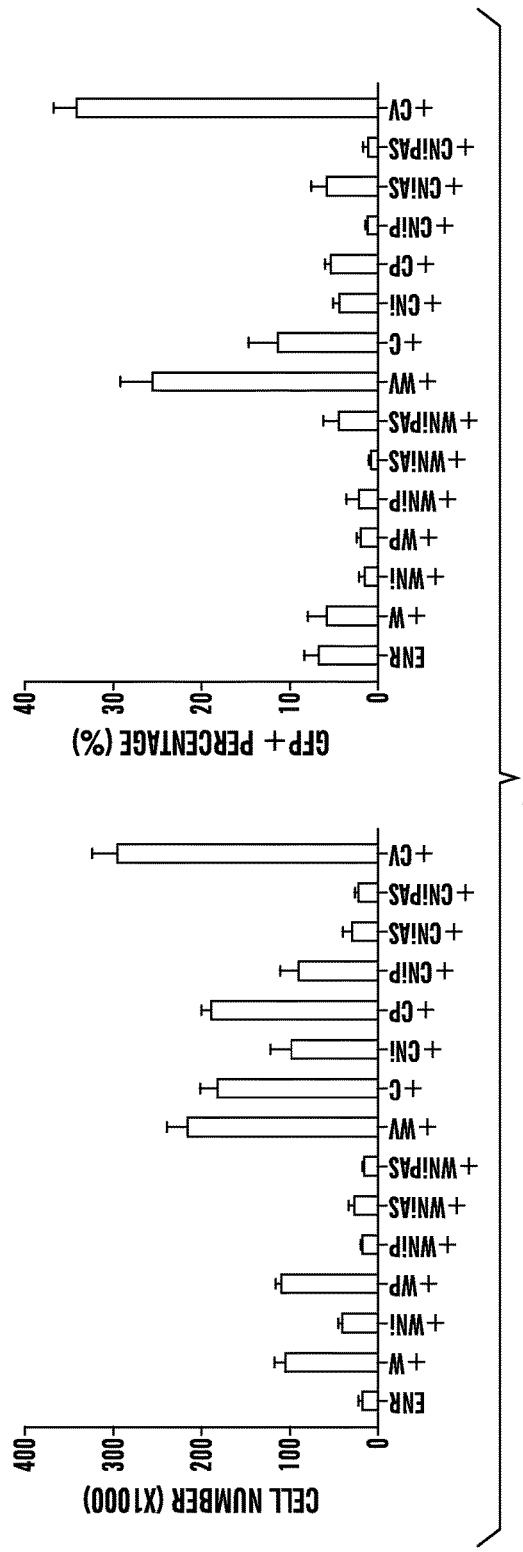

The GFP+ cells in the CV condition showed a single GFP-high population that corresponded to that of freshly isolated single cells (FIG. 3C), representing the Lgr5+ stem cell population as previously reported (Sato et al., 2009). Notably, in the CV condition, R-spondin 1 and Noggin were still required to maintain the self-renewal of Lgr5+ stem cells, while EGF promoted the proliferation of crypts, it could be removed from the culture without impacting maintenance of the Lgr5+ cells (FIG. 3D). Increasing the concentration of CHIR further eliminated the need of R-Spondin1 to promote GFP expression (FIG. 3E), consistent with the role of R-spondin 1 to increase Wnt/β-catenin signaling. Furthermore, VPA or CHIR+VPA also promoted GFP expression of Lgr5+ stem cells from the colon (FIG. 3F). In addition, R-Spondin 2 showed better efficacy at lower concentrations in promoting organoid formation in the ENR condition compared to R-spondin 1 (FIG. 3G). We also tested culture conditions that were previously shown to maintain human EPHB2+ colonic stem cells or colonic crypts in a largely undifferentiated state (Jung et al., 2011; Sato et al., 2011a) but failed to achieve similar effects on small intestinal Lgr5-GFP stem cells (FIGS. 4A and 4B), suggesting that these factors may act through different mechanisms on EPHB2+ colonic stem cells versus Lgr5+ stem cells.

To further confirm the proliferation and Lgr5+ self-renewal effects of CHIR and VPA in the absence of mature cell types and GFP negative stem cells (given that crypts show a mosaic GFP expression pattern), single GFP-high cells were isolated by FACS sorting (FIG. 3C) and cultured in Matrigel in the presence of ENR and CHIR or VPA, or in the presence of both compounds (CV condition). The Rho kinase inhibitor Y-27632, which inhibits anoikis of single stem cells (Watanabe et al., 2007), was added for the first two days as previously described (Sato et al., 2009). Following a 7 day culture, colonies containing GFP stem cells spontaneously formed. Similar to crypt cultures, CHIR significantly increased cell proliferation while it only moderately increased GFP expression, while VPA promoted GFP expression with a minimal pro-proliferative effect. For the CV condition, cell proliferation significantly increased and greater than 97% of the cells in the culture were GFP cells (FIGS. 2C-2E and 5A). It is noteworthy that compared to the crypt cultures, when pure single Lgr5+ stem cells were cultured in CHIR, the organoids that formed contained large numbers of GFP negative cells, indicating that stem cells differentiated in this condition and thus other factors were required to maintain the self-renewal status of Lgr5+ stem cells.

Figure 2H:
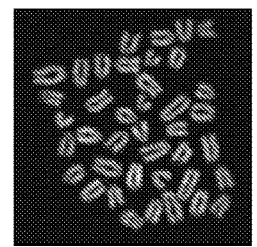

When isolated single Lgr5-GFP+ cells were cultured in the standard ENR condition, few cells grew into organoids, which is consistent with previous reports (Sato et al., 2009) and likely due to sub-optimal culture conditions. When CHIR was added to the culture (ENR-C), the colony-forming efficiency was significantly increased by 20-50 fold (FIGS. 2F, 2G and 5B, 5C), providing a similar response to the addition of Wnt3A when added at 100 ng/ml (FIG. 2F and Sato et al., 2011b). In sharp contrast to this, VPA only weakly increased colony-forming efficiency in the absence of CHIR (ENR-V, FIGS. 2F, 2G and 5B, 5C). Surprisingly, when isolated single Lgr5-GFP+ stem cells were cultured in the presence of both CHIR and VPA, there was a synergistic effect and ~25%-40% of the total cell population grew into colonies (FIG. 2F). This is believed to represent the most efficient colony formation that has been reported for Lgr5+ stem cells.

TABLE 1

Figure 2G:
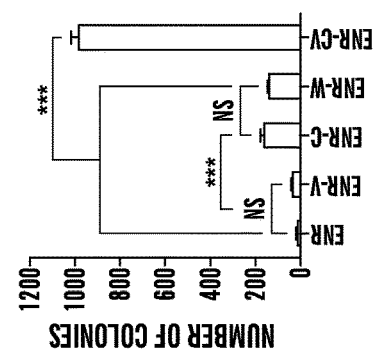
Figure 2F:
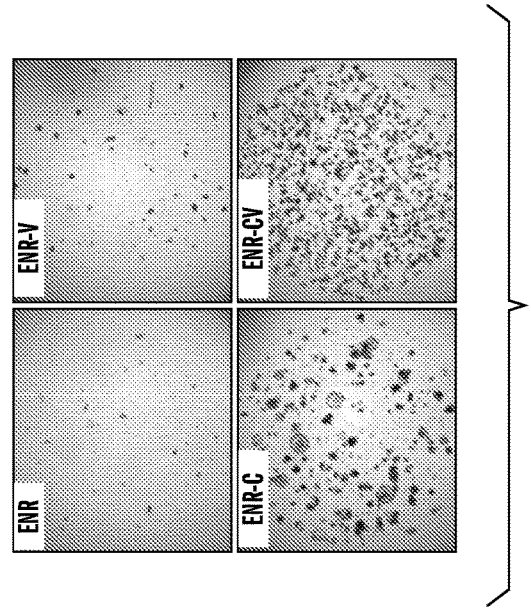

Colony Numbers for Colony Formation in FIG. 2G

|  | ENR | ENR--C | ENR-V | ENR-CV | ENR-W | ENR-WV |
|---|---|---|---|---|---|---|
| Average | 7.333333 | 158.6667 | 32.33333 | 956 | 135.3333 | 475.3333 |

TABLE 2

Figure 5A:
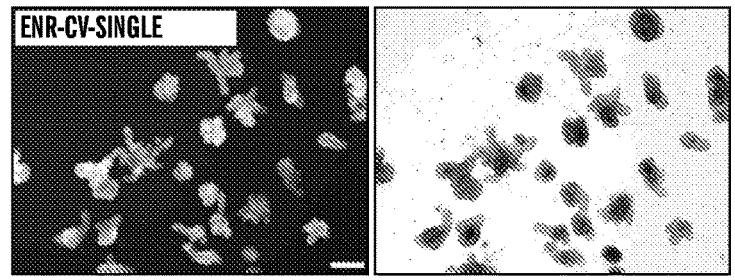
FIGS. 5A-5D depicts culture of single Lgr5-GFP stem cells.
Figure 5B:
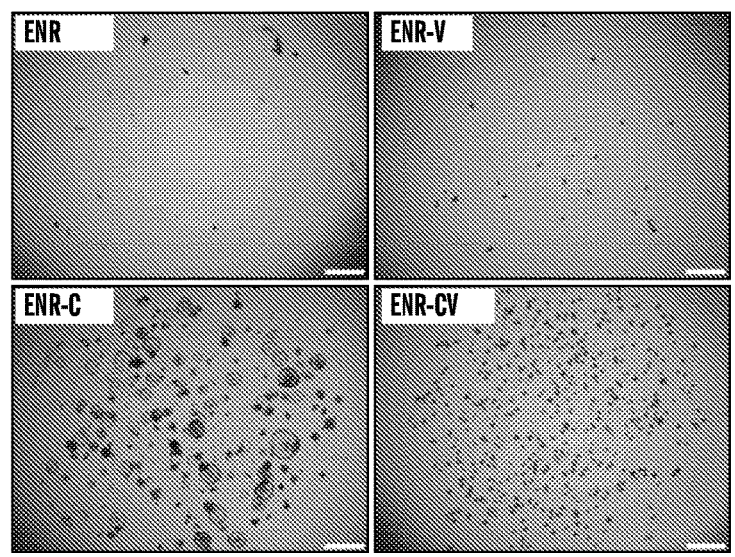
Figure 5C:
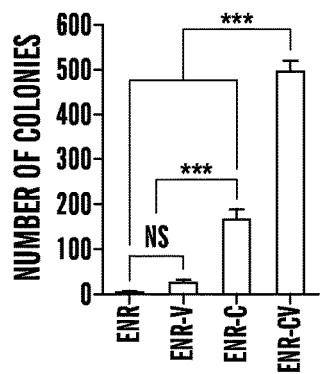

Colony Numbers for Colony Formation Efficiency in FIG. 5C

|  | ENR | ENR-C | ENR-W | ENR-V | ENR-CV |
|---|---|---|---|---|---|
| Average | 3 | 164.75 | 56.25 | 24.5 | 495.25 |

Given that a portion of the cells that were sorted via FACS were under a pro-apoptotic status and typically died within 12 hours (Sato et al., 2011b), live cells were manually counted 12 hours after seeding. Greater than 90% of the live cells grew into organoids when both CHIR and VPA were present in the culture media (FIG. 5D).

TABLE 3

Figure 5D:
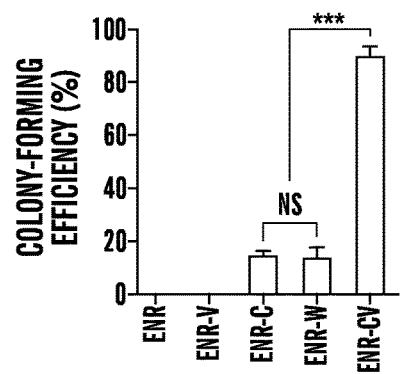

Colony Forming Efficiency in FIG. 5D

|  | ENR | ENR-V | ENR-C | ENR-CV | ENR-W | ENR-WV |
|---|---|---|---|---|---|---|
| Average | 0 | 0 | 0.142291 | 0.921154 | 0.132576 | 0.190111 |

Note:
<100 cells were plated so the calculated efficiency for R or RV is 0

Furthermore, cells cultured in the CV condition could be passaged as single cells for more than 10 passages with similar colony-forming efficiency with that of freshly isolated Lgr5-GFP+ cells, and without loss of proliferative ability, and they showed normal karyotype (2n=40) (FIG. 2H). These results suggest that CHIR and VPA provide signals that are not present in the standard ENR condition to maintain the self-renewal of Lgr5+ stem cells.

Figure 6A:
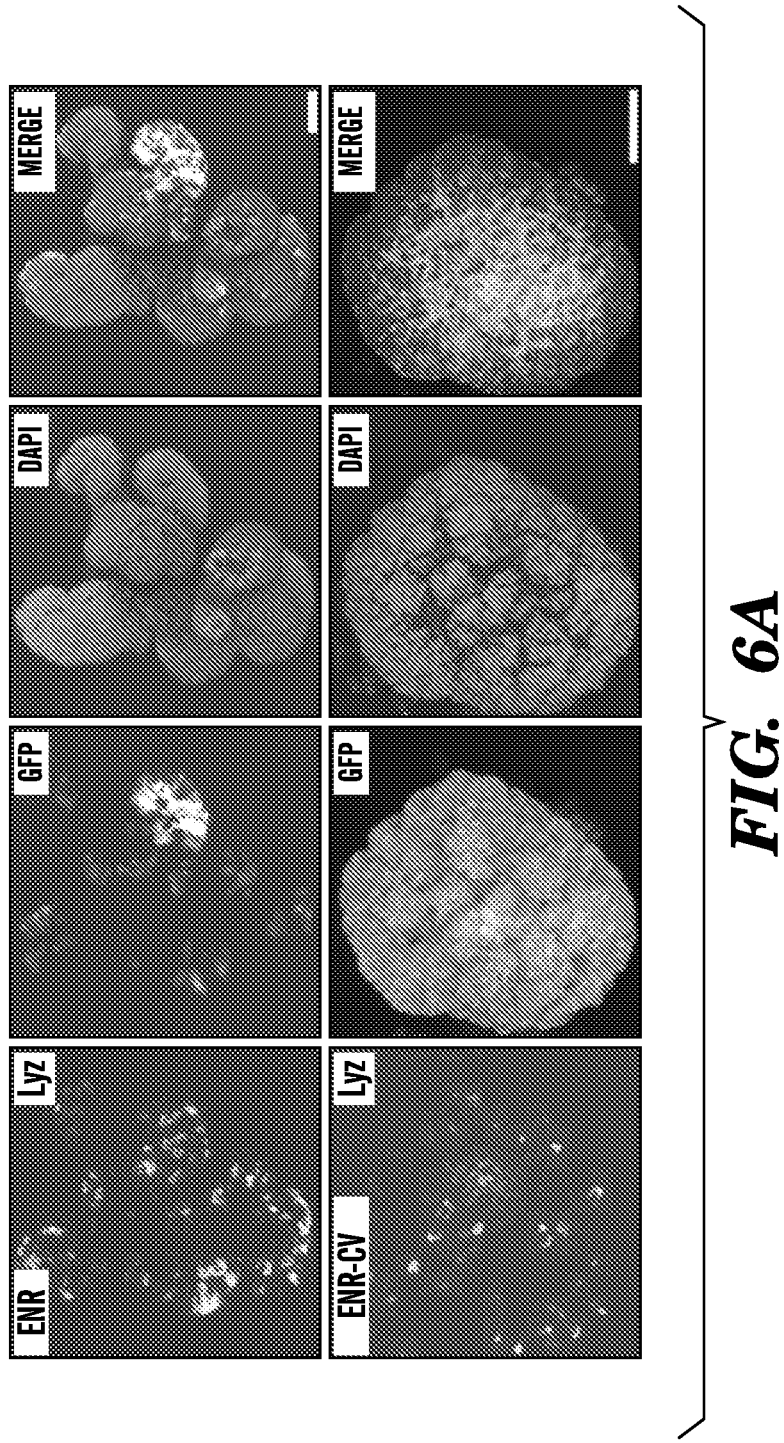
FIGS. 6A-6D depict maintenance of Lgr5+ stem cell self-renewal by the combination of CHIR and VPA. Confocal images of Lysozyme (FIG. 6A), Ki67 (FIG. 6B) and EdU (FIG. 6C) staining of organoids cultured under the ENR condition (Upper panels) and colonies cultured in the ENR-CV condition (Lower panels) are shown. For EdU staining, cells were cultured with the thymidine analogue EdU (red) for 1 hour.
Figure 6B:
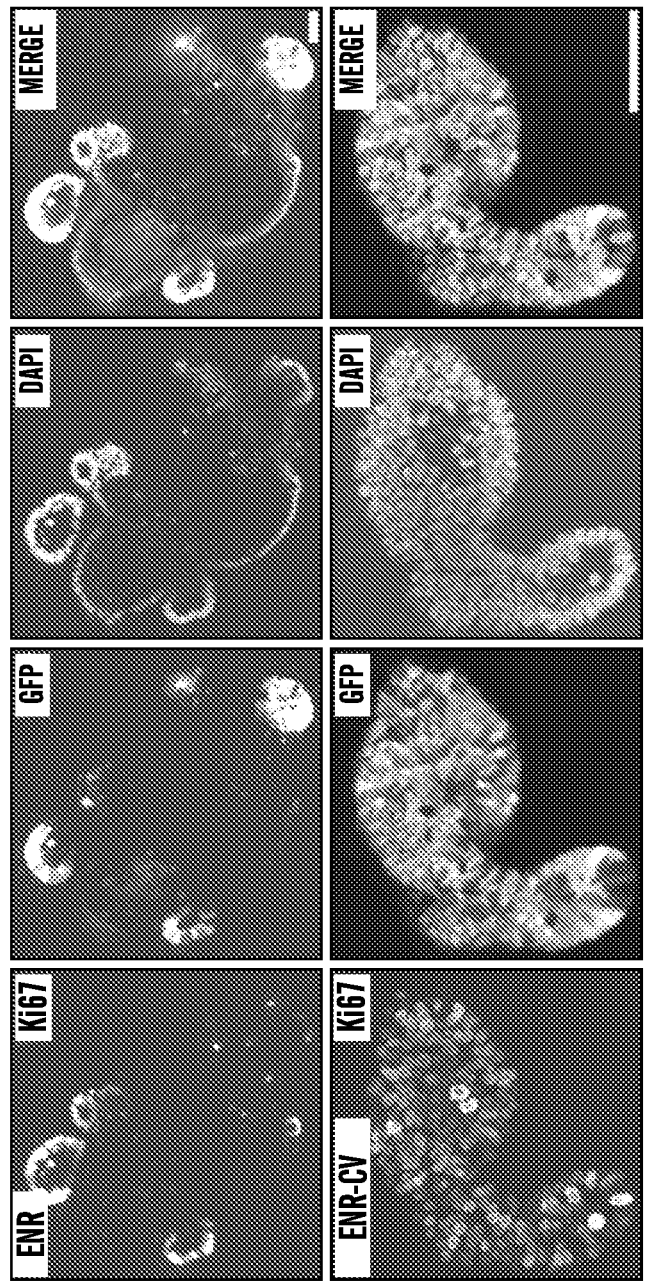
Figure 6D:
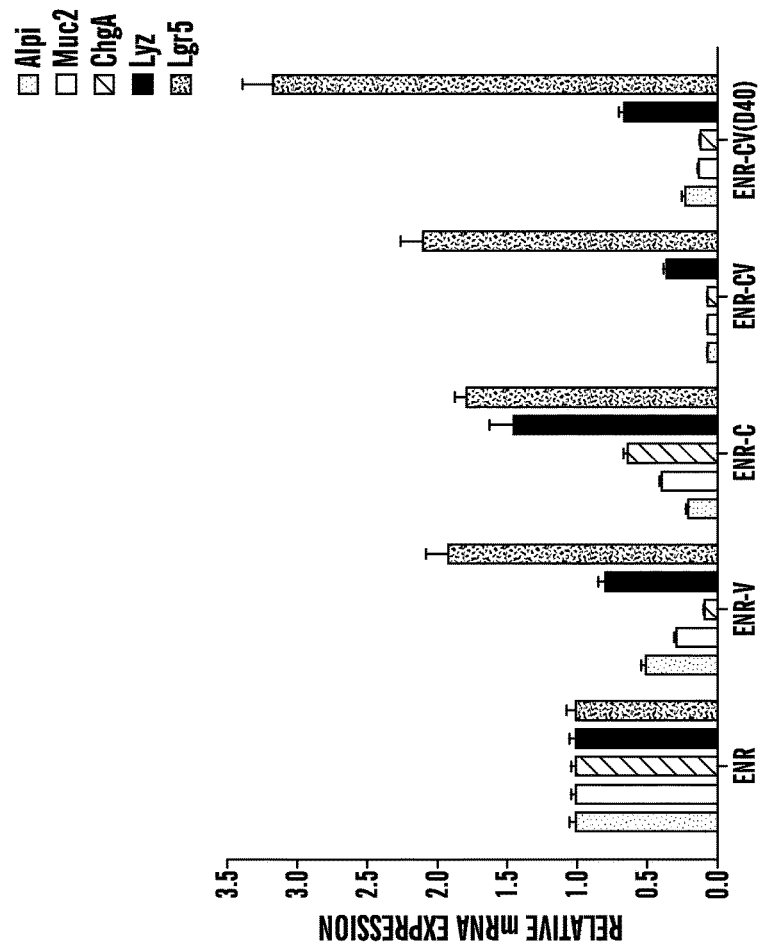
Figure 6C:
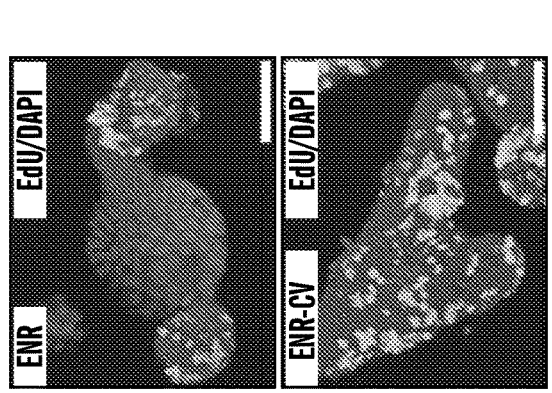
Figure 7A:
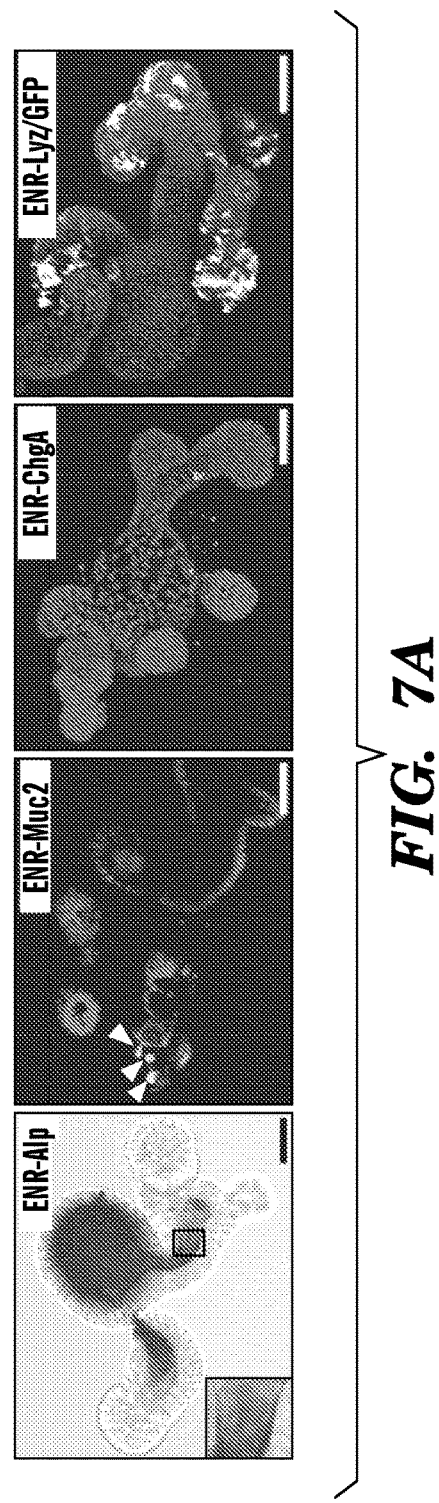
FIGS. 7A-7D depict differentiation of intestinal stem cells cultured under CV Condition.

As previously reported, cells in the ENR condition grew into organoids with crypt-villus structure containing all intestinal epithelial cell types, confirmed by staining of alkaline phosphatase (Alp) positive enterocytes, Mucin 2 (Muc2) positive goblet cells, Chromogranin A (ChgA) positive enteroendocrine cells, Lysozyme (Lyz) positive Paneth cells and Lgr5-GFP+ stem cells. Lgr5+ stem cells only reside at the tips of crypt (FIGS. 6A and 7A). Ki67 and EdU staining revealed that proliferating cells were only existent within the crypt domains (FIGS. 6B and 6C). In the CV condition, however, GFP+ stem cells were present throughout the entire colony with minimal presence of Paneth cells (FIG. 6A) and without the presence of other cells types. Compared to ENR culture, Ki67 or EdU positive proliferating cells in the CV condition existed throughout the cell colony (FIGS. 6B and 6C). This was confirmed with quantitative Real-time PCR whereby cells in the CV condition expressed minimal levels of Alpi (enterocytes), Muc2 (goblet cells), ChgA (enteroendocrine cells), moderate levels of Lysozyme (Paneth cells) and high levels of Lgr5 (ISC) compared to cells in the ENR condition (FIG. 6D). This expression pattern was maintained over multiple passages, and the Lgr5 expression level was maintained (FIG. 6D).

CHIR alone reduces enterocyte differentiation, but simultaneously increased Paneth cell differentiation (FIG. 6D), which is consistent with previous report (Farin et al., 2012). While VPA alone decreased secretory differentiation (FIG. 6D) and helped to maintain a higher fraction of GFP+ stem cells, it is not sufficient to suppress the differentiation of stem cells. Indeed, when isolated single stem cells were cultured in the presence of VPA but without CHIR or other agents that promote Wnt signaling, their survival was much lower than when Wnt was present. When the Wnt pathway is blocked by IWP-2, VPA alone cannot maintain the self-renewal of stem cells (the IV condition in FIGS. 7B, 7C). The combination of CHIR and VPA suppressed both enterocyte and secretory differentiation and maintained the self-renewal program of Lgr5+ stem cells (FIG. 6D). These results suggest CHIR or VPA alone is not sufficient to maintain the self-renewal of Lgr5+ stem cells, but shows synergetic effects when combined with CHIR or other Wnt activators.

In summary, two small molecules, CHIR and VPA, can support Lgr5+ stem cell self-renewal without direct contact with, or in the absence of, Paneth cells. In particular, these small molecules can greatly improve colony formation from single stem cells, indicating that they provide essential niche signals that are typically provided by Paneth cells.

Figure 7B:
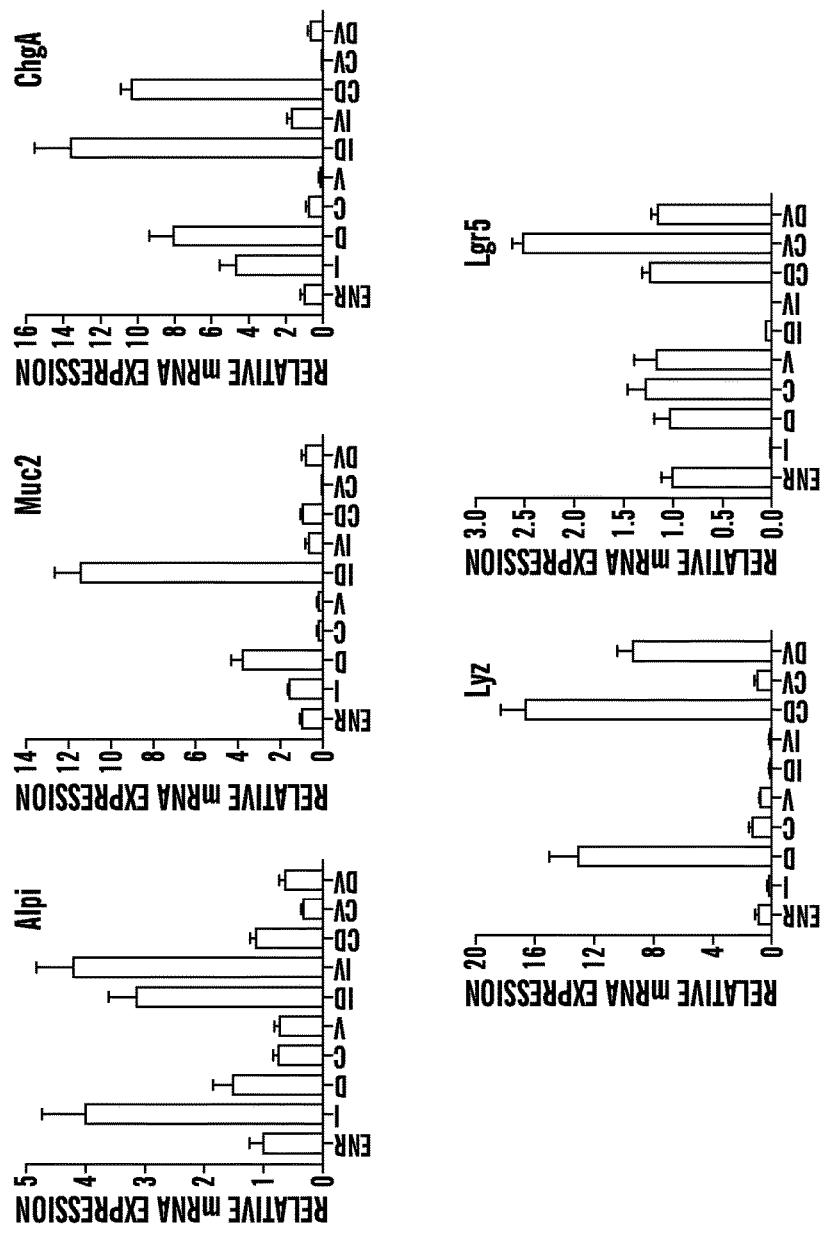
Figure 8A:
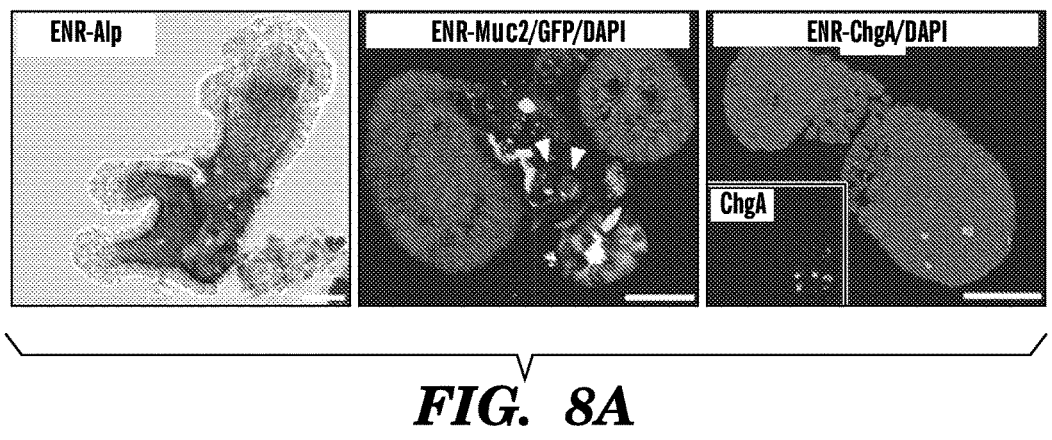
FIGS. 8A-8F depict controlled differentiation of Lgr5+ stem cells in vitro.

Example 2: Lgr5+ Stem Cells Remain Multipotent Following Culture in CHIR and VPA Intestinal stem cells have the ability to self-renew as well as differentiate into all cell types in the intestine epithelium, including the four major cell types: enterocytes, goblet cells, enteroendocrine cells and Paneth cells. To test the differentiation capability of Lgr5+ stem cells cultured in the CV condition, the cell colonies were transferred to the ENR condition that permits Lgr5+ stem cells to spontaneously differentiate into the mature cell types of the intestine. As expected, after withdrawal of CHIR and VPA, the morphology of organoids changed to the typical morphology of organoids cultured in ENR condition, with crypt-villus structure and Lgr5+ stem cells at crypt tips (FIGS. 7A and 8A). The mRNA expression of differentiation markers Alpi, Muc2, and ChgA elevated and cells expressed a similar level of Lysozyme (comparing ENR and CV in FIG. 7B). Immunocytochemistry staining for these markers confirmed the existence of differentiated cell types in the culture (FIG. 7A).

Example 3: Differentiation of Intestinal Stem Cells is Controlled

Figure 7C:
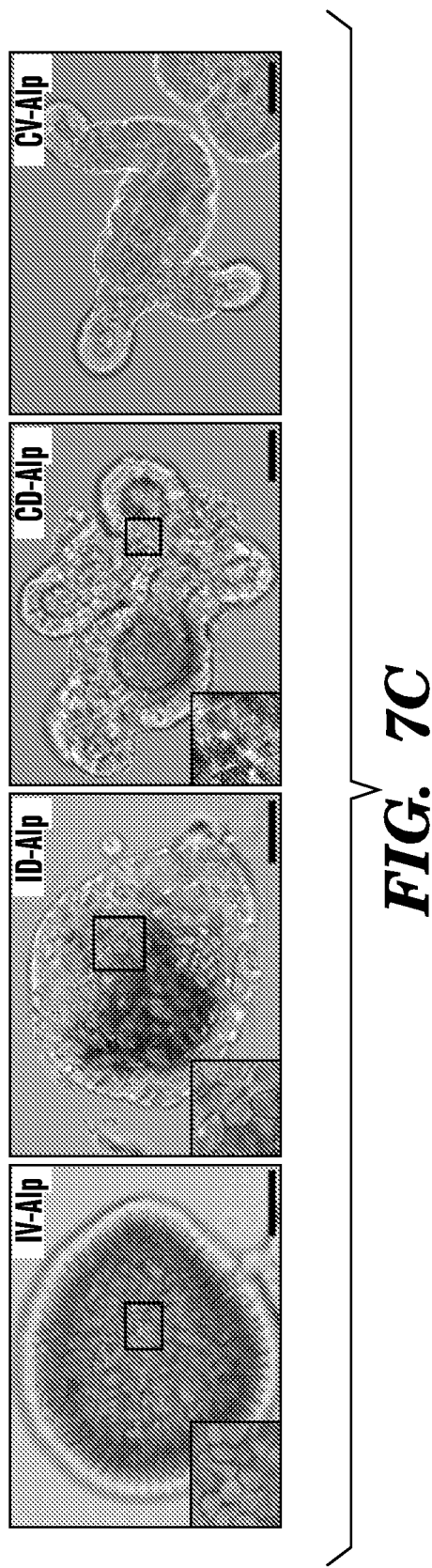
Figure 7D:
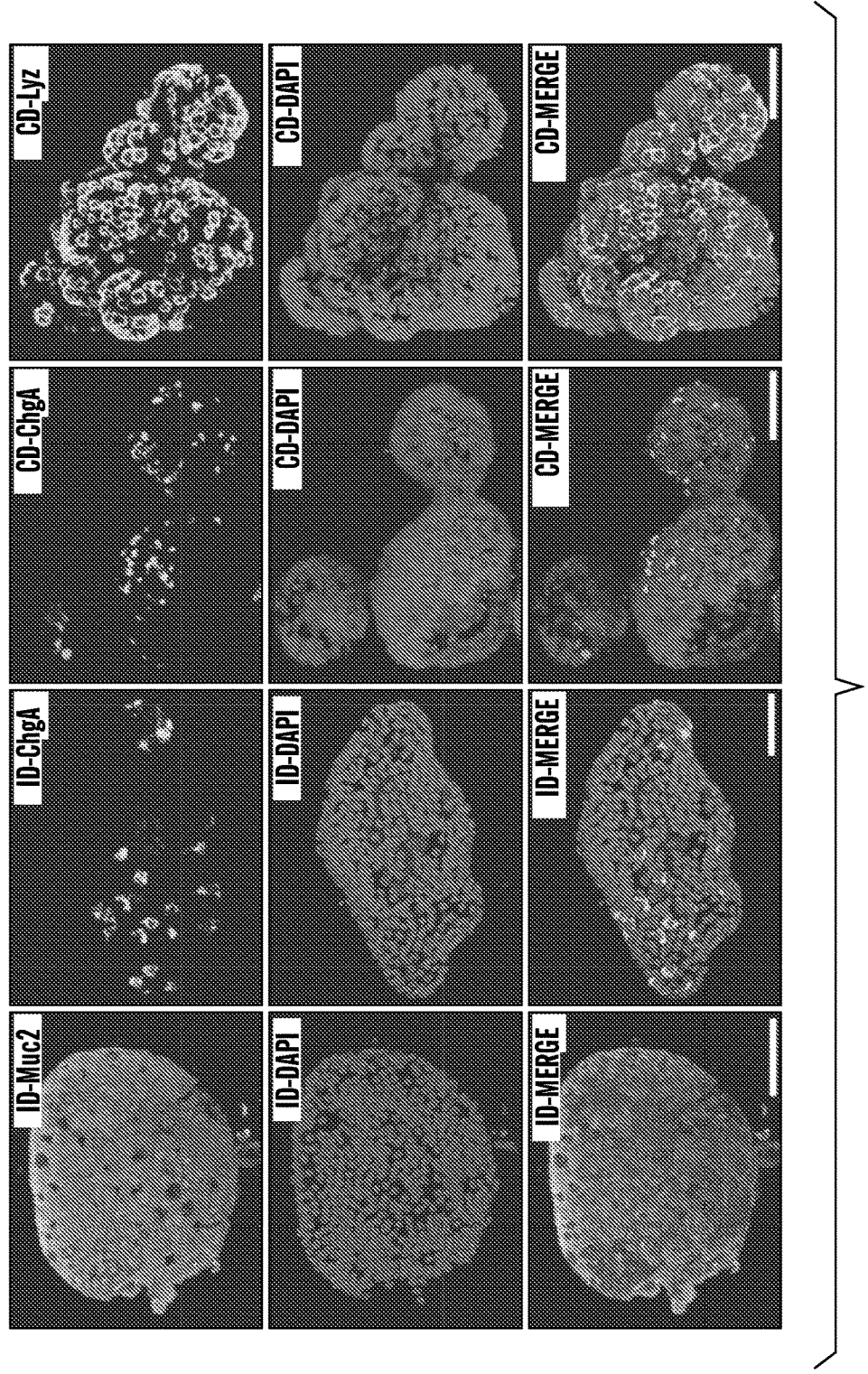
Figure 8B:
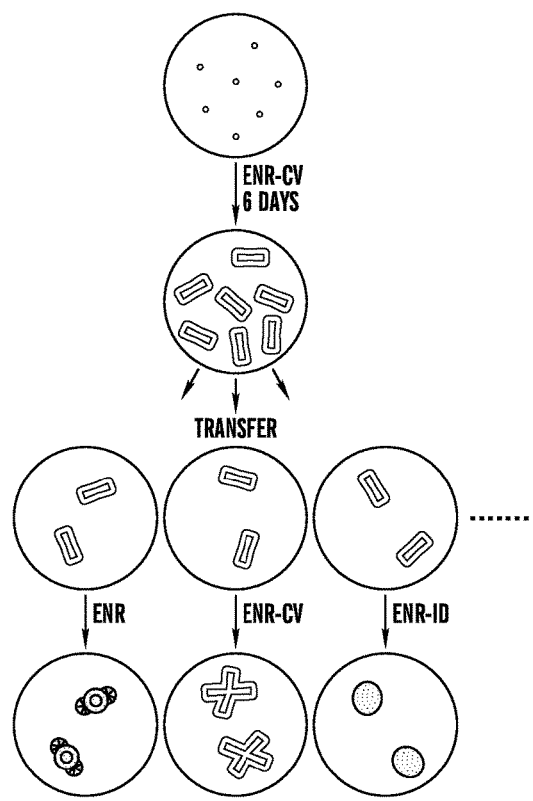
Figure 8D:
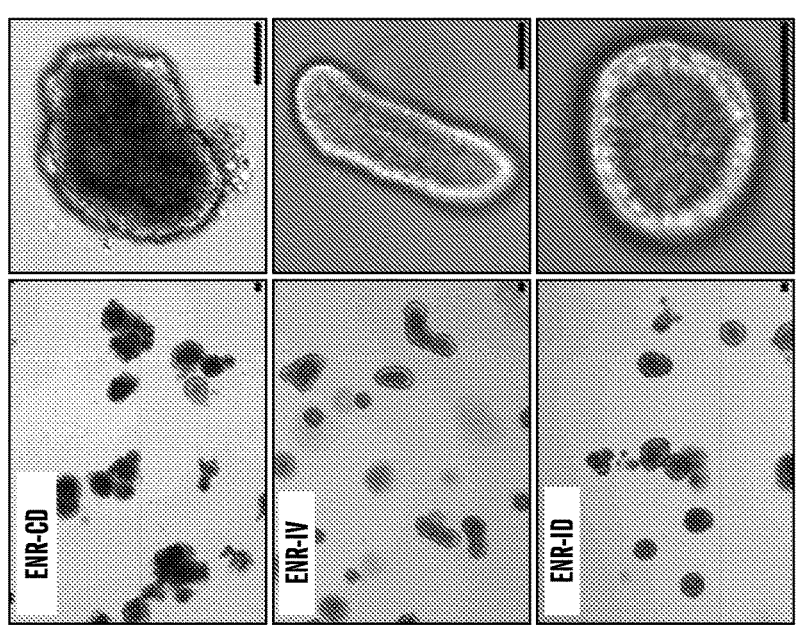
Figure 8C:
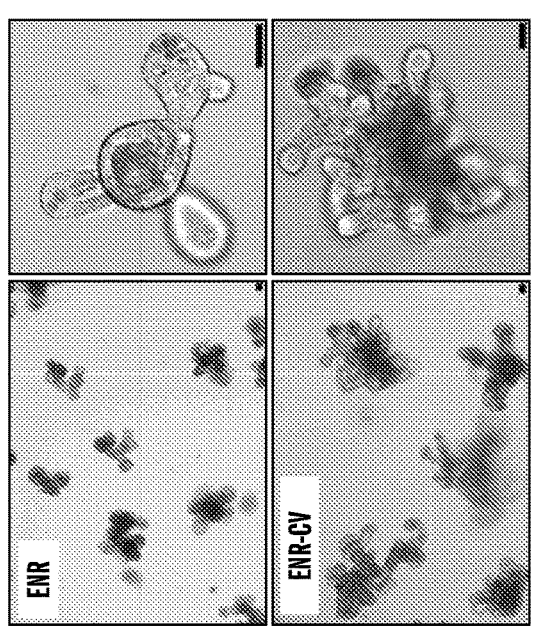
Figure 8E:
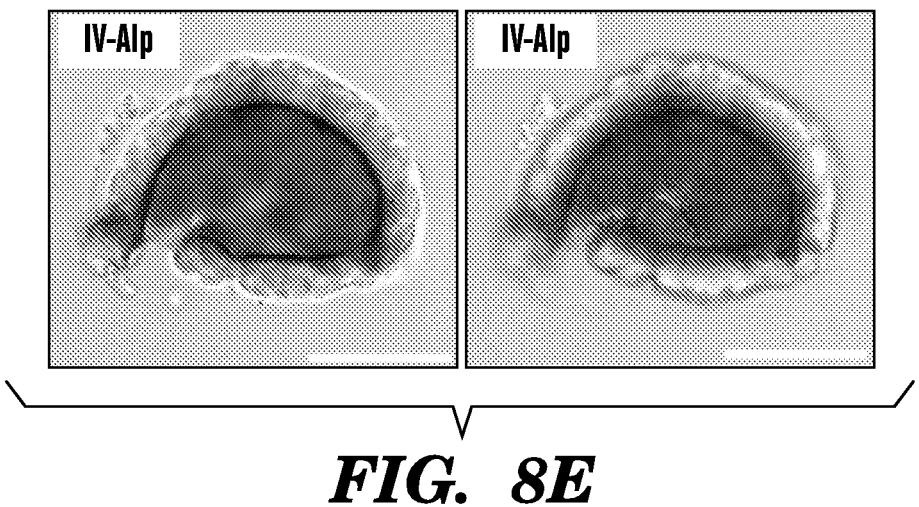
Figure 8F:
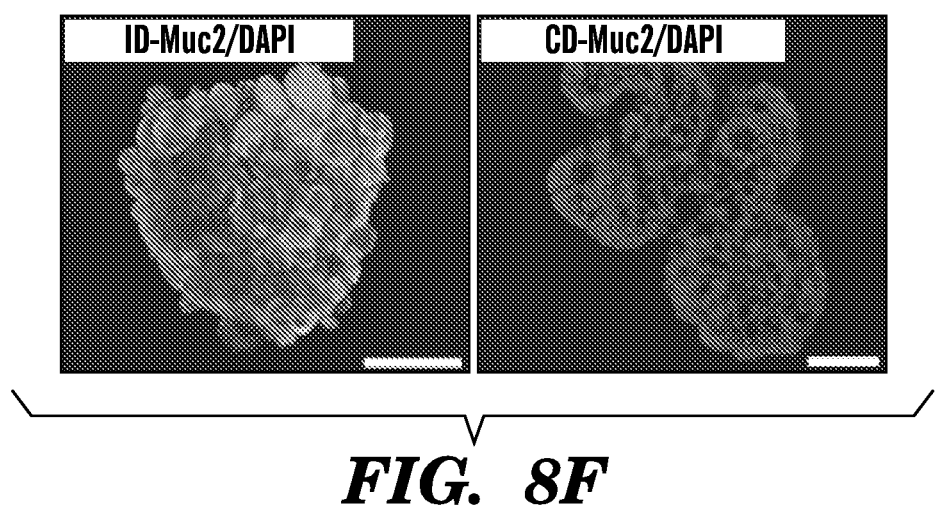

Next, with the ability to expand high purity Lgr5+ stem cells in vitro, directing the differentiation of Lgr5+ stem cells towards mature cell types was attempted. As Wnt and Notch are two of the main signaling pathways that control the differentiation of ISC, the Wnt pathway inhibitor IWP-2 (also I) and Notch inhibitor DAPT (also D) were used to induce the differentiation of cultured Lgr5+ stem cells. Because cells in the ENR condition spontaneously differentiate into organoids containing all epithelial cell types, ENR was included in the differentiation cultures. Following culture of single stem cells in the CV condition for 6 days, cell colonies were harvested and transferred into several wells and cultured in the presence of single or multiple inhibitors (FIG. 8B). As shown in FIG. 7B, replacing CV with IWP-2 or DAPT decreased ISC marker Lgr5 expression and induced expression of differentiation markers Alpi, Muc2, ChgA and Lysozyme. Notably, the presence of VPA (e.g. comparison between R and V, I and IV, C and CV, or D and DV) caused a lower level of expression of Muc2, ChgA and Lysozyme but not Alpi, indicating VPA specifically suppressed secretory cell lineage differentiation. Alternatively, Wnt inhibition with IWP-2 preferentially induced Alpi expression, with modestly elevated Muc2 and ChgA expression and completely abolished Lysozyme and Lgr5 expression. This indicates that Wnt signaling is required to maintain stemness and to suppress differentiation, yet is also required for Paneth cell differentiation. The Notch inhibitor DAPT greatly elevated markers of secretory cell types including Muc2, ChgA and Lysozyme, which is consistent with previous reports that Notch inhibition induces secretory cell differentiation (Milano et al., 2004; VanDussen et al., 2012; Wong et al., 2004). Furthermore, the combination of IWP-2 and VPA specifically induced enterocyte differentiation, presumably by combining the effects of both inhibitors, in which IWP-2 induced Lgr5+ stem cell differentiation while VPA suppressed the differentiation of Lgr5+ stem cells towards secretory cell types. Similarly, the combination of DAPT and CHIR mainly induced Paneth cell differentiation, and the combination of IWP-2 and DAPT primarily induced goblet cell differentiation. These conditions also induced clear morphological changes which resembled the morphology of each differentiated cell type (FIGS. 7C and 8D). Staining of enterocyte, goblet cell and Paneth cell markers confirmed the above observations (FIGS. 7C, 7D and 8E, 8F). The presence of IWP-2 or CHIR did not significantly influence ChgA expression, indicating that compared to goblet cells and Paneth cells, the differentiation of enteroendocrine cells does not strictly require Wnt inhibition or activation.

Example 4: The Mechanism Mediating the Response of CHIR and VPA is Examined

Figure 9A:
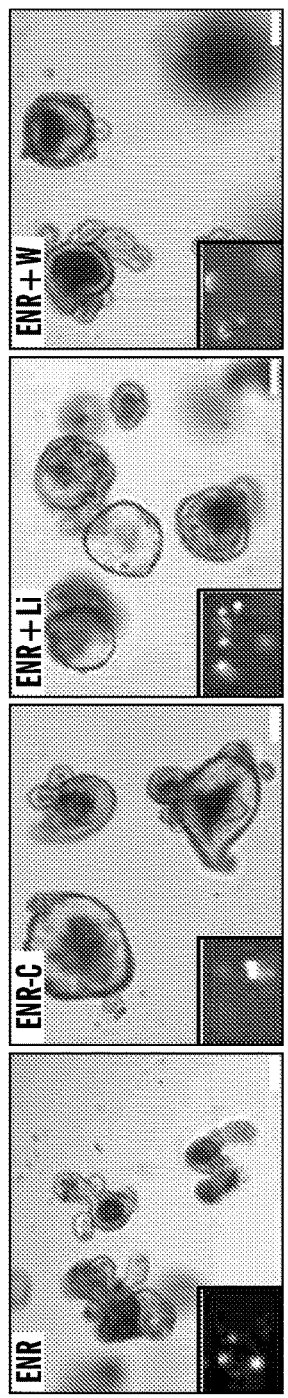
FIGS. 9A-9F depicts a Mechanism of Action for CHIR and VPA.
Figure 9B:
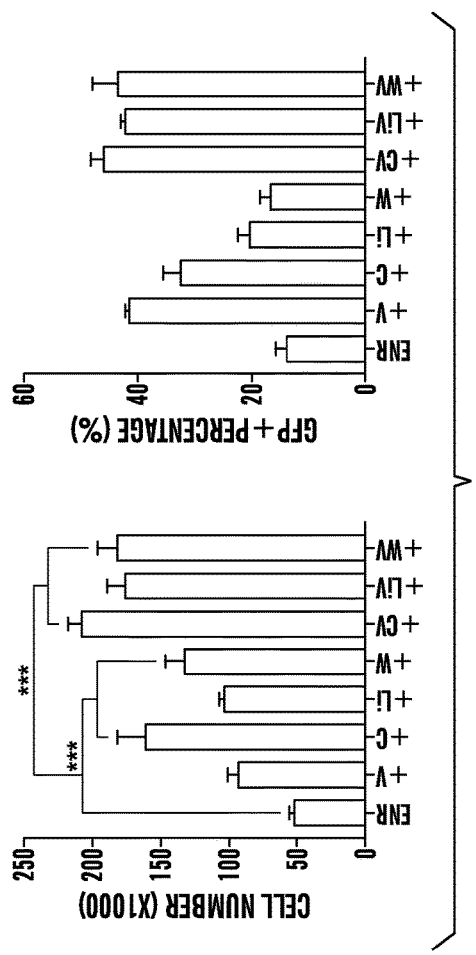
Figure 9C:
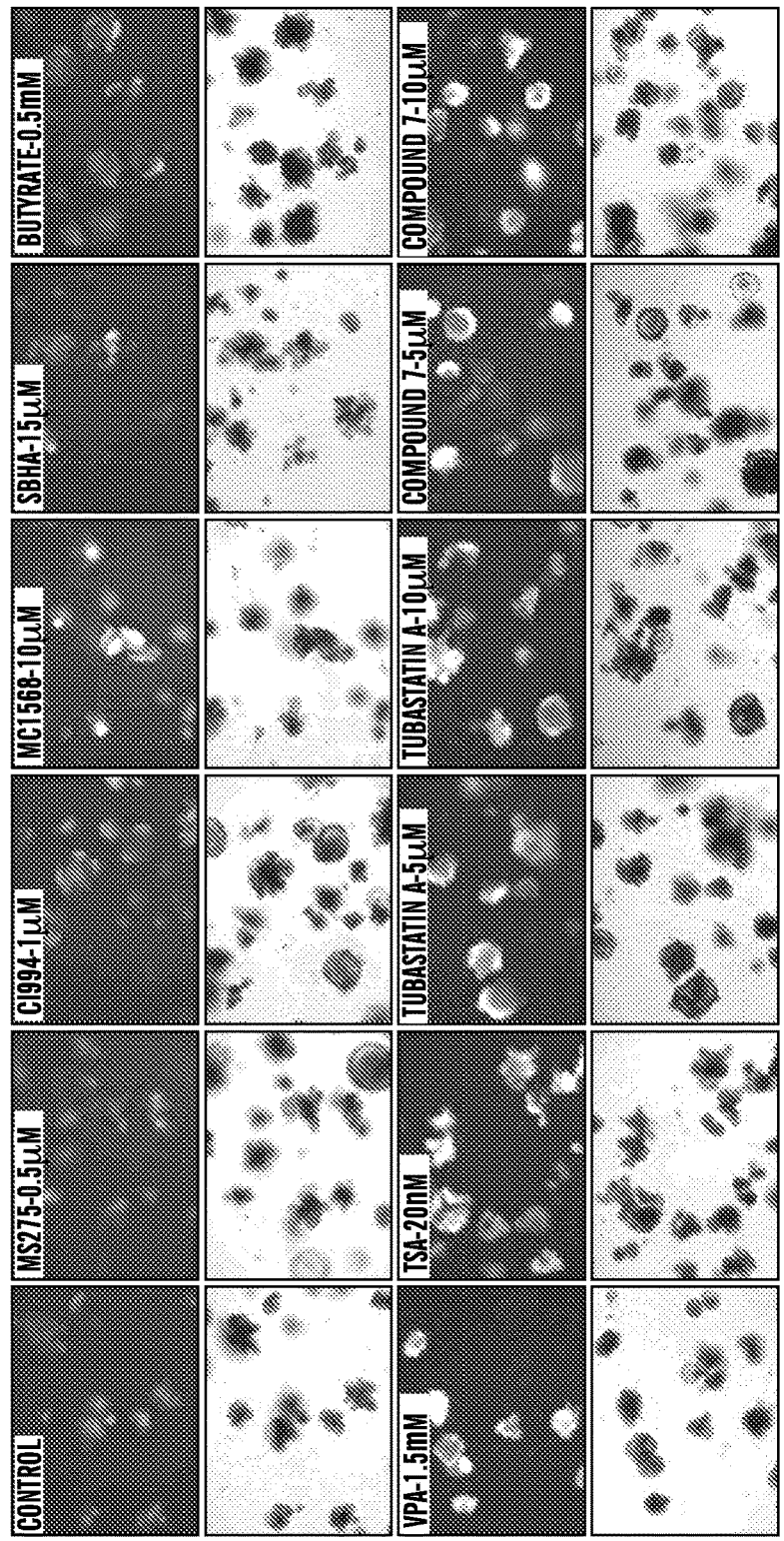
Figure 9D:
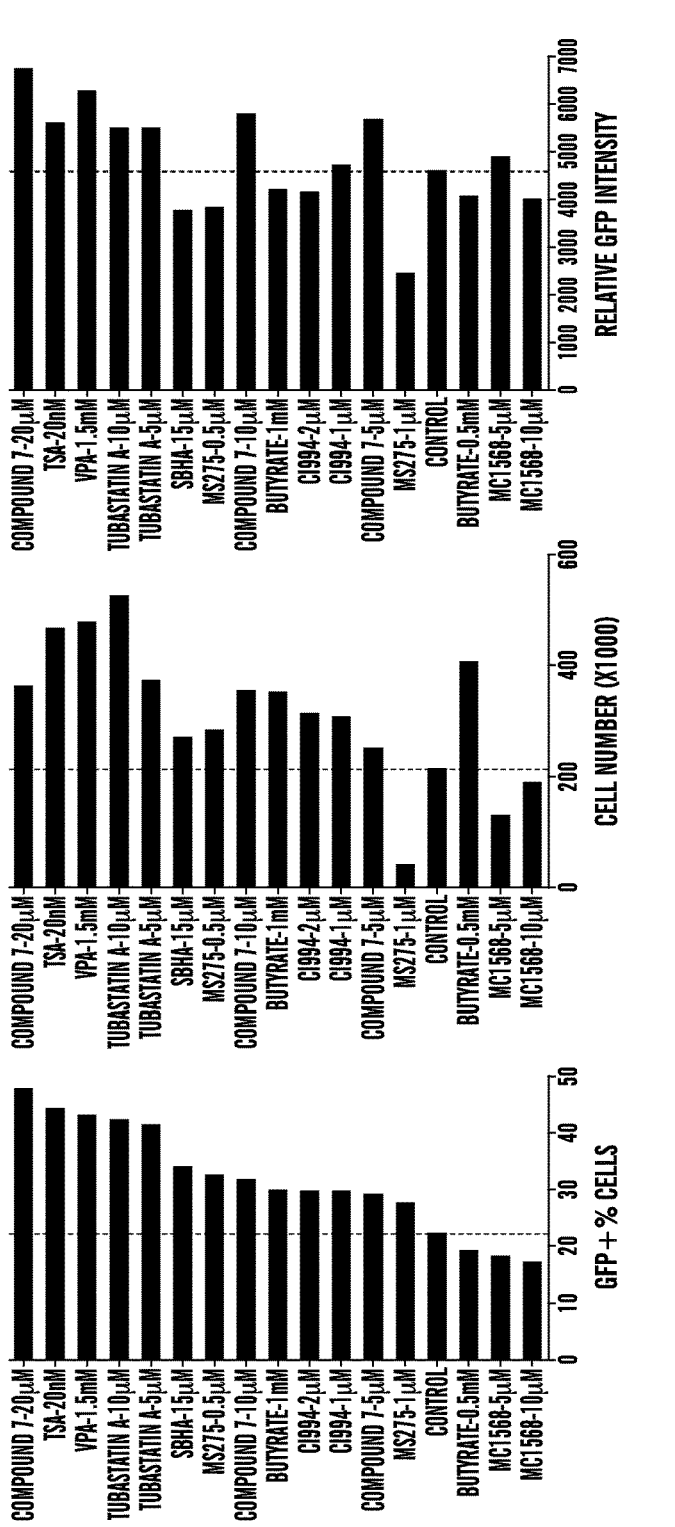
Figure 9E:
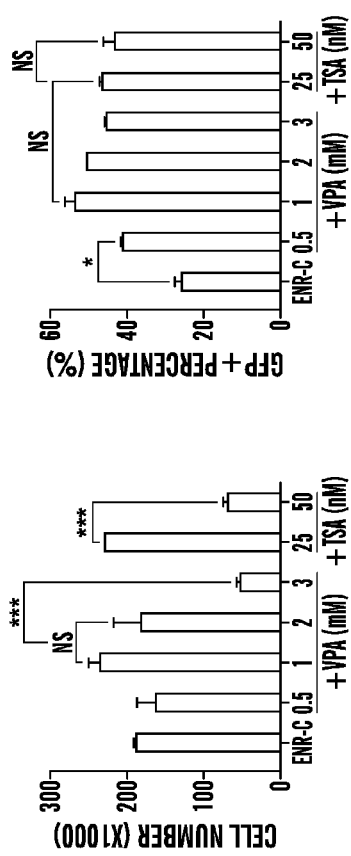
Figure 9F:
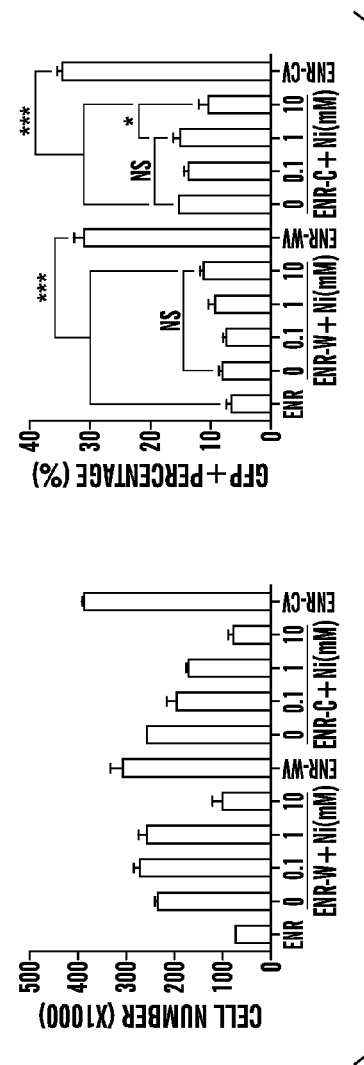
Figure 10:
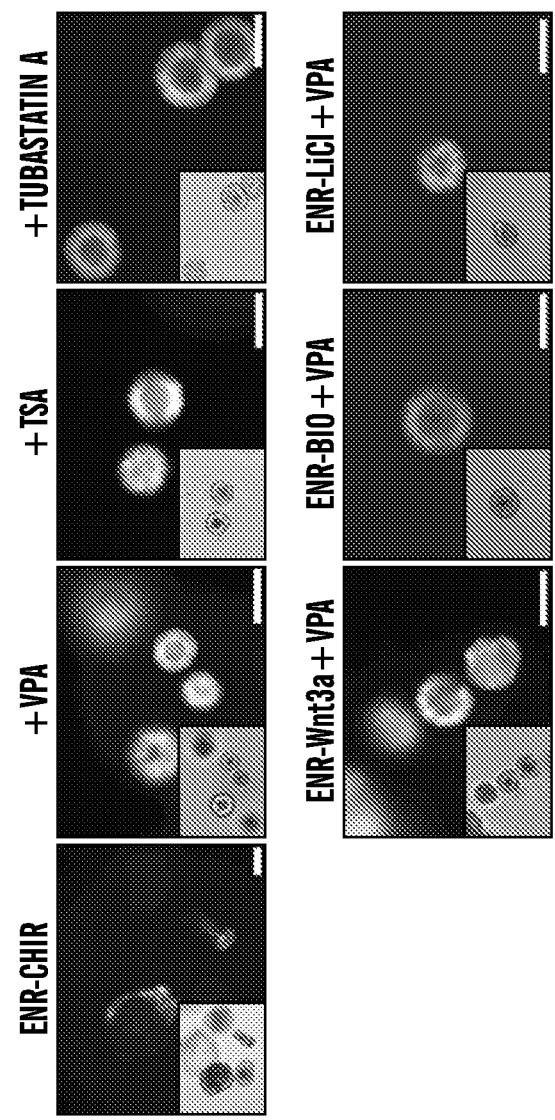
FIG. 10 depicts morphology and GFP expression of single Lgr5-GFP cells cultured in multiple conditions. Scale bars: 100 µm.

CHIR is a highly-specific GSK3 inhibitor that activates the Wnt/β-catenin signaling pathway (Bain et al., 2007), and has been used to maintain the self-renewal state of embryonic stem cells (Ying et al., 2008). To confirm that the effect of CHIR was through activating the Wnt pathway, the effects of other Wnt pathway activators were tested, including Lithium and Wnt3a. Replacing CHIR with LiCl or Wnt3a increased crypt proliferation, indicated by the increased colony size and cell numbers compared to the ENR condition (FIGS. 9A and 9B). Colonies in these conditions showed cyst-like structures (FIG. 9A) as shown previously (Sato et al., 2011b). Similarly, the effects of other HDAC inhibitors including pan-HDAC inhibitors and type-specific inhibitors were tested. pan-HDAC inhibitor TSA as well as HDAC6 specific inhibitor Tubastatin A and Compound 7 showed a similar effect of promoting GFP expression with VPA (FIGS. 9C and 9D). While other pan-HDAC inhibitors including SBHA and Butyrate, as well as class I (CI-994, MS275, FIGS. 9C and 9D), class IIa (MC1568, FIGS. 9C and 9D) and class III (Nicotinamide, FIG. 9F) HDAC inhibitors showed no or only moderate effects to promote GFP expression (FIG. 9C-9F). TSA and VPA showed marked proliferation inhibition effect at higher concentration, but maintained GFP expression at both concentrations (FIG. 9E). Of note, Nicotinamide, a Sirtuin Family HDAC inhibitor (class III) that was used in the cultivation of human colon crypts (Jung et al., 2011; Sato et al., 2011a), did not promote GFP expression or cell proliferation when combined with CHIR or Wnt3a (FIG. 9F), indicating it acts through different mechanisms than VPA. Furthermore, when single Lgr5+ stem cells were cultured using CHIR with TSA or Tubastatin A, or VPA with Wnt3a, BIO or LiCl, cells exhibited similar colony-forming efficiency, colony morphology and GFP expression with that of the CV condition (FIG. 10).

Figure 11A:
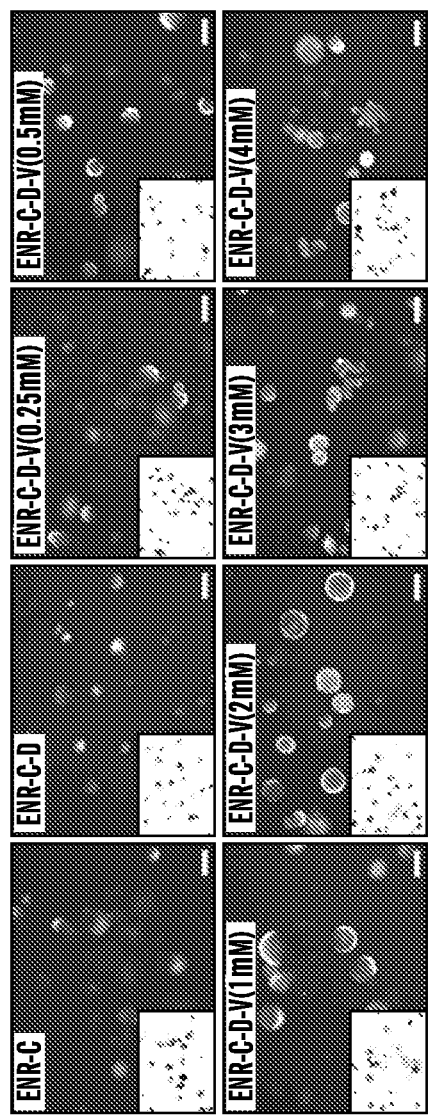
FIGS. 11A-11D depict mechanism of VPA.

Previous reports have shown that Notch pathway activation is required to inhibit secretory cell differentiation and maintain self-renewal of stem cells, which is consistent with the effects of VPA treatment. Whether VPA targets elements of the Notch pathway to exert its effects was evaluated. First, rescue of Notch inhibition by the addition of VPA was tested. Treatment with γ-secretase inhibitor DAPT led to impaired cell proliferation and GFP expression, which was rescued by VPA in a dose dependent manner (FIG. 11A). This suggests VPA acts downstream of NICD formation and could bypass the requirement of ligand-receptor mediated Notch activation.

Figures 11B, 11C, 11D:
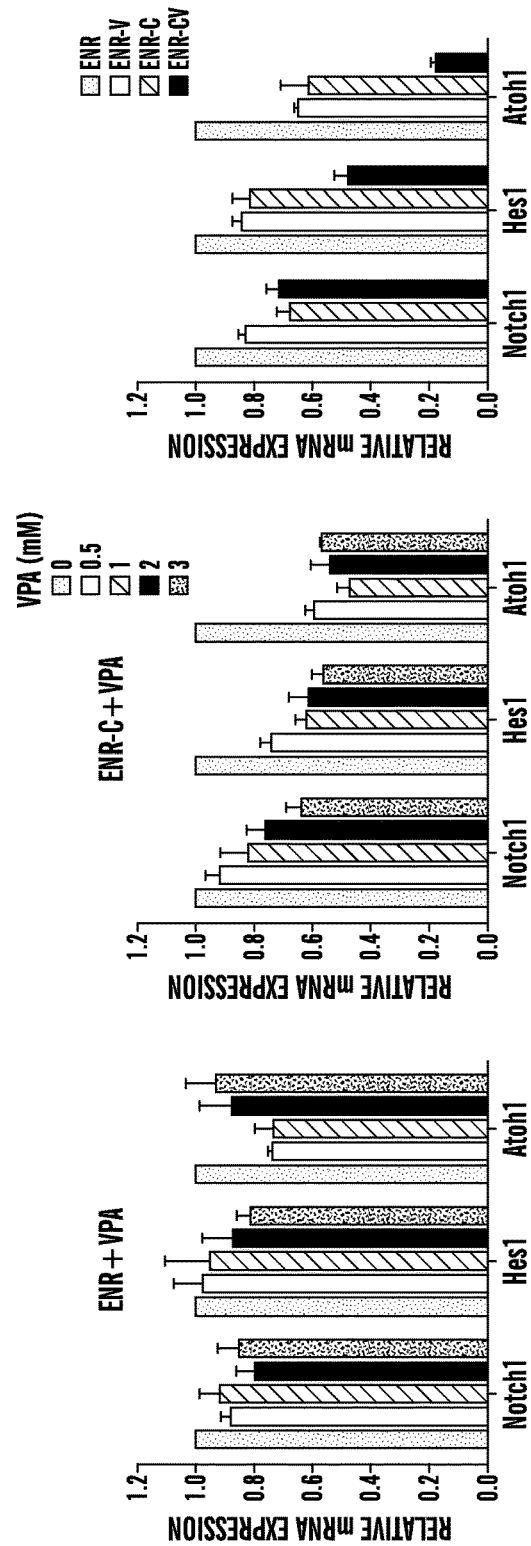

VPA was previously shown to activate the Notch pathway in cancer cells lines (Greenblatt et al., 2007; Stockhausen et al., 2005). To investigate the effect of VPA on the activation of the Notch pathway, cells cultured in ENR or ENRC conditions were treated with VPA and analyzed for the expression of Notch pathway genes. It was determined, however, that addition of VPA to ENR or ENR-C for 24 hours moderately decreased the expression of Notch1 or Hes1, which is a downstream target gene of Notch (FIGS. 11B and 11C). Additionally, a pronounced decrease of the negative Notch target Atoh1 (Math1) in cells treated with VPA and CHIR for 24 hours or 6 days was observed (FIG. 11B-11D). Atoh1 has been shown to be essential for the differentiation of ISC towards secretory cell lineage (van Es et al., 2010; Yang et al., 2001). Intestinal stem cells remain functional both in vivo and in vitro after Paneth cell ablation induced by Atoh1 deficiency (Durand et al., 2012; Kim et al., 2012). Atoh1 inhibition after CHIR or CHIR+VPA treatment would help maintain the self-renewal program of intestinal stem cells.

Figure 12B:
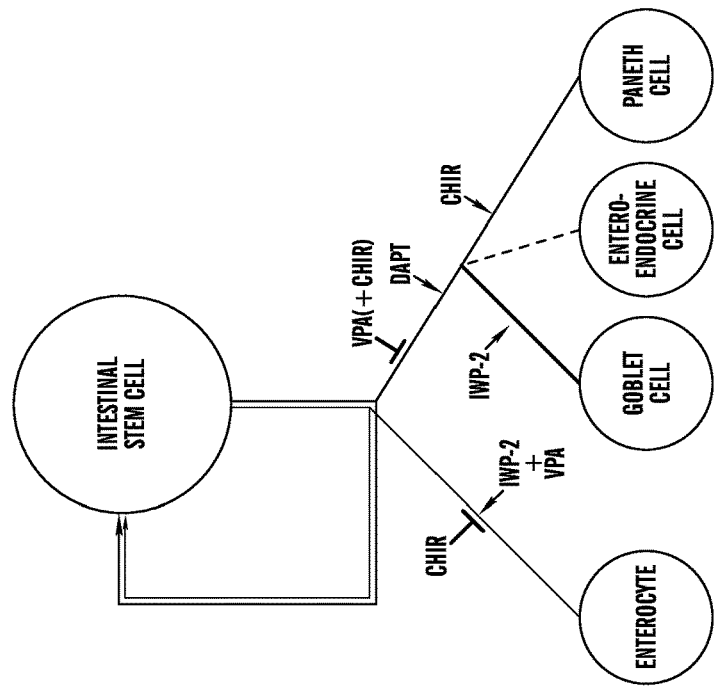
FIGS. 12A-12B depict a model for Intestinal Stem Cell self-renewal and differentiation (FIG. 12A) under physiological conditions and (FIG. 12B) in vitro culture.
Figure 12A:
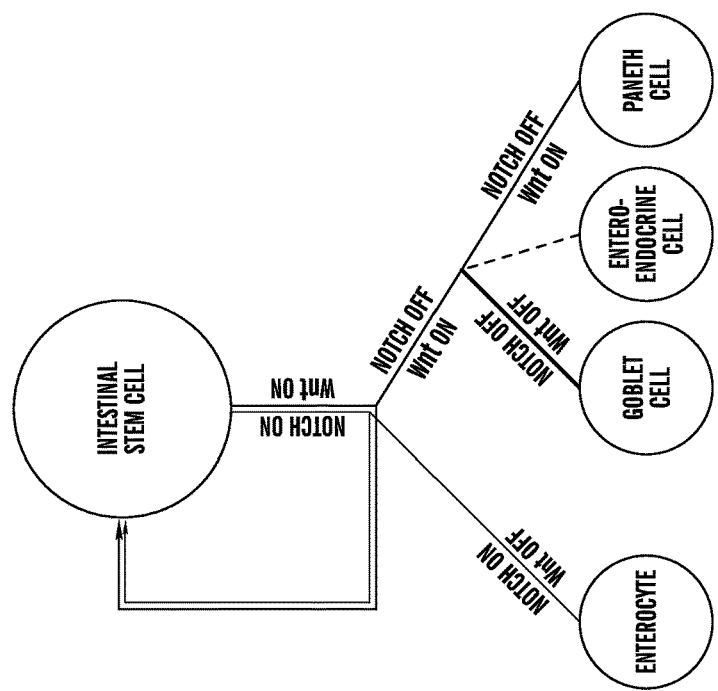

Accordingly, the control of the self-renewal of Lgr5+ intestinal stem cells and their differentiation towards differentiated cell types in the intestinal epithelium in vitro has now been achieved through using a combination of growth factors and small molecule inhibitors, which closely mimics the in vivo intestinal epithelial biology (FIGS. 12A and 12B). Under physiological conditions (FIG. 12A), the self-renewal and differentiation of ISCs are controlled by the cooperation of Wnt and Notch pathways. The activation of both pathways (indicated by Wnt On, and Notch On) maintains ISCs in an undifferentiated, self-renewing status. The deactivation of the Notch pathway (Notch Off) leads to the specification of secretory cell types and further deactivation of the Wnt pathway (Wnt Off) leads to goblet cell differentiation. Continuous activation of the Wnt pathway in the absence of Notch leads to Paneth cell differentiation. There is no strong dependence of the Wnt pathway for enteroendocrine cell differentiation. Alternatively, continuous Notch activation and Wnt deactivation leads to enterocyte cell differentiation. When Lgr5+ stem cells are cultured in vitro (FIG. 12B), CHIR99021 activates the Wnt pathway and inhibits enterocyte differentiation while VPA alone or together with CHIR suppresses secretory cell specification. The combination of CHIR and VPA maintains ISCs in an undifferentiated, self-renewing status. The inhibition of the Notch pathway with DAPT leads to the specification of secretory cell types and further addition of CHIR leads to Paneth cell differentiation, while addition of the Wnt pathway inhibitor IWP-2 leads to goblet cell differentiation. Alternatively, the combination of IWP-2 and VPA, which induces differentiation and suppresses secretory cell specification leads to enterocyte differentiation.

Example 5: Proliferation of Lgr5-Positive Stem Cells Derived from Inner Ear is Increased in the Presence of CHIR and VPA Sensory hair cells of the mammalian organ of Corti in the inner ear do not regenerate upon damage. Li et. al., 2003, found that adult utricular sensory epithelium contains cells that display the characteristic features of stem cells. These inner ear stem cells can be cultured in vitro as suspension spheres in the presence of EGF, bFGF and IGF-1 (Li et al., 2003). Later, it was found that post-mitotic supporting cells retain the ability to divide and trans-differentiate into new hair cells in culture (Patricia et al., 2006, Nature), suggesting these supporting cells may be inner ear stem cells. Purified cochlear supporting cells can be cultured in vitro in the presence of EGF, bFGF on embryonic periotic mesenchymal feeder cells. (Patricia et al., 2006). Shi et al found that a subset of supporting cells in the newborn and adult murine cochlea express Lgr5, a marker for adult stem cells (Shi et al., 2012). Importantly, Lgr5-positive cells can be isolated and cultured in a single-cell suspension, in the presence of EGF, bFGF and IGF-1, and display enhanced self-renewal capacity compared with Lgr5-negative cells. Previous inner ear stem cell cultures utilized a suspension culture method in which only approximately 0.068% of total cells (Li et al., 2003) or 2% of sorted Lgr5-positive cells could form spheres (Shi et al., 2012), probably because of inadequate growth environment for the cells. As described herein, a highly efficient in vitro culture system for inner ear stem cells has now been developed.

Figure 13A:
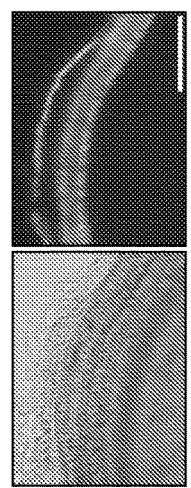
FIGS. 13A-13B depict the combination of CHIR and VPA promoting the proliferation and GFP expression of Lgr5+ stem/progenitor cells derived from the mouse inner ear.
Figure 13B:
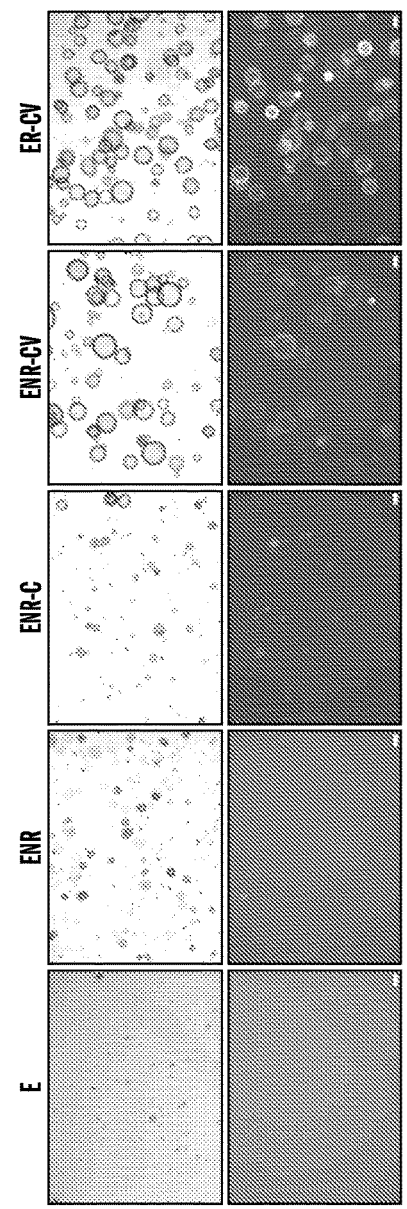

Isolated mouse cochlea from P1 to P2 Lgr5-GFP mice contained Lgr5-positive cells as shown in FIG. 13A. The same culture condition (EGF, Noggin, R-spondin1, or "ENR") as used in Lgr5+ small intestinal stem cell cultures was first established. As shown in FIG. 13B, the combination of EGF, Noggin and R-spondin1 increased the colony-forming efficiency from single cochlear epithelial stem cells compared to EGF alone. As expected, the combination of CHIR and VPA, but not CHIR alone, greatly increased the colony-forming efficiency, cell proliferation and GFP expression of the cells. Surprisingly, removing Noggin from the ENR-CV combination (the "ER-CV" condition) resulted in slightly higher colony-forming efficiency and higher GFP expression level, as shown by brightfield and GFP images in FIG. 13B. These results indicate that Wnt pathway activation by R-spondin1 or CHIR promotes the proliferation of inner ear stem cells and the combination of CHIR and VPA greatly promotes the proliferation and self-renewal of inner ear stem cells.

Mitogenic growth factors including EGF, bFGF and IGF-1 were previously used in the suspension culture system and shown to promote sphere formation of isolated inner ear stem cells (Li et al., 2003; Shi et al., 2011). Next the effects of CHIR and VPA were tested in the presence of these growth factors as described in Table 1.

TABLE 4

| | Cell Culture Solutions | | | | |
|---|---|---|---|---|---|
| | Reagent Name | Supplier | Cat# | Stock Solution | Final Concentration |
| Control Medium | Advanced DMEM/F12 | Invitrogen | 12634-010 | | |
| | GlutaMAX | Invitrogen | 35050-061 | 200 mM | 2 mM |
| | Penicillin/Streptomycin | Invitrogen | 15140-122 | 10000/10000 U/ml | 100/100 U/ml |
| | HEPES | Invitrogen | 15630-080 | 1M | 10 mM |
| | N2 Supplement | Invitrogen | 17502-048 | 100x | 1x |
| | B27 Supplement | Invitrogen | 12587-010 | 50x | 1x |
| | N-Acetylcysteine | Sigma-Aldrich | A9165 | 500 mM | 1 mM |
| Growth factors | EGF Recombinant Human Protein | Invitrogen | PHG0311 | 500 µg/ml | 50 ng/ml |
| | Mouse Recombinant Noggin | Peprotech | 250-38 | 100 µg/ml | 100 ng/ml |
| | Human Recombinant R-Spondin 1 | Peprotech | 120-38 | 500 µg/ml | 50 ng/ml |

TABLE 4-continued

Cell Culture Solutions

| | Reagent Name | Supplier | Cat# | Stock Solution | Final Concentration |
|---|---|---|---|---|---|
| | Human Recombinant FGF-Basic | Invitrogen | PHG0024 | 100 µg/ml | 10 ng/ml |
| | IGF-1 Recombinant Human protein | Invitrogen | PMG0078 | 100 µg/ml | 50 ng/ml |
| Small molecules | CHIR-99021 | LC Laboratories | C-6556 | 10 mM | 3 µM |
| | Valproic acid sodium salt | Sigma-Aldrich | P4543 | 1M | 1 mM |
| | Y-27632 | Sigma-Aldrich | Y0503 | 10 mM | 10 µM |
| | Trichostatin A | Sigma-Aldrich | T8552 | 10 mM | 20 nM |
| | Sodium butyrate | Sigma-Aldrich | B5887 | 1M | 0.5 mM |

Figure 14A:
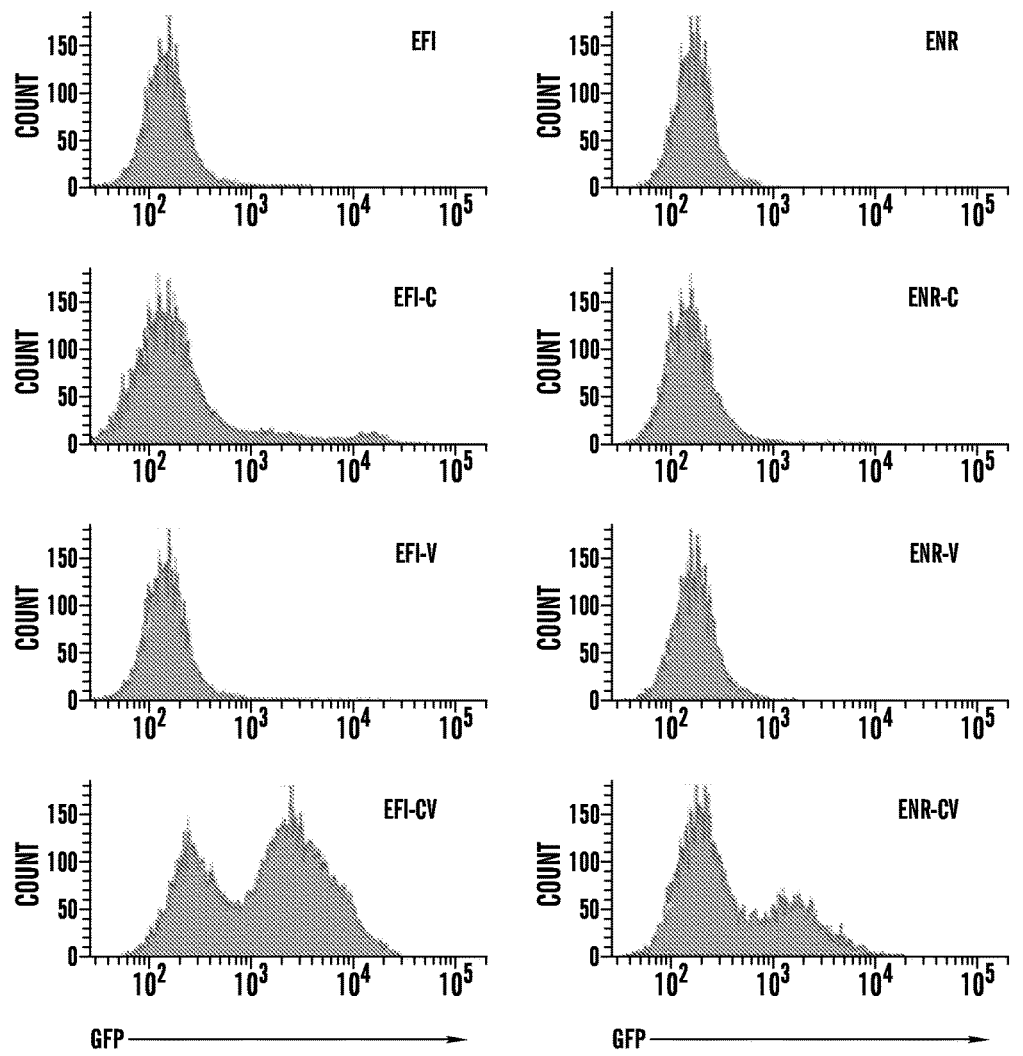
Figure 14B:
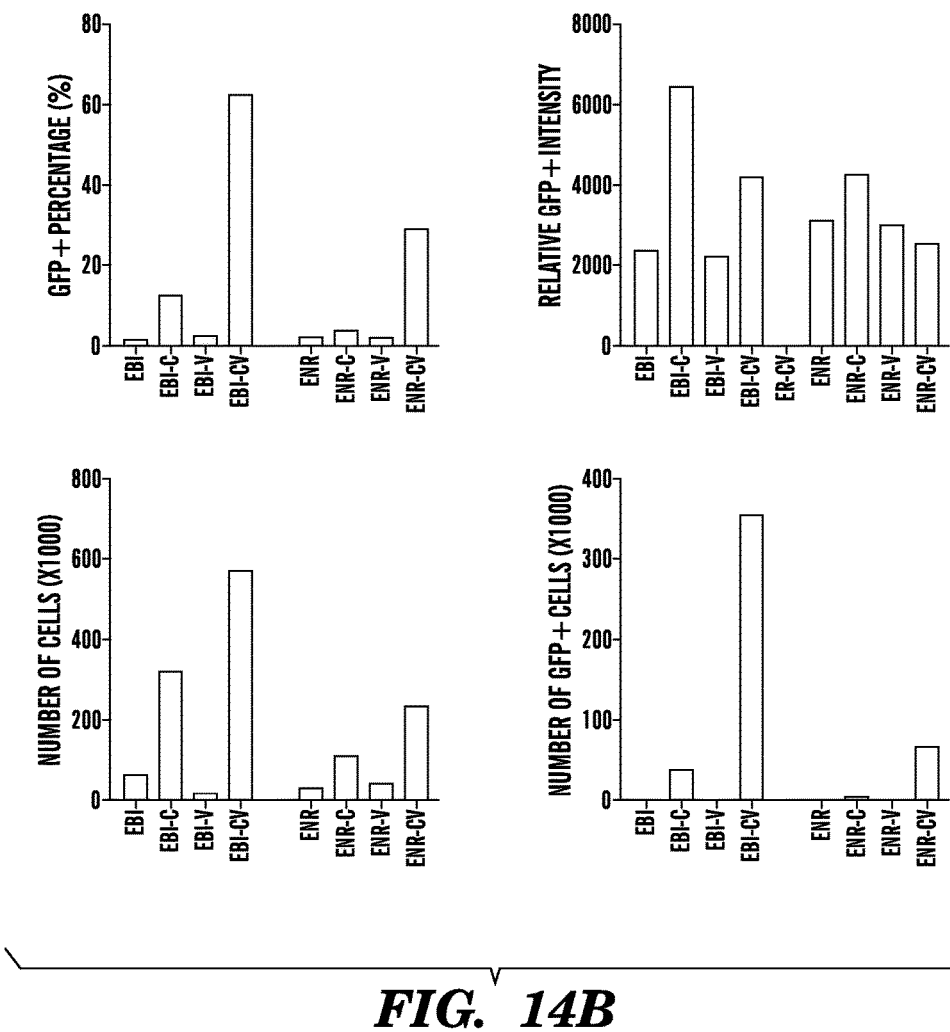
Figure 14C:
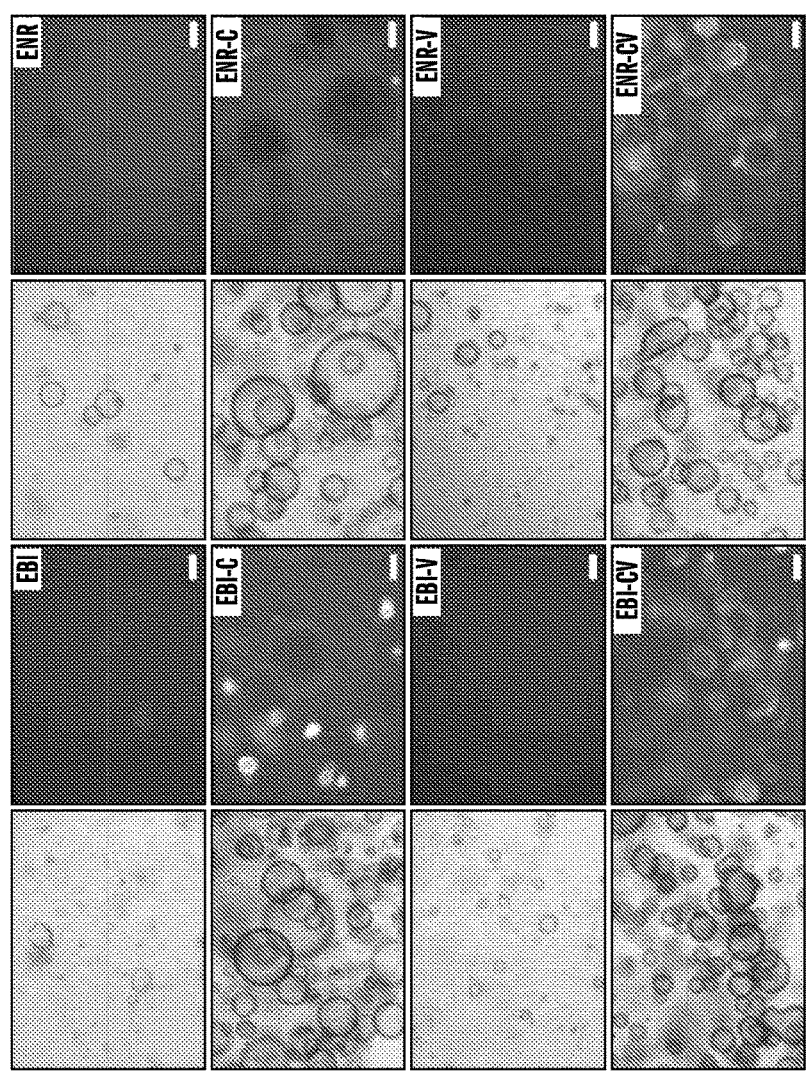

Isolated organ of Corti from Lgr5-GFP mice were dissociated into single cells using accutase and cultured in multiple combinations of soluble factors and small molecules in Matrigel for 8 days. The resulting cultures were further dissociated into single cells and analyzed using FACS. Consistent with previous results, the addition of CHIR and VPA, but not CHIR or VPA alone, greatly increased cell proliferation (9-20 fold) and GFP expression as shown by the percentage of GFP+ cells (60 fold) and relative GFP intensity of GFP+ cells (2 fold) (FIGS. 14A and 14B). In addition, the combination of EGF, bFGF and IGF-1 (designated as EFI) improved cell proliferation and GFP expression compared with the ENR condition (FIG. 14A-14C).

To further investigate the effects of individual growth factors when combined with CHIR and VPA, growth factors including Mitogenic growth factors (EGF, bFGF and IGF-1) as well as the Wnt agonist R-spondin 1 in combination with CHIR and VPA were tested. The addition of EGF to the CV condition greatly increased cell proliferation as indicated by increased cell number in the culture. Addition of bFGF but not IGF-1 or R-spondin 1 to EGF+CV further increased cell proliferation and GFP expression (FIG. 14D). Although the addition of IGF-1 or R-Spondin 1 to the EGF+bFGF combination slightly increased GFP expression (FIG. 14E), we found that they are not essential to maintain the proliferation and GFP expression of cultured cells (FIG. 14F).

Example 6: Lgr5-Positive Intestinal Stem Cells Form Transplantable Crypts

Figure 15:
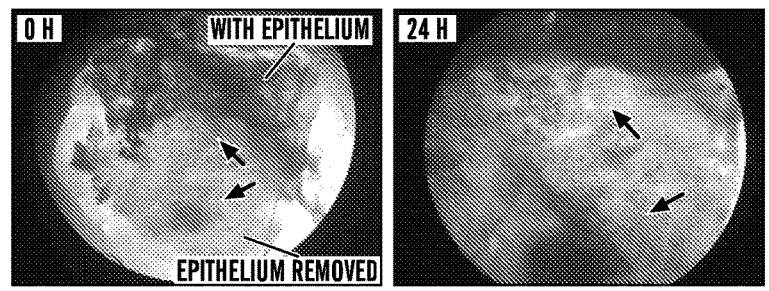
FIG. 15 depicts seeding of murine small intestinal crypts on healthy mouse colon tissue in vitro. The left panel shows isolated small intestinal crypts placed onto colon with partially denuded epithelium. White arrows indicate the seeded crypts. The right panel shows seeded crypts attached to the colon and spreading across its surface after 24 hours. Black arrows indicate the same location as white arrows in left panel.
Figure 16:
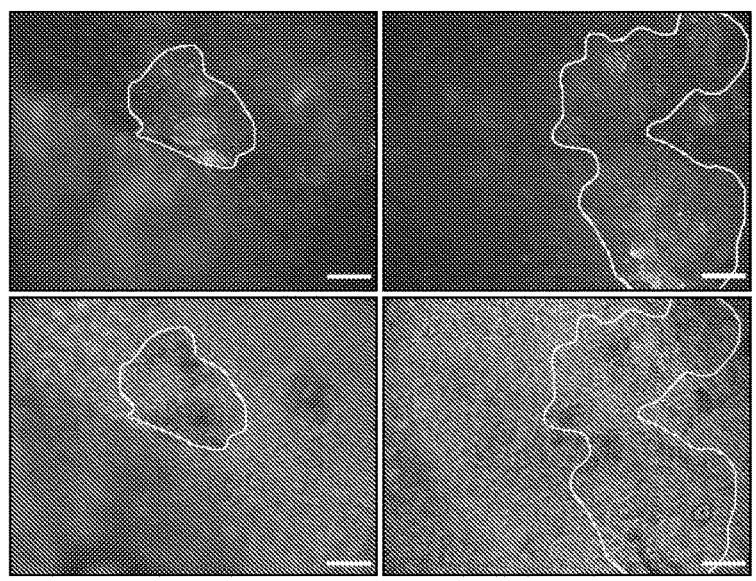
FIG. 16 depicts engraftment of crypts 48 hours after seeding. Fluorescent (top panel) and brightfield (bottom panel) images of mouse colon tissue seeded with crypts are shown. Crypts were stained with DiD prior to seeding. White lines indicate areas that include engrafted cells.
Figure 17:
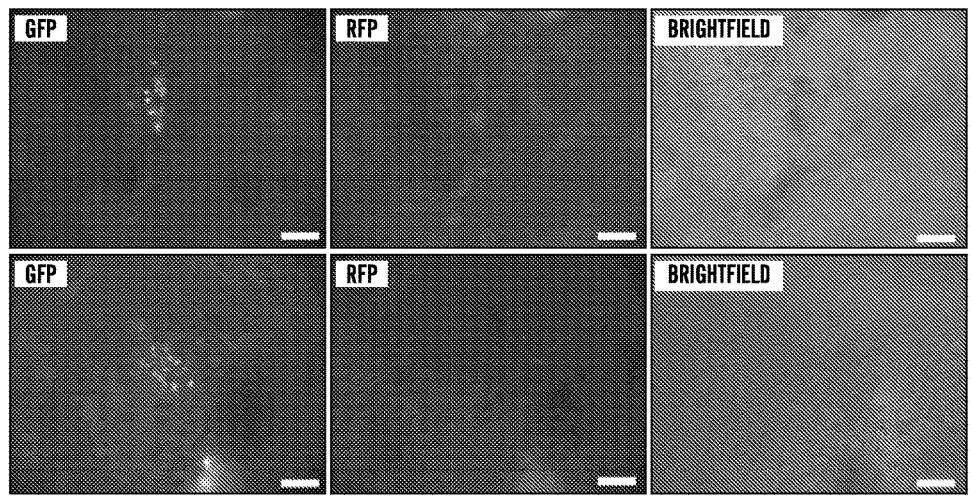
FIG. 17 depicts engraftment of crypts following 6 days of in vitro culture. Shown are GFP (left panel), RFP (middle panel) and brightfield (right panel) channel images of mouse colon tissue seeded with crypts. GFP signal indicates the presence of Lgr5 cells.
Figure 18:
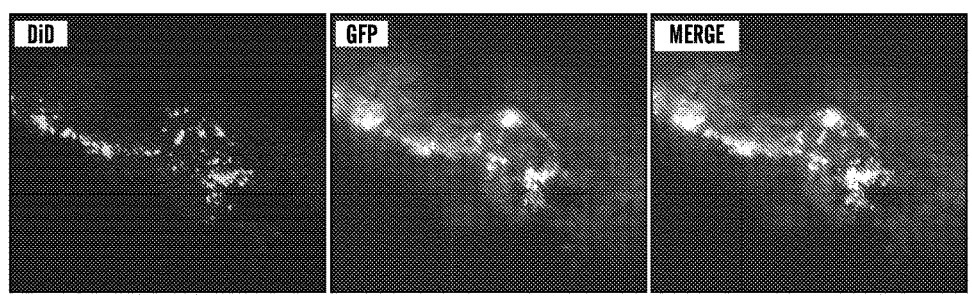
FIG. 18 depicts a confocal image of excised prolapsed ulcerative colitis tissue from the TRUC mouse with engrafted crypts. Crypts were stained with DiD prior to seeding. Prolapsed tissue is shown via green autofluorescence.

To examine the potential to transplant intestinal stem cells, the engraftment of small intestinal crypts was tested on healthy colon tissue in vitro. Colon tissue was harvested from wild type mice and opened longitudinally. A 1 cm fragment was removed and washed with PBS. The epithelial layer was removed by scraping using a surgical blade and the tissue was placed into a 24 well plate. Small intestinal crypts isolated from Lgr5-GFP mice were stained with a DiD membrane dye and placed onto the colon tissue within 5-10 µl of crypt culture media containing advanced DMEM/F12 (Invitrogen), 2 mM GlutaMax (Invitrogen), 10 mM Hepes (Invitrogen),100 U/ml Penicillin/100 ug/ml Streptomycin (Invitrogen), 1× N2 supplement (Invitrogen), 1× B27 supplement (Invitrogen), 50 ng/ml EGF (Peprotech), 500 ng/ml R-spondin 1 (R&D Systems), 10 µM Y-27632 (Rho Kinase inhibitor, Sigma-Aldrich; and 100 ng/ml Noggin (Peprotech). The tissue was further incubated at 37° C. for 30-60 minutes in a humidified environment to permit the adherence of crypts. Crypt culture media were then added into the wells and the crypts were further cultured for 7 days. Seeded crypts attached to the colon and spread in 24 hours (FIG. 15). Fluorescent image showed crypts engrafted on the colon in 48 hours (FIG. 16) and maintained Lgr5-GFP expression for at least one week (FIG. 17).

To further test the engraftment ability of small intestinal crypts, a TRUC mouse model that exhibits spontaneous Ulcerative Colitis and mimics the human condition was used. Prolapsed tissue was excised from the TRUC mouse and washed with PBS and placed into a 24 well plate. Small intestinal crypts were stained with DiD and placed onto the prolapse tissue. The tissue was then incubated at 37° C. for 30-60 min in a humidified environment to permit the adherence of crypts. Crypt culture media was added into the wells. The prolapsed tissue and crypts were further cultured in vitro for 2 days. As expected, crypts engrafted on the prolapsed tissue (FIG. 17).

Figure 19A:
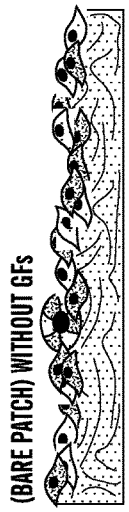
Figure 19B:
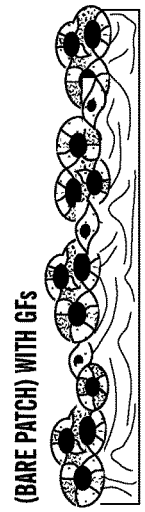
Figure 19C:
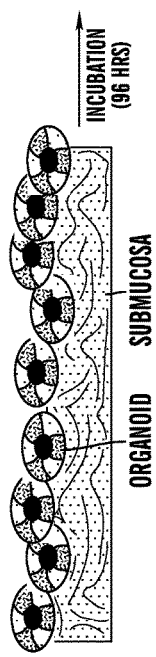
FIGS. 19C and 19D depict GF-infused SIS (GFs include EGF, Noggin, R-spondin 1, Y-27632, Valproic Acid, CHIR) to support 3-dimensional organoid growth.
Figure 19D:
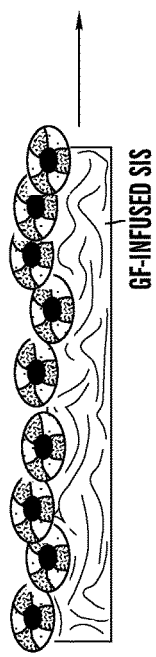
Figure 19E:
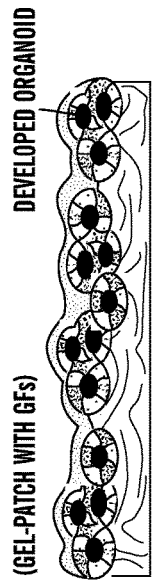
FIGS. 19E and 19F depict gel-patch composed of GF-infused SIS with a collagen overlay.
Figure 19F:
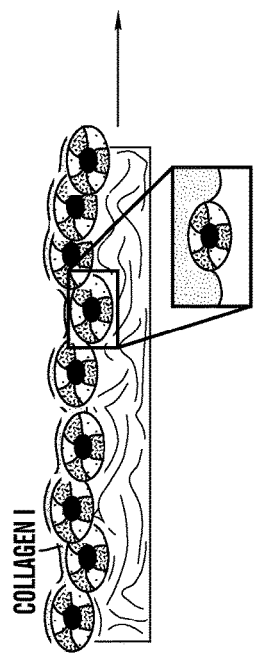

Example 7: Patch Culture Systems for Small Intestine Organoids Mimic the 3-Dimensional Physiological Environment An in vitro culture system capable of supporting the growth of large-scale, organized 3-dimensional cellular structures (e.g. organoids) on a submucosal scaffold has now been developed. As described below, an improved small intestinal submucosa ("SIS")-based culture system for 3-dimensional tissue constructs was prepared by seeding the submucosa with a preselected cell type and facilitating growth with a unique collagen-based overlay. This overlay, initially a viscous fluid pre-polymerization, is used to coat seeded, early stage cells or organoids (subcultured from cells), as well as to coat the SIS base to encase the cells in a collagen residue (FIGS. 19E and 19F). After polymerization, the liquid solidifies to maintain its position contacting cell membranes as well as SIS and promotes organoid expansion. It has now been discovered that varying the composition of SIS with this overlay facilitates cell adhesion and growth. This will facilitate in vitro, as opposed to in vivo, tissue maturation. This is a unique improvement over other submucosal-based and similar synthetic systems in that 3-dimensional expansion of adhered cells into large, endogenous-type organoids is achieved prior to transplantation.

Additionally, a method to support 3-dimensional organoid growth on submucosa at rates comparable to Matrigel without the use of gel layers has also been discovered. This system is composed of vertebrate SIS and preselected cells, seeded on the SIS patch. Preselected bioactive agents are infused in the patch prior to cell seeding to support this gel-free culture system (FIGS. 19C and 19D).

To develop the patch culture system, varying combinations of an SIS base and collagen overlay with infused growth factors (FIGS. 19E and 19F) were explored. This permitted the creation of a more physiological tissue interface with a transition from stiff (SIS) to soft (collagen) matrix. It was determined that seeded cells and organoids coated with a collagen residue are provided with a 3-dimensional environment similar to that provided by Matrigel. As such, this system is a suitable replacement for Matrigel in culturing 3-dimensional organoid constructs. The majority of seeded cells or organoids are both adhered to the SIS on the lower half of the cell membranes but also enveloped by polymerized collagen on non-adhered regions of the membrane (FIG. 19E, inset). Thus, each cell membrane is functionally encased in a form of matrix, whether it is SIS or collagen. In some samples, a variety bioactive agents was employed to support cell and organoid seeding, growth, and differentiation beyond SIS alone (FIG. 19F). While the applicants describe an infusion of biomolecules specific to intestinal stem cell culture, it is declared that biomolecules can be tailored to aid in the growth of other seeded cells from different tissues including pancreas, breast, liver, and stomach tissues. Accordingly, tissues-specific biomolecules may selected from the following: antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, small molecule, nanoparticle, collagen lattice, antigenic agent, cytoskeletal agent, nucleic acid, cellular attractant.

To begin, crypts were isolated in accordance with previous methods (Sato et al., 2009, Yui et al., 2012). Murine small intestine was isolated, incised longitudinally and washed in ice-cold PBS to clear luminal contents. Fragments were cut into 2 mm pieces, transferred to a 50 ml falcon tube and gently washed in 50 ml of ice-cold PBS using a 10 ml pipette. The supernatant was removed and the process was continued until the supernatant cleared. Fragments were incubated for 45 minutes at 4° C. in PBS containing 2 mM EDTA to release crypts. The supernatant was removed and fragments pipetted up and down with 50 ml of PBS. Once the supernatant was confirmed to contain the crypt fraction, the suspension was filtered through a 70 µm cell strainer and spun in a centrifuge at 300 g for 5 minutes. Crypts were re-suspended in 10 ml of ice-cold basal culture media (containing advanced DMEM/F12 (Invitrogen) 2 mM GlutaMax (Invitrogen), 10 mM Hepes (Invitrogen) and 100 U/ml Penicillin/100 ug/ml Streptomycin (Invitrogen)) and transferred to a 15 ml falcon tube. The PBS wash was repeated and the crypts were spun at 200 g for 2 minutes to remove single cells. Crypts were counted and plated in a 48 well plate with either Matrigel or Collagen I (consisting of 100 ul 10×PBS, 4.9 µl NaOH, 684 µl H20 and 211 µl collagen type I (rat tail high concentration 9.49 mg/ml; BD Biosciences) at a concentration of 1000 crypts per well, each well containing 200 µl of matrix. After polymerization of the chosen gel product, 500 µl of 1× standard crypt culture medium (serum free) was added, containing advanced DMEM/F12 (Invitrogen), 2 mM GlutaMax (Invitrogen), 10 mM Hepes (Invitrogen),100 U/ml Penicillin/100 ug/ml Streptomycin (Invitrogen), 1× N2 supplement (Invitrogen), 1× B27 supplement (Invitrogen), 50 ng/ml EGF (Peprotech), 500 ng/ml R-spondin 1 (R&D Systems), 10 µM Y-27632 (Rho Kinase inhibitor, Sigma-Aldrich; and 100 ng/ml Noggin (Peprotech). Cells were grown for 4-5 days before seeding onto the patch, changing media every other day. Y-27632 was only included in the culture media for the first 48 hours.

After 4-5 days in culture the Lgr5+ organoids were passaged using a modified protocol described previously (Sato et al., 2009). Culture media was removed from the matrigel, which was then manually broken with a p1000 pipette and then transferred to a BSA coated 15 ml falcon tube. Collagen gels were incubated in DMEM containing collagenase type XI at 37° C. for 5 minutes and then transferred to a BSA coated 15 ml falcon tube. Basal media was added and organoids were gently disrupted with frequent inspection by inverted microscopy until the majority of organoids were single-crypts. Organoids were washed in 10 ml of basal media and centrifuged at 200 g for 2 minutes. The pellet was resuspended in crypt culture media at a concentration of 500 single-crypt organoids per 500 µl.

Patches were generated and prepared for seeding inside the wells of a standard 48-well plate (one patch per well, luminal side up). SIS was cut into the desired length to cover the bottom of each well (~1 cm for 48 well plate). Isolation of SIS has been previously described (Badylak et al., 1989). Using blunted forceps, each SIS segment was transferred to the bottom of a well and carefully spread to its full diameter, luminal side facing up. Orientation was confirmed by analysis under inverted microscopy to visualize the acellular remnants of crypts on the superficial surface. Depending on the compliance and strength required, multiple layers of SIS can be layered and bonded together. In this case, each segment can be spread on top of one another for the desired number of segments and the patch gently compressed with forceps and allowed to air dry at 5% $CO_2$, 37'C for 5 minutes. Prior to seeding, each patch segment was dehydrated by passive evaporation for 24 hours and infused with concentrated crypt culture media and optionally, small molecules as described below. Specifically, each segment of the patch was placed and spread, luminal side up, in the well of a 48 well plate, and 100 µl of concentrated factors (EGF, Noggin, R-spondin 1, Y-27632, Valproic Acid and CHIR) was deposited for 24 hour incubation at 5% $CO_2$, 37° C.

Figure 20C:
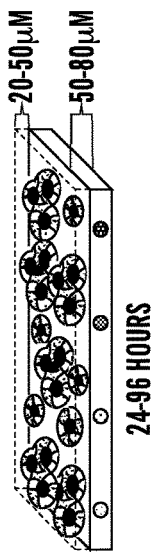
FIG. 20C depicts complete culture system with collagen overlay, thickness measurements depicted.
Figure 20B:
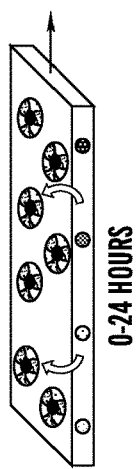
FIG. 20B depicts an initial adherence phase with arrows depicting growth embedded factor diffusion support.
Figure 20A:
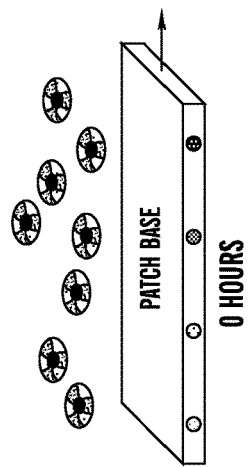
FIG. 20A depicts a schematic of the seeding procedure with Lgr5+ organoids; patterned circles represent infused growth factors (EGF, Noggin, R-spondin 1, Y-27632, Valproic Acid and CHIR).

Individual 500 µl single-crypt organoid samples were deposited into a well containing a patch base and incubated for 24 hours at 5% $CO_2$ and 37° C. (FIG. 20A). The seeded patches were maintained in culture media for 24 hours to allow for firm adherence and to obtain nutritional support from embedded growth factors in the patch (FIG. 20B).

In some samples, a thin collagen gel residue (termed as the gel-patch) was coated onto the top of the patch/organoid complex to provide a minimal but functional 3-dimensional environment for each organoid. Physical and chemical cues obtained from the cell surface enhance 3-dimensional cell structure proliferation in order to replicate physiological morphology (Seidi, A., et al., 2011). Collagen I matrix (20-40 µl) was layered on seeded patches, taking care to leverage surface tension to prevent spreading of the gel beyond the patch (FIG. 20C) and the well plate incubated at 5% $CO_2$, 37° C. for 30 minutes. Crypt culture media (500 μl) was deposited into each well and changed every other day.

In some samples, the patch was incubated in growth factors prior to seeding to examine whether it would facilitate adherence of organoids in the first 24 hours. Accordingly GF-infused (including EGF, Noggin, R-spondin 1, Y-27632, Valproic Acid and CHIR) versus non-infused patches (SIS in PBS) were seeded. In this assay, non-infused patches used basal media in lieu of culture media to deprive organoids of media growth factors as well.

Growth of intestinal organoids was assessed by quantifying the number of crypts per organoid in 7 separate systems: Matrigel (control), the gel-patch system with infused Growth Factors (referred to herein as GFs, and including EGF, Noggin, R-spondin 1, Y-27632, Valproic Acid and CHIR), the bare patch with infused GFs but without collagen overlay, Collagen I gel only, Collagen I gel with GFs added to directly to the culture media (including EGF, Noggin, R-spondin 1, Y-27632, Valproic Acid and CHIR), Collagen I gel with GFs embedded in the gel itself (including EGF, Noggin, R-spondin 1, Y-27632, Valproic Acid and CHIR), and the bare patch without collagen overlay or infused GFs. Other than the Collagen I group with GFs and small molecules added directly to the media, all culture media was standard between each system, was changed every other day, and included EGF, Noggin, R-spondin 1, Y-27632 (first 48 hours only). Standard crypt culture media is described above.

Figure 21A:
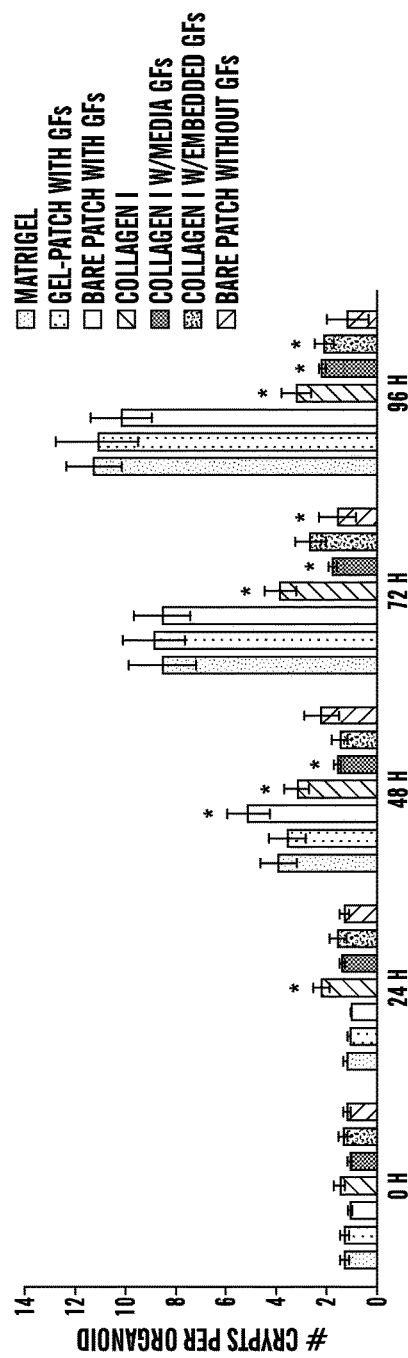
FIG. 21A provides a comparison of organoid growth in 7 culture systems. The series are, from left to right, Matrigel, Gel-Patch with GFs, Bare Patch with GFs, Collagen I, Collagen I with Media GFs, Collagen I with embedded GFs, and Bare patch without GFs.
Figure 21C:
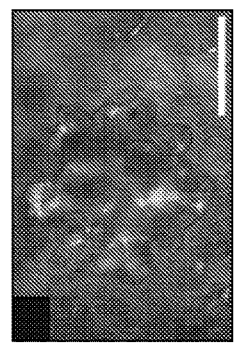
FIG. 21B and FIG. 21C show a representative organoid at 48 hours from the gel-patch system with GFs, with GFP+ fluorescence indicating Lgr5+ stem cells present in the crypt bases (some central autofluorescence is seen). *=p<0.05 at 24 hours (collagen I (CI) vs. all), 48 hours (bare patch with GFs (BPGF) vs. all; CI vs. Matrigel (M); CI with GFs (CIGF) vs. M, CI, Collagen I with embedded GFs (CIEGF), bare patch (BP), gel-patch system with GFs (PSGF)), 72 hours (CI vs. all; BP, CIEGF, and CIGF vs. M, PS, BPGF, CI) and 96 hours (CI vs. all, BP, CIEGF, and CIGF vs. all). Scale bar (FIGS. 21B and 21C)=200 um.
Figure 21B:
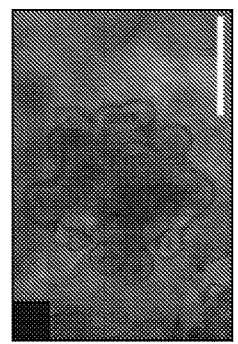

The experiment was conducted over 96 hours and daily quantification of organoid growth was documented by visually inspecting the number of crypts per organoid. The gel-patch system with GFs was able to support organoid growth at levels comparable to Matrigel controls (FIG. 19). The bare patch, without GFs, was not able to support measurable organoid growth. Upon closer inspection, the bare SIS patch appeared to grow Lgr5+ cells in sheets as opposed to 3-dimensional organoids. However, the bare patch with infused GFs (EGF, Noggin, R-spondin 1, Y-27632, Valproic Acid and CHIR) supported organoid growth on par with both the gel-patch system and Matrigel. This indicates that, with sufficient GF support, a gel-free culture system is capable of sustaining short-term, 3-dimensional organoid growth on par with Matrigel. While Collagen I alone facilitates moderate organoid growth, SIS infused with GFs is a viable replacement for collagen's 3-dimensional growth promoting effect. Furthermore, when the same GFs (EGF, Noggin, R-spondin 1, Y-27632, Valproic Acid and CHIR) were added directly to the culture media of the Collagen I gel culture, organoid growth rates remained low. Additionally, when Collagen I gel was prepared with the aforementioned GFs embedded directly in gel prior to seeding, organoid growth rates remained low. GFP signal was maintained throughout the gel-patch system (representative example in FIGS. 21B and 21C). The observation that the bare patch (SIS without a collagen overlay or GFs) failed to support structured organoid growth reaffirms the importance of sufficient physical and chemical cues to promote 3-dimensional structures.

Figure 22:
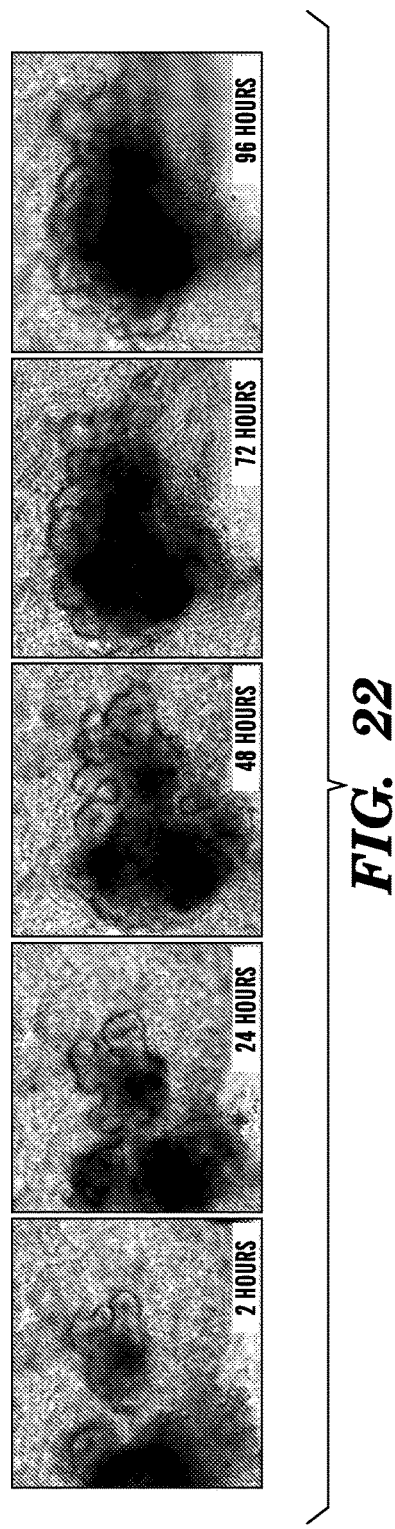
FIG. 22 depicts successful growth and crypt expansion of a seeded organoid in the Gel-patch with GFs system. A representative sequence of images depicting ex-vivo expansion of a seeded organoid on the SIS patch system with GFs is shown. Out-of-focus crypts are an effect of growth in 3-dimensions viewed in single plane microscopy.
Figure 23A:
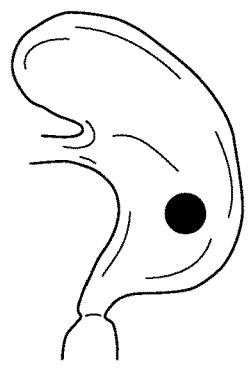
FIG. 23A provides a schematic showing the creation of a 4 mm gastric defect. Placement of a 6 mm patch over the defect is shown in FIG. 23B.
Figure 23B:
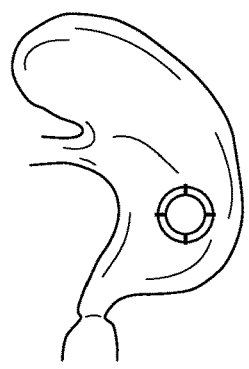
As shown in FIG. 23C, there was no visible defect on the external gastric wall, as indicated on a representative stomach sample at 1 week post-op. Gross defects (arrows), as viewed from the internal gastric wall, are displayed according to the type of patch placed.
FIG. 23D shows SIS patch without GFs.
FIG. 23E shows SIS patch plus GFs and FIG. 23F shows PGSU backing only, without SIS. The SIS patch with GFs showed complete closure and epithelialization of the gastric wall effect, whereas defects remained partially open in SIS only and completely open in PGSU without SIS.
Figure 23C:
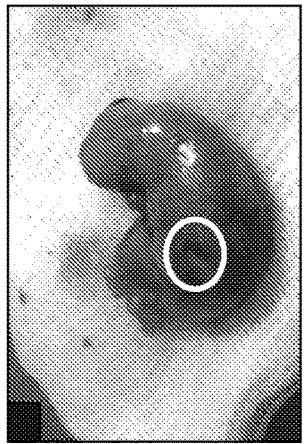
Figure 23D:
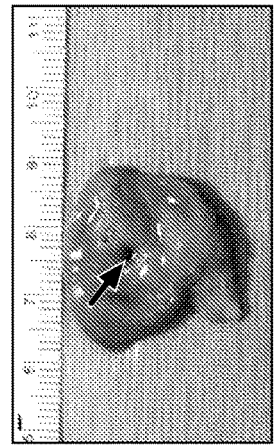
Figure 23E:
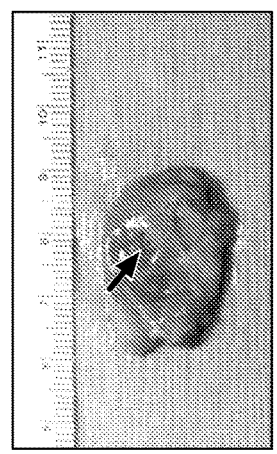
Figure 23F:
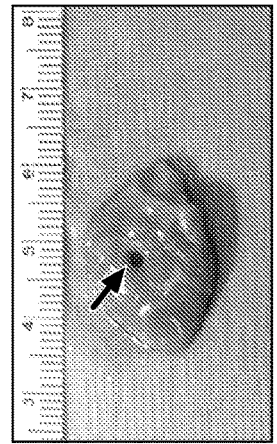

SIS or collagen alone has been used in the literature as a base scaffold for cell seeding, resulting in the formation of cellular monolayers (Baumert et al. 2007; Campodonico et al. 2004; Feil, G., et al. 2006; Zhang, Y., et al. 2000). By contrast, growing cells at the interface of these two matrices favors 3-dimensional organoid growth over monolayer growth. This mimics the physiological environment more closely, allowing for accelerated and structured growth. Importantly, these results describe a patch culture system for small intestine organoids that is a superior alternative to Matrigel. Matrigel-based transplantation in animal models has encountered significant barriers in moving towards a human model, the most critical including biocompatibility issues. Growing a 3-dimensional cell-based structure often requires embedding a thick matrix gel. The patch culture system overcomes this requirement while providing comparable results. Replacing Matrigel with a combination of endogenous extracellular matrix materials and specific bioactive growth factors avoids biocompatibility issues while maintaining 3-dimensional organoid, ex vivo growth. A timelapse image of 3-dimensional, ex vivo organoid expansion from an initial seed is demonstrated in FIG. 22.

Whether incubation of the patch in growth factors prior to seeding facilitates adherence of organoids in the first 24 hours was evaluated. The seeding efficiency was compared in growth factor infused patches (including EGF, Noggin, R-spondin 1, Y-27632, Valproic Acid and CHIR) versus non-treated patches (stored in PBS). The assay was conducted by measuring the percentage of organoids retained after media washes at 4 and 12 hours when cells are cultured solely in media devoid of growth factors (basal media only). When SIS was omitted and organoids were seeded directly on plastic collagen-coated and non-collagen coated wells, dissociation of all organoids occurred within 24 hours. However, SIS patches maintained the majority of organoids at 24 hours, in both structure and GFP expression. An improvement in adherence was observed when cells were seeded on growth factor infused patches (including EGF, Noggin, R-spondin 1, Y-27632, Valproic Acid and CHIR). Therefore, growth factor infusion may also be useful to provide adequate nutrition and factors during culture and following transplantation while bridging the gap to cellular engraftment.

Example 8: Implanted Patch Exhibits Growth-Promoting Properties In Vivo

Acellular, gel-free variations of the patch system were tested to evaluate mucosal healing properties in vivo. A rat surgical model of mucosal defects was designed in order to test the growth-promoting properties of the implantation patch in vivo. The implantation patch was assembled by carefully spreading a portion of SIS, luminal side facing up, over 6 mm, circular poly(glycerol sebacate) urethane (PGSU) backings. The patch was incubated at 5% $CO_2$, 37° C. for 30 minutes to allow bonding of the PGSU and SIS. A 4 mm defect was created in the gastric wall via punch biopsy, as shown in FIG. 23. Acellular patches (6 mm in diameter) were placed over the external gastric wall, carefully covering the defect with the chosen material. The patch was secured by an adapted Graham patch method (Sø, et al., 1996) using sutures and nearby connective tissue. Three variants of acellular patches were applied, including a) PGSU-backed SIS patch (without GFs), b) PGSU-backed SIS patch with GFs infused (EGF, Noggin, R-spondin 1, Y-27632, Valproic Acid and CHIR) and c) PGSU backing only (no SIS). At no point was peritonitis observed in any rat. One week after implantation over mechanically-induced gastric wall defects, the gastric tissue containing the defect and patch implants was harvested to conduct histological examination of tissue.

It was hypothesized that implanting variations of the patch would show varying degrees of mucosal healing. Gross examination demonstrated a significant benefit in the SIS patch with GFs, as the defect was epithelialized and closed. Partial closure without epithelialization was observed in SIS patches without GFs, and no closure or epithelialization was observed in the PGSU only (control) patches. Histological examination revealed mild inflammation in both the SIS patch with and without GFs, but no stomach content leakage. Histological examination of the PGSU-only patch demonstrated moderate inflammation as well as the presence of Giant cells, likely responding to leakage of stomach contents. Accordingly, patch culture systems described herein are transplantable from the culture dish directly to the patient, with increased translational potential, as the patch is rigid and less likely to obstruct in small spaces (e.g. the intestinal lumen, vascular spaces) given its low height profile.

Example 9: Culturing of Human Small Intestinal Crypts/Stem Cells

Human small intestinal crypts were isolated from a resected normal small intestinal specimen and cultured as described in Example 1. The same cell culture solutions used in the culture of mouse small intestinal stem cells/crypts, which comprise a combination of CHIR99021 and VPA or Tubastatin A added to the ENR (EGF, Noggin, R-Spondin 1) condition, were compared to published cell culture solutions for human intestinal stem cells/crypts (Jung et al., 2011; Sato et al., 2011). RT-PCR was used to assess the maintenance of epithelial stem cells in the culture, specifically by determining the self-renewal or differentiation status. LGR5 was used as a stem cell marker and ALPI, MUC2, CHGA and LYZ were used as differentiation markers. Cell growth was assessed by counting the cell number in the cultures and by observing the morphology and size of colonies.

Figure 24:
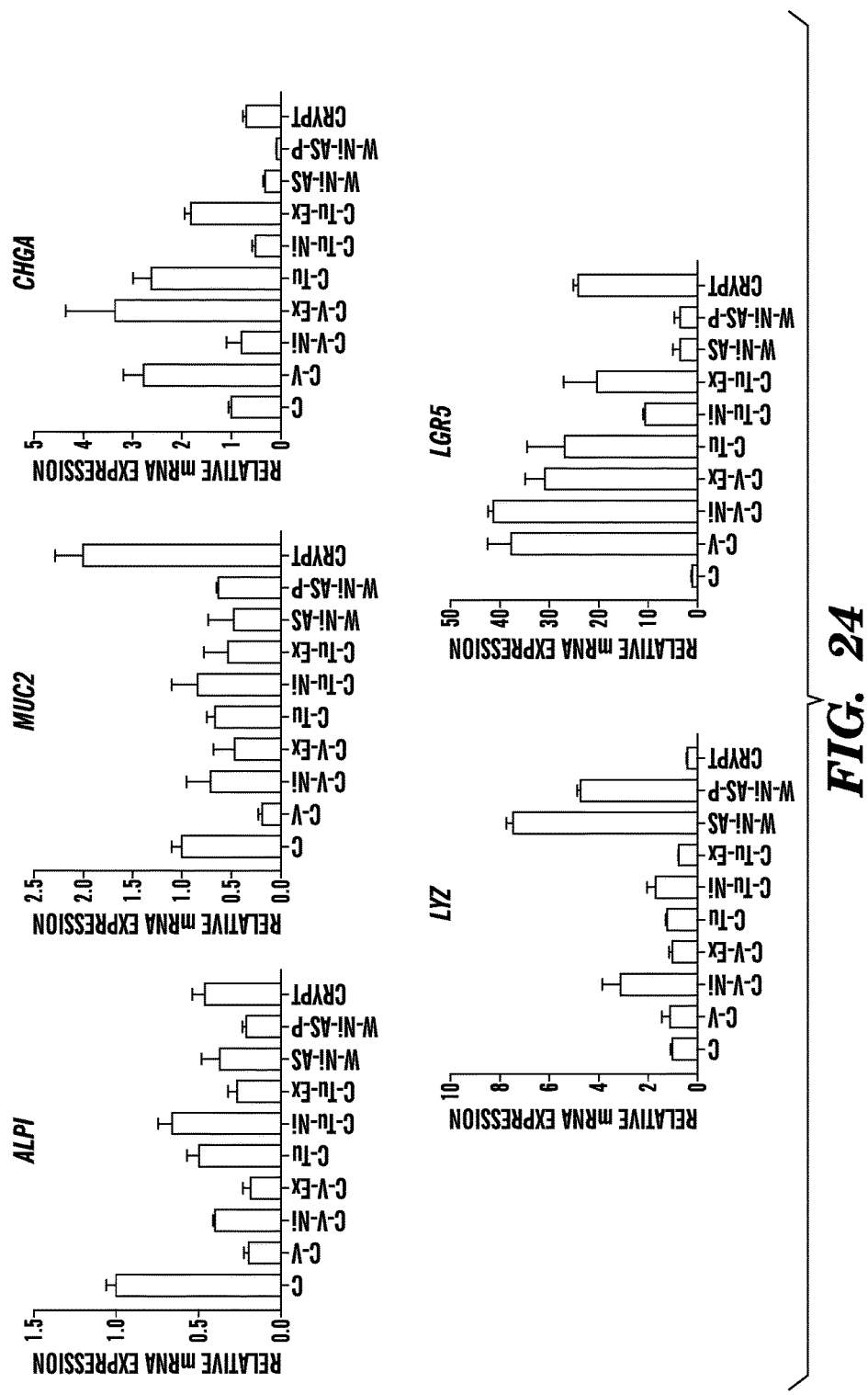
FIG. 24 depicts real-time RT-PCR analysis of marker gene expression of isolated human intestinal crypts cultured in multiple conditions. EGF, Noggin and R-spondin1 were added to all conditions. C: CHIR, Ni: Nicotinamide, W: Wnt3a, A: A83-01, S: SB202190, P: PGE2, V: VPA, Tu: Tubastatin A, Crypt indicates freshly isolated human small intestinal crypts. Error bars indicate S.D., n=3.
Figure 25B:
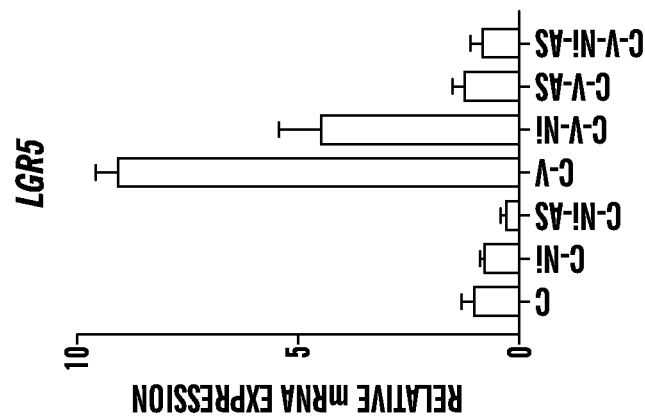
FIGS. 25A-25B depict optimizing culture condition for human intestinal stem cells.
Figure 25A:
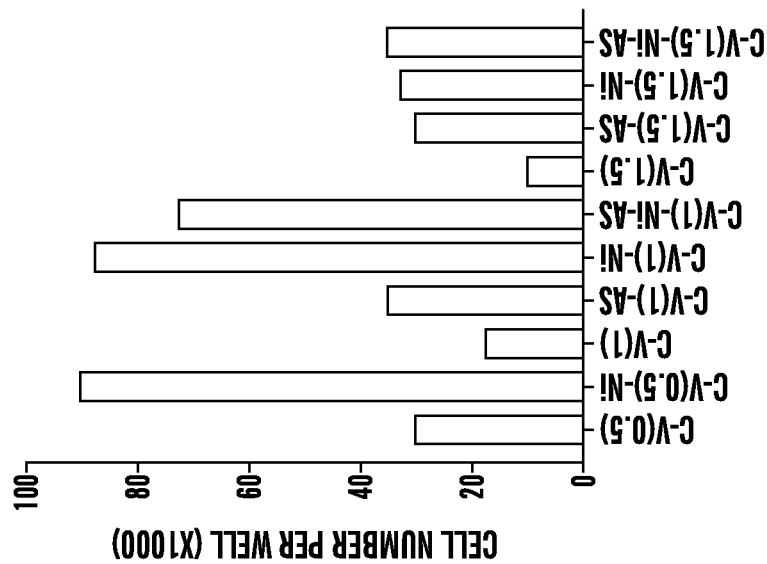
Figure 26:
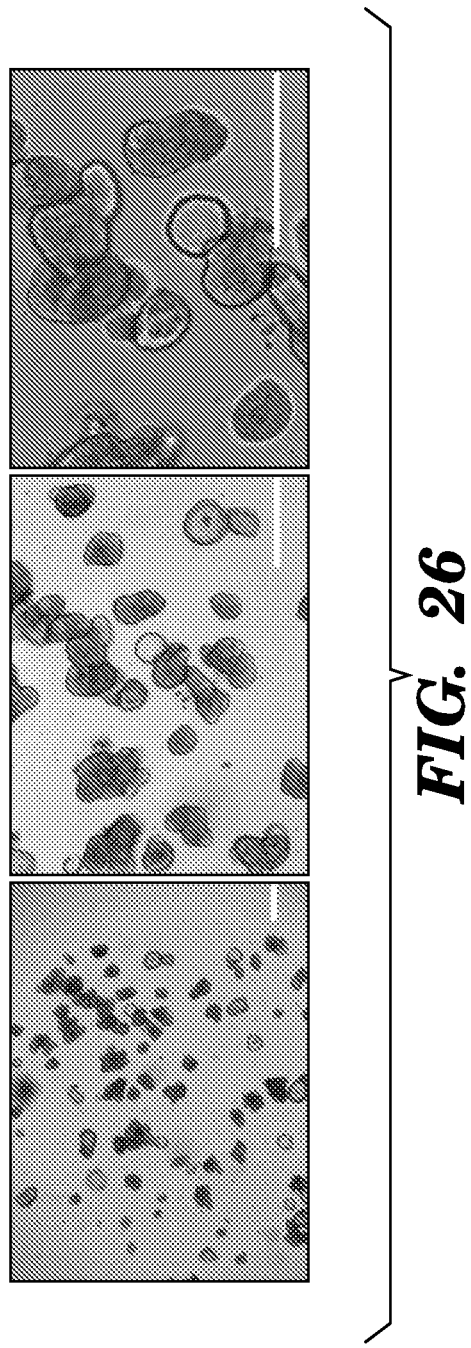
FIG. 26 depicts human intestinal stem cell culture. Cells were cultured in human intestinal stem cell culture media (containing EGF, Noggin, R-Spondin1, CHIR99021, VPA and Nicotinamide). Shown are cells of passage 2 at day 5 after passage. Scale bars: 400 μm.

Similar to the mouse intestinal stem cell culture, the combination of CHIR+VPA or CHIR+Tubastatin A greatly promoted the expression of stem cell marker LGR5, suggesting the cultured cells were enriched in stem cells (FIG. 24). Notably, the culture condition containing CHIR and VPA or CHIR and Tubastatin A outperformed published conditions in promoting LGR5 expression (FIG. 24). In addition, individual components showing improvement to the culture media were tested, including A83-01 (ALK4,5,7, Tgf-β inhibitor), SB202190 (p38 inhibitor) and Nicotinamide (Vitamin B derivative). It was determined that 10 mM Nicotinamide increased the proliferation of human small intestinal crypts when added to the CHIR+VPA condition, as indicated by the increased cell number in the culture (FIG. 25A), without great impact on LGR5 expression (FIG. 25B). While the combination of A83-01 and SB202190 (AS) increased the proliferation of cells (FIG. 25A), they greatly decreased the expression of LGR5 (FIG. 25B). In addition, a lower concentration of VPA (0.5 mM, compared to that used in mouse cultures (1-2 mM)) increased cell proliferation of human small intestinal crypts (FIG. 25A). Collectively, it was determined that the culture condition containing EGF, Noggin, R-spondin1, CHIR, VPA (0.5 mM) and Nicotinamide or EX527 was an optimal culture condition for human intestinal stem cells. In this condition, isolated small intestinal crypts grow into colonies comparable to mouse small intestinal stem cells (FIG. 26).

Example 10

Figure 27:
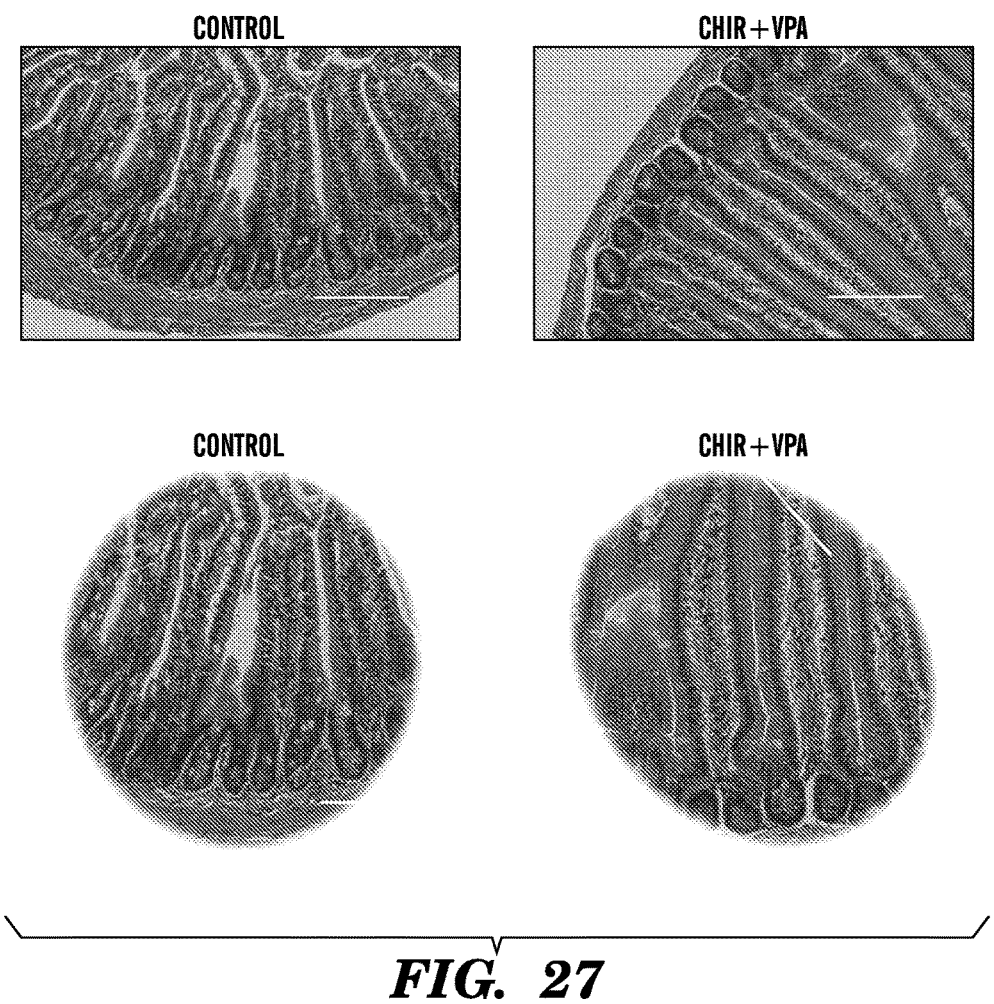
FIG. 27 depicts increased crypt size following administration of CHIR and VPA over the course of 7 days in vivo in an animal model system.

To test the in vivo effect of CHIR and VPA on intestinal epithelial cells, CHIR99021 (30 mg/Kg in 100 μl DMSO) and VPA (200 mg/Kg in 100 μl water) were administered to 4-6 week old female Lgr5-GFP mice via gavage. Control mice were given a mixture of 100 μl DMSO and 100 μl water. Drugs were administered every 48 hours for 7 days (at Day 0, Day 2, Day 4 and Day 6). At Day 7, mice were sacrificed and intestine tissue were collected. The small intestine were further washed with PBS, fixed with 4% PFA for 12 hours, embedded in Paraffin and stained using standard Hematoxylin and eosin (H&E) staining protocol. Images were acquired using an inverted microscope (EVOS, Advanced Microscopy Group). In vivo administration of CHIR and VPA increased the size of crypts following 3 administrations over the course of 7 days (FIG. 27).

REFERENCES

All patents, patent applications and publications mentioned in this specification are herein incorporated by reference to the same extent as if each independent patent and publication was specifically and individually indicated to be incorporated by reference.

Abreu, J. G., Ketpura, N. I., Reversade, B., and De Robertis, E. M. (2002). Connective-tissue growth factor (CTGF) modulates cell signalling by BMP and TGF-beta. Nat Cell Biol 4, 599-604.

Alessi, D. R., A. Cuenda, P. Cohen, D. T. Dudley and A. R. Saltiel (1995). PD 098059 is a specific inhibitor of the activation of mitogen-activated protein kinase kinase in vitro and in vivo. J Biol Chem 270(46): 27489-27494.

Anastassiadis, T., K. C. Duong-Ly, S. W. Deacon, A. Lafontant, H. Ma, K. Devarajan, R. L. Dunbrack, Jr., J. Wu and J. R. Peterson (2013). A highly selective dual insulin receptor (IR)/insulin-like growth factor 1 receptor (IGF-1R) inhibitor derived from an extracellular signal-regulated kinase (ERK) inhibitor. J Biol Chem 288(39): 28068-28077.

Anderson, J. J., G. Holtz, P. P. Baskin, M. Turner, B. Rowe, B. Wang, M. Z. Kounnas, B. T. Lamb, D. Barten, K. Felsenstein, I. McDonald, K. Srinivasan, B. Munoz and S. L. Wagner (2005). Reductions in beta-amyloid concentrations in vivo by the gamma-secretase inhibitors BMS-289948 and BMS-299897. Biochem Pharmacol 69(4): 689-698.

Andreani, A., Cavalli, A., Granaiola, M., Leoni, A., Locatelli, A., Morigi, R., Meijer, L. (2000). Imidazo[2,1-b] thiazolylmethylene- and indolylmethylene-2-indolinones: a new class of cyclin-dependent kinase inhibitors. Design, synthesis, and CDK1/cyclin B inhibition. Anti-cancer drug design, 15(6), 447-452.

Andreani, A., Locatelli, A., Rambaldi, M., Leoni, A., Bossa, R., Fraccari, A., and Galatulas, I. (1996). Potential antitumor agents. 25 [1]. Synthesis and cytotoxic activity of 3-(2-chloro-3-indolylmethylene)1,3-dihydroindol-2-ones. Anticancer research, 16(6B), 3585-3588.

Bain, J., Plater, L., Elliott, M., Shpiro, N., Hastie, C. J., McLauchlan, H., Klevernic, I., Arthur, J. S., Alessi, D. R., and Cohen, P. (2007). The selectivity of protein kinase inhibitors: a further update. The Biochemical journal 408, 297-315.

Badylak, S. F., et al. (1989). Small intestinal submucosa as a large diameter vascular graft in the dog. The Journal of Surgical Research 47(1): p. 74-80.

Bakshi, P., C. Jin, P. Broutin, B. Berhane, J. Reed and M. Mullan (2009). Structural optimization of a CXCR2-directed antagonist that indirectly inhibits gamma-secretase and reduces Abeta. Bioorg Med Chem 17(23): 8102-8112.

Barker, N., van Es, J. H., Kuipers, J., Kujala, P., van den Born, M., Cozijnsen, M., Haegebarth, A., Korving, J., Begthel, H., Peters, P. J., et al. (2007). Identification of stem cells in small intestine and colon by marker gene Lgr5. Nature 449, 1003-1007.

Bax, B., Carter, P. S., Lewis, C., Guy, A. R., Bridges, A., Tanner, R., and Reith, A. D. (2001). The Structure of Phosphorylated GSK-3β Complexed with a Peptide, FRATtide, that Inhibits β-Catenin Phosphorylation. Structure, 9(12), 1143-1152. doi:10.1016/S0969-2126(01)00679-7.

Bhat, R., Xue, Y., Berg, S., Hellberg, S., Ormo, M., Nilsson, Y., Radesater, A. C., Jerning, E., Markgren, P. O., Borgegard, T., et al. (2003). Structural insights and biological effects of glycogen synthase kinase 3-specific inhibitor AR-A014418. J Biol Chem 278, 45937-45945.

Baumert, H., et al. (2007). Development of a seeded scaffold in the great omentum: feasibility of an in vivo. Eur Urol 52(3): p. 884-90.

Baumert, H., et al. (2007). Terminal urothelium differentiation of engineered neoureter after in vivo. Eur Urol 52(5): p. 1492-8.

Bergstein, I., Eisenberg, L. M., Bhalerao, J., Jenkins, N. A., Copeland, N. G., Osborne, M. P. and Brown, A. M. (1997). Isolation of two novel WNT genes, WNT14 and WNT15, one of which (WNT15) is closely linked to WNT3 on human chromosome 17q21. Genomics, 46(3), 450-458. doi:10.1006/geno.1997.5041

Breton, J. J., & Chabot-Fletcher, M. C. (1997). The natural product hymenialdisine inhibits interleukin-8 production in U937 cells by inhibition of nuclear factor-kappaB. The Journal of pharmacology and experimental therapeutics, 282(1), 459-466.

Burrus, L. W., & McMahon, A. P. (1995). Biochemical analysis of murine Wnt proteins reveals both shared and distinct properties. Experimental cell research, 220(2), 363-373. doi:10.1006/excr.1995.1327

Bodine, P. V., Stauffer, B., Ponce-de-Leon, H., Bhat, R. A., Mangine, A., Seestaller-Wehr, L. M., Moran, R. A., Billiard, J., Fukayama, S., Komm, B. S., et al. (2009). A small molecule inhibitor of the Wnt antagonist secreted frizzled-related protein-1 stimulates bone formation. Bone 44, 1063-1068.

Buczacki S J, Zecchini H I, Nicholson A M, Russell R, Vermeulen L, Kemp R, and Winton D J. (2013) Intestinal label-retaining cells are secretory precursors expressing Lgr5. Nature. 2013 Feb. 27. doi: 10.1038/nature11965. [Epub ahead of print].

Campodonico, F., et al. (2004). Bladder cell culture on small intestinal submucosa as bioscaffold: experimental. Eur Urol 46(4): p. 531-7.

Chen, B., M. E. Dodge, W. Tang, J. Lu, Z. Ma, C. W. Fan, S. Wei, W. Hao, J. Kilgore, N. S. Williams, M. G. Roth, J F Amatruda, C. Chen and L. Lum (2009). Small molecule-mediated disruption of Wnt-dependent signaling in tissue regeneration and cancer. Nat Chem Biol 5(2): 100-107.

Chen, S., T. Operana, J. Bonzo, N. Nguyen and R. H. Tukey (2005). ERK kinase inhibition stabilizes the aryl hydrocarbon receptor: implications for transcriptional activation and protein degradation. J Biol Chem 280(6): 4350-4359.

Chen W, Gaisina I N, Gunosewoyo H, Malekiani S A, Hanania T, Kozikowski A P (2011) Structure-guided design of a highly selective glycogen synthase kinase-3beta inhibitor: a superior neuroprotective pyrazolone showing antimania effects. ChemMedChem 6: 1587-1592.

Ciardiello, F. (2000). Epidermal growth factor receptor tyrosine kinase inhibitors as anticancer agents. Drugs 60 Suppl 1: 25-32; discussion 41-22.

Coghlan, M. P., Culbert, A. A., Cross, D. A., Corcoran, S. L., Yates, J. W., Pearce, N.J., Rausch, O. L., Murphy, G. J., Carter, P. S., Roxbee Cox, L., et al. (2000). Selective small molecule inhibitors of glycogen synthase kinase-3 modulate glycogen metabolism and gene transcription. Chemistry & biology 7, 793-803.

Crosnier, C., Stamataki, D., and Lewis, J. (2006). Organizing cell renewal in the intestine: stem cells, signals and combinatorial control. Nature Reviews Genetics 7, 349-359.

Cuny, G. D., Yu, P. B., Laha, J. K., Xing, X., Liu, J. F., Lai, C. S., Deng, D. Y., Sachidanandan, C., Bloch, K. D., and Peterson, R. T. (2008). Structure-activity relationship study of bone morphogenetic protein (BMP) signaling inhibitors. Bioorganic & medicinal chemistry letters 18, 4388-4392.

de la Fuente, S. G., et al., (2003) Evaluation of porcine-derived small intestine submucosa as a biodegradable graft for gastrointestinal healing. Journal of gastrointestinal surgery: official journal of the Society for Surgery of the Alimentary Tract. 7(1): p. 96-101.

De Rybel, B., Audenaert, D., Vert, G., Rozhon, W., Mayerhofer, J., Peelman, F., and Beeckman, T. (2009). Chemical inhibition of a subset of *Arabidopsis thaliana* GSK3-like kinases activates brassinosteroid signaling. Chemistry & biology, 16(6), 594-604. doi:10.1016/j.chembiol.2009.04.008

Ding, S., Wu, T. Y., Brinker, A., Peters, E. C., Hur, W., Gray, N. S., and Schultz, P. G. (2003). Synthetic small molecules that control stem cell fate. Proc Natl Acad Sci USA 100, 7632-7637.

Dong, Q., D. R. Dougan, X. Gong, P. Halkowycz, B. Jin, T. Kanouni, S. M. O'Connell, N. Scorah, L. Shi, M. B. Wallace and F. Zhou (2011). Discovery of TAK-733, a potent and selective MEK allosteric site inhibitor for the treatment of cancer. Bioorg Med Chem Left 21(5): 1315-1319.

Dovey, H. F., V. John, J. P. Anderson, L. Z. Chen, P. de Saint Andrieu, L. Y. Fang, S. B. Freedman, B. Folmer, E. Goldbach, E. J. Holsztynska, K. L. Hu, K. L. Johnson-Wood, S. L. Kennedy, D. Kholodenko, J. E. Knops, L. H. Latimer, M. Lee, Z. Liao, I. M. Lieberburg, R. N. Motter, L. C. Mutter, J. Nietz, K. P. Quinn, K. L. Sacchi, P. A. Seubert, G. M. Shopp, E. D. Thorsett, J. S. Tung, J. Wu, S. Yang, C. T. Yin, D. B. Schenk, P. C. May, L. D. Altstiel, M. H. Bender, L. N. Boggs, T. C. Britton, J. C. Clemens, D. L. Czilli, D. K. Dieckman-McGinty, J. J. Droste, K. S. Fuson, B. D. Gitter, P. A. Hyslop, E. M. Johnstone, W. Y. Li, S. P. Little, T. E. Mabry, F. D. Miller and J. E. Audia (2001). Functional gamma-secretase inhibitors reduce beta-amyloid peptide levels in brain. J Neurochem 76(1): 173-181.

Durand, A., Donahue, B., Peignon, G., Letourneur, F., Cagnard, N., Slomianny, C., Perret, C., Shroyer, N. F., and Romagnolo, B. (2012). Functional intestinal stem cells after Paneth cell ablation induced by the loss of transcription factor Math1 (Atoh1). Proceedings of the National Academy of Sciences of the United States of America.

Favata, M. F., K. Y. Horiuchi, E. J. Manos, A. J. Daulerio, D. A. Stradley, W. S. Feeser, D. E. Van Dyk, W. J. Pitts, R. A. Earl, F. Hobbs, R. A. Copeland, R. L. Magolda, P. A. Scherle and J. M. Trzaskos (1998). Identification of a novel inhibitor of mitogen-activated protein kinase kinase. J Biol Chem 273(29): 18623-18632.

Fear, M. W., Kelsell, D. P., Spurr, N. K., & Barnes, M. R. (2000). Wnt-16a, a novel Wnt-16 isoform, which shows differential expression in adult human tissues. Biochemical and biophysical research communications, 278(3), 814-820. doi:10.1006/bbrc.2000.3852.

Feil, G., et al. (2006). Investigations of urothelial cells seeded on commercially available small. Eur Urol 50(6): p. 1330-7.

Farin, H. F., Van Es, J. H., and Clevers, H. (2012). Redundant sources of Wnt regulate intestinal stem cells and promote formation of Paneth cells. Gastroenterology 143, 1518-1529 e1517.

Garner, L. W., Nove, J., Levin, M., and Rosen, V. (2005). BMP-3 is a novel inhibitor of both activin and BMP-4 signaling in *Xenopus* embryos. Dev Biol 285, 156-168.

Gazit, A., P. Yaish, C. Gilon and A. Levitzki (1989). Tyrphostins I: synthesis and biological activity of protein tyrosine kinase inhibitors. J Med Chem 32(10): 2344-2352.

Gilbert, A. M., Bursavich, M. G., Alon, N., Bhat, B. M., Bex, F. J., Cain, M., Coleburn, V., Gironda, V., Green, P., Hauze, D. B., et al. (2010). Hit to lead studies on (hetero)arylpyrimidines-agonists of the canonical Wnt-beta-catenin cellular messaging system. Bioorganic & medicinal chemistry letters 20, 366-370.

Gilmartin, A. G., M. R. Bleam, A. Groy, K. G. Moss, E. A. Minthorn, S. G. Kulkarni, C. M. Rominger, S. Erskine, K. E. Fisher, J. Yang, F. Zappacosta, R. Annan, D. Sutton and S. G. Laquerre (2011). GSK1120212 (JTP-74057) is an inhibitor of MEK activity and activation with favorable pharmacokinetic properties for sustained in vivo pathway inhibition. Clin Cancer Res 17(5): 989-1000.

Greenblatt, D. Y., Vaccaro, A. M., Jaskula-Sztul, R., Ning, L., Haymart, M., Kunnimalaiyaan, M., and Chen, H. (2007). Valproic acid activates notch-1 signaling and regulates the neuroendocrine phenotype in carcinoid cancer cells. The oncologist 12, 942-951.

Gupta, A., et al. (2006). Tissue engineering of small intestine-current status. Biomacromolecules, 2006. 7(10): p. 2701-2709.

Handeli, S. and J. A. Simon (2008). A small-molecule inhibitor of Tcf/beta-catenin signaling down-regulates PPARgamma and PPARdelta activities. Mol Cancer Ther 7(3): 521-529.

Hao, J., Ho, J. N., Lewis, J. A., Karim, K. A., Daniels, R. N., Gentry, P. R., Hopkins, C. R., Lindsley, C. W., and Hong, C. C. (2010). In vivo structure-activity relationship study of dorsomorphin analogues identifies selective VEGF and BMP inhibitors. ACS chemical biology 5, 245-253.

He, W., L. Luistro, D. Carvajal, M. Smith, T. Nevins, X. Yin, J. Cai, B. Higgins, K. Kolinsky, C. Rizzo, K. Packman, D. Heimbrook and J. F. Boylan (2011). High tumor levels of IL6 and IL8 abrogate preclinical efficacy of the gamma-secretase inhibitor, RO4929097. Mol Oncol 5(3): 292-301.

Huang, F., A. Greer, W. Hurlburt, X. Han, R. Hafezi, G. M. Wittenberg, K. Reeves, J. Chen, D. Robinson, A. Li, F. Y. Lee, M. M. Gottardis, E. Clark, L. Helman, R. M. Attar, A. Dongre and J. M. Carboni (2009). The mechanisms of differential sensitivity to an insulin-like growth factor-1 receptor inhibitor (BMS-536924) and rationale for combining with EGFR/HER2 inhibitors. Cancer Res 69(1): 161-170.

Huynh, H., K. C. Soo, P. K. Chow and E. Tran (2007). Targeted inhibition of the extracellular signal-regulated kinase kinase pathway with AZD6244 (ARRY-142886) in the treatment of hepatocellular carcinoma. Mol Cancer Ther 6(1): 138-146.

Jung, P., Sato, T., Merlos-Suarez, A., Barriga, F. M., Iglesias, M., Rossell, D., Auer, H., Gallardo, M., Blasco, M. A., Sancho, E., et al. (2011). Isolation and in vitro expansion of human colonic stem cells. Nat Med 17, 1225-1227.

Kazanjian, A., Noah, T., Brown, D., Burkart, J., and Shroyer, N. F. (2010). Atonal homolog 1 is required for growth and differentiation effects of notch/gamma-secretase inhibitors on normal and cancerous intestinal epithelial cells. Gastroenterology 139, 918-928, 928 e911-916.

Katoh, M, Hirai, M., Sugimura, T., & Terada, M. (1996). Cloning, expression and chromosomal localization of Wnt-13, a novel member of the Wnt gene family. Oncogene, 13(4), 873-876.

Katoh, Masaru. (2001). Molecular cloning and characterization of human WNT3. International Journal of Oncology, 19(5), 977.

Katoh, Masaru. (2011). Network of WNT and other regulatory signaling cascades in pluripotent stem cells and cancer stem cells. Current pharmaceutical biotechnology, 12(2), 160-170.

Khanfar, M. A., Hill, R. A., Kaddoumi, A., and El Sayed, K. A. (2010). Discovery of novel GSK-3beta inhibitors with potent in vitro and in vivo activities and excellent brain permeability using combined ligand- and structure-based virtual screening. Journal of medicinal chemistry 53, 8534-8545.

Kim, K. A., Zhao, J., Andarmani, S., Kakitani, M., Oshima, T., Binnerts, M. E., Abo, A., Tomizuka, K., and Funk, W. D. (2006). R-Spondin proteins: a novel link to beta-catenin activation. Cell Cycle 5, 23-26.

Kim, K., S. Y. Kong, M. Fulciniti, X. Li, W. Song, S. Nahar, P. Burger, M. J. Rumizen, K. Podar, D. Chauhan, T. Hideshima, N. C. Munshi, P. Richardson, A. Clark, J. Ogden, A. Goutopoulos, L. Rastelli, K. C. Anderson and Y. T. Tai (2010). Blockade of the MEK/ERK signalling cascade by AS703026, a novel selective MEK1/2 inhibitor, induces pleiotropic anti-myeloma activity in vitro and in vivo. Br J Haematol 149(4): 537-549.

Kim, T. H., Escudero, S., and Shivdasani, R. A. (2012). Intact function of Lgr5 receptor-expressing intestinal stem cells in the absence of Paneth cells. Proceedings of the National Academy of Sciences of the United States of America 109, 3932-3937.

Kim, T. H., and Shivdasani, R. A. (2011). Genetic evidence that intestinal Notch functions vary regionally and operate through a common mechanism of Math1 repression. J Biol Chem 286, 11427-11433.

Kehoe, S., X. F. Zhang, and D. Boyd (2012) FDA approved guidance conduits and wraps for peripheral nerve injury: A review of materials and efficacy. Injury. 43(5): p. 553-572.

Klein, P. S., & Melton, D. A. (1996). A molecular mechanism for the effect of lithium on development. Proceedings of the National Academy of Sciences, 93(16), 8455-8459.

Koizumi, Y., N. Kawashima, M. Yamamoto, K. Takimoto, M. Zhou, N. Suzuki, M. Saito, H. Harada and H. Suda (2013). Wnt11 expression in rat dental pulp and promotional effects of Wnt signaling on odontoblast differentiation. Congenit Anom (Kyoto) 53(3): 101-108.

Kuiper, J. L., D. A. Heideman, E. Thunnissen, A. W. van Wijk, P. E. Postmus and E. F. Smit (2014). High-dose, weekly erlotinib is not an effective treatment in EGFRmutated non-small cell lung cancer-patients with acquired extracranial progressive disease on standard dose erlotinib. Eur J Cancer.

Lako, M., Lindsay, S., Bullen, P., Wilson, D. I., Robson, S. C., & Strachan, T. (1998). A novel mammalian wnt gene, WNT8B, shows brain-restricted expression in early development, with sharply delimited expression boundaries in the developing forebrain. Human molecular genetics, 7(5), 813-822.

Lako, M., Strachan, T., Bullen, P., Wilson, D. I., Robson, S. C., & Lindsay, S. (1998). Isolation, characterisation and embryonic expression of WNT11, a gene which maps to 11q13.5 and has possible roles in the development of skeleton, kidney and lung. Gene, 219(1-2), 101-110.

Lanz, T. A., J. D. Hosley, W. J. Adams and K. M. Merchant (2004). Studies of Abeta pharmacodynamics in the brain, cerebrospinal fluid, and plasma in young (plaque-free) Tg2576 mice using the gamma-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY-411575). J Pharmacol Exp Ther 309(1): 49-55.

Lazarova, D. L., C. Chiaro, T. Wong, E. Drago, A. Rainey, S. O'Malley and M. Bordonaro (2013). CBP Activity Mediates Effects of the Histone Deacetylase Inhibitor Butyrate on WNT Activity and Apoptosis in Colon Cancer Cells. J Cancer 4(6): 481-490.

Li H, Liu H, Heller S. (2003). Pluripotent stem cells from the adult mouse inner ear. Nat Med. October; 9(10):1293-9.

Lien, W. H., L. Polak, M. Lin, K. Lay, D. Zheng and E. Fuchs (2014). In vivo transcriptional governance of hair follicle stem cells by canonical Wnt regulators. Nat Cell Biol 16(2): 179-190.

Liu, J., S. Pan, M. H. Hsieh, N. Ng, F. Sun, T. Wang, S. Kasibhatla, A. G. Schuller, A. G. Li, D. Cheng, J. Li, C. Tompkins, A. Pferdekamper, A. Steffy, J. Cheng, C. Kowal, V. Phung, G. Guo, Y. Wang, M. P. Graham, S. Flynn, J. C. Brenner, C. Li, M. C. Villarroel, P. G. Schultz, X. Wu, P. McNamara, W. R. Sellers, L. Petruzzelli, A. L. Boral, H. M. Seidel, M. E. McLaughlin, J. Che, T. E. Carey, G. Vanasse and J. L. Harris (2013). Targeting Wnt-driven cancer through the inhibition of Porcupine by LGK974. Proc Natl Acad Sci USA 110(50): 20224-20229.

Liu, J., Wu, X., Mitchell, B., Kintner, C., Ding, S., and Schultz, P. G. (2005). A small-molecule agonist of the Wnt signaling pathway. Angew Chem Int Ed Engl 44, 1987-1990.

Lloyd, D. A. J., et al. (2006). A pilot study investigating a novel subcutaneously implanted pre-cellularised scaffold for tissue engineering of intestinal mucosa. European cells & materials, 11: p. 27-33; discussion 34.

Lukacs R U, Goldstein A S, Lawson D A, Cheng D, Witte O N. (2010) Isolation, cultivation and characterization of adult murine prostate stem cells. Nat Protoc. 5(4):702-13.

Mariadason, J. M. (2008). HDACs and HDAC inhibitors in colon cancer. Epigenetics: official journal of the DNA Methylation Society 3, 28-37.

Meijer, L., Skaltsounis, A. L., Magiatis, P., Polychronopoulos, P., Knockaert, M., Leost, M., Ryan, X. P., Vonica, C. A., Brivanlou, A., Dajani, R., et al. (2003). GSK-3-selective inhibitors derived from Tyrian purple indirubins. Chemistry & biology 10, 1255-1266.

Milano, J., McKay, J., Dagenais, C., Foster-Brown, L., Pognan, F., Gadient, R., Jacobs, R. T., Zacco, A., Greenberg, B., and Ciaccio, P. J. (2004). Modulation of notch processing by gamma-secretase inhibitors causes intestinal goblet cell metaplasia and induction of genes known to specify gut secretory lineage differentiation. Toxicological sciences: an official journal of the Society of Toxicology 82, 341-358.

Minami, I., K. Yamada, T. G. Otsuji, T. Yamamoto, Y. Shen, S. Otsuka, S. Kadota, N. Morone, M. Barve, Y. Asai, T. Tenkova-Heuser, J. E. Heuser, M. Uesugi, K. Aiba and N. Nakatsuji (2012). A small molecule that promotes cardiac differentiation of human pluripotent stem cells under defined, cytokine- and xeno-free conditions. Cell Rep 2(5): 1448-1460.

Minkovsky, N. and A. Berezov (2008). BIBW-2992, a dual receptor tyrosine kinase inhibitor for the treatment of solid tumors. Curr Opin Investig Drugs 9(12): 1336-1346.

Montgomery, R. K., Carlone, D. L., Richmond, C. A., Farilla, L., Kranendonk, M. E., Henderson, D. E., Baffour-Awuah, N.Y., Ambruzs, D. M., Fogli, L. K., Algra, S., et al. (2011). Mouse telomerase reverse transcriptase (mTert) expression marks slowly cycling intestinal stem cells. Proceedings of the National Academy of Sciences of the United States of America 108, 179-184.

Miyabayashi, T., Teo, J. L., Yamamoto, M., McMillan, M., Nguyen, C., and Kahn, M. (2007). Wnt/beta-catenin/CBP signaling maintains long-term murine embryonic stem cell pluripotency. Proc Natl Acad Sci USA 104, 5668-5673.

Nam, J. S., Turcotte, T. J., Smith, P. F., Choi, S., and Yoon, J. K. (2006). Mouse cristin/R-spondin family proteins are novel ligands for the Frizzled 8 and LRP6 receptors and activate beta-catenin-dependent gene expression. J Biol Chem 281, 13247-13257.

Nusse, R., & Varmus, H. E. (1982). Many tumors induced by the mouse mammary tumor virus contain a provirus integrated in the same region of the host genome. Cell, 31(1), 99-109.

Ohori, M., T. Kinoshita, M. Okubo, K. Sato, A. Yamazaki, H. Arakawa, S. Nishimura, N. Inamura, H. Nakajima, M. Neya, H. Miyake and T. Fujii (2005). Identification of a selective ERK inhibitor and structural determination of the inhibitor-ERK2 complex. Biochem Biophys Res Commun 336(1): 357-363.

Ootani, A., Li, X., Sangiorgi, E., Ho, Q. T., Ueno, H., Toda, S., Sugihara, H., Fujimoto, K., Weissman, I. L., Capecchi, M. R., et al. (2009). Sustained in vitro intestinal epithelial culture within a Wnt-dependent stem cell niche. Nat Med 15, 701-706.

Pai, R., Tarnawski, A. S., and Tran, T. (2004). Deoxycholic acid activates beta-catenin signaling pathway and increases colon cell cancer growth and invasiveness. Molecular biology of the cell 15, 2156-2163.

Pellegrinet, L., Rodilla, V., Liu, Z., Chen, S., Koch, U., Espinosa, L., Kaestner, K. H., Kopan, R., Lewis, J., and Radtke, F. (2011). Dll1- and dll4-mediated notch signaling are required for homeostasis of intestinal stem cells. Gastroenterology 140, 1230-1240 e1231-1237.

Planutis, K., Planutiene, M., Moyer, M. P., Nguyen, A. V., Perez, C. A., and Holcombe, R. F. (2007). Regulation of norrin receptor frizzled-4 by Wnt2 in colon-derived cells. BMC cell biology 8, 12.

Powell, D. W., Pinchuk, I. V., Saada, J. I., Chen, X., and Mifflin, R. C. (2011). Mesenchymal cells of the intestinal lamina propria. Annual review of physiology 73, 213-237.

Proffitt, K. D., B. Madan, Z. Ke, V. Pendharkar, L. Ding, M. A. Lee, R. N. Hannoush and D. M. Virshup (2013). Pharmacological inhibition of the Wnt acyltransferase PORCN prevents growth of WNT-driven mammary cancer. Cancer Res 73(2): 502-507.

Riccio, O., van Gijn, M. E., Bezdek, A. C., Pellegrinet, L., van Es, J. H., Zimber-Strobl, U., Strobl, L. J., Honjo, T., Clevers, H., and Radtke, F. (2008). Loss of intestinal crypt progenitor cells owing to inactivation of both Notch1 and Notch2 is accompanied by derepression of CDK inhibitors p27Kip1 and p57Kip2. EMBO Rep 9, 377-383.

Rider, C. C., and Mulloy, B. (2010). Bone morphogenetic protein and growth differentiation factor cytokine families and their protein antagonists. Biochem J 429, 1-12.

Ring, D. B., Johnson, K. W., Henriksen, E. J., Nuss, J. M., Goff, D., Kinnick, T. R., Ma, S. T., Reeder, J. W., Samuels, I., Slabiak, T., et al. (2003). Selective glycogen synthase kinase 3 inhibitors potentiate insulin activation of glucose transport and utilization in vitro and in vivo. Diabetes 52, 588-595.

Saito, N., J. Fu, S. Zheng, J. Yao, S. Wang, D. D. Liu, Y. Yuan, E. P. Sulman, F. F. Lang, H. Colman, R. G. Verhaak, W. K. Yung and D. Koul (2014). A high Notch pathway activation predicts response to gamma secretase inhibitors in proneural subtype of glioma tumor-initiating cells. Stem Cells 32(1): 301-312.

Sangiorgi, E., and Capecchi, M. R. (2008). Bmi1 is expressed in vivo in intestinal stem cells. Nature genetics 40, 915-920.

Sakuma, Y., Y. Yamazaki, Y. Nakamura, M. Yoshihara, S. Matsukuma, H. Nakayama, T. Yokose, Y. Kameda, S. Koizume and Y. Miyagi (2012). WZ4002, a third-generation EGFR inhibitor, can overcome anoikis resistance in EGFR-mutant lung adenocarcinomas more efficiently than Src inhibitors. Lab Invest 92(3): 371-383.

Sato, T., Stange, D. E., Ferrante, M., Vries, R. G., Van Es, J. H., Van den Brink, S., Van Houdt, W. J., Pronk, A., Van Gorp, J., Siersema, P. D., et al. (2011a). Long-term expansion of epithelial organoids from human colon, adenoma, adenocarcinoma, and Barrett's epithelium. Gastroenterology 141, 1762-1772.

Sato, T., van Es, J. H., Snippert, H. J., Stange, D. E., Vries, R. G., van den Born, M., Barker, N., Shroyer, N. F., van de Wetering, M., and Clevers, H. (2011b). Paneth cells constitute the niche for Lgr5 stem cells in intestinal crypts. Nature 469, 415-418.

Sato, T., Vries, R. G., Snippert, H. J., van de Wetering, M., Barker, N., Stange, D. E., van Es, J. H., Abo, A., Kujala, P., Peters, P. J., et al. (2009). Single Lgr5 stem cells build crypt-villus structures in vitro without a mesenchymal niche. Nature 459, 262-265.

Saitoh, M., Kunitomo, J., Kimura, E., Iwashita, H., Uno, Y., Onishi, T., Uchiyama, N., Kawamoto, T., Tanaka, T., Mol, C. D., et al. (2009). 2-{3-[4-(Alkylsulfinyl)phenyl]-1-benzofuran-5-yl}-5-methyl-1,3,4-oxadiazole derivatives as novel inhibitors of glycogen synthase kinase-3beta with good brain permeability. Journal of medicinal chemistry 52, 6270-6286.

Saitoh, T., Hirai, M., & Katoh, M. (2001). Molecular cloning and characterization of WNT3A and WNT14 clustered in human chromosome 1q42 region. Biochemical and biophysical research communications, 284(5), 1168-1175. doi:10.1006/bbrc.2001.5105

Saitoh, T., & Katoh, M. (2001). Molecular cloning and characterization of human WNT8A. International journal of oncology, 19(1), 123-127.

Schneyer, A. L., Rzucidlo, D. A., Sluss, P. M., and Crowley, W. F., Jr. (1994). Characterization of unique binding kinetics of follistatin and activin or inhibin in serum. Endocrinology 135, 667-674.

Schultz, C., Link, A., Leost, M., Zaharevitz, D. W., Gussio, R., Sausville, E. A., Meijer, L., and Kunick, C. (1999). Paullones, a series of cyclin-dependent kinase inhibitors: synthesis, evaluation of CDK1/cyclin B inhibition, and in vitro antitumor activity. Journal of medicinal chemistry 42, 2909-2919.

Scoville, D. H., Sato, T., He, X. C., and Li, L. (2008). Current view: intestinal stem cells and signaling. Gastroenterology 134, 849-864.

Seidi, A., et al., (2011). Gradient biomaterials for soft-to-hard interface tissue engineering. Acta Biomaterialia, 7(4): p. 1441-1451.

Shi, F., Kempfle, J. S., and Edge, A. S. (2012). Wnt-responsive Lgr5-expressing stem cells are hair cell progenitors in the cochlea. J Neurosci. 32, 9639-9648.

Shi F, Cheng Y F, Wang X L, Edge A S. (2010) Beta-catenin up-regulates Atoh1 expression in neural progenitor cells by interaction with an Atoh1 3' enhancer. J Biol Chem. 285(1):392-400.

Snippert, H. J., L. G. Van Der Flier, T. Sato, J. H. Van Es, M. Van Den Born, C. Kroon-Veenboer, N. Barker, A. M. Klein, J. Van Rheenen and B. D. Simons (2010). Intestinal crypt homeostasis results from neutral competition between symmetrically dividing Lgr5 stem cells. Cell 143(1): 134-144.

Snippert, H. J., Van Der Flier, L. G., Sato, T., Van Es, J. H., Van Den Born, M., Kroon-Veenboer, C., Barker, N., Klein, A. M., Van Rheenen, J., and Simons, B. D. (2010). Intestinal crypt homeostasis results from neutral competition between symmetrically dividing Lgr5 stem cells. Cell 143, 134-144.

Stockhausen, M. T., Sjolund, J., Manetopoulos, C., and Axelson, H. (2005). Effects of the histone deacetylase inhibitor valproic acid on Notch signalling in human neuroblastoma cells. Br J Cancer 92, 751-759.

Sø, J. B. Y., Kum, C. K., Fernandes, M. L., & Goh, P. (1996). Comparison between laparoscopic and conventional omental patch repair for perforated duodenal ulcer. Surgical Endoscopy, 10, 1060-1063.

Schultz, D. J., et al., (2002) Porcine small intestine submucosa as a treatment for enterocutaneous fistulas. Journal of the American College of Surgeons. 194(4): p. 541-543.

Smolich, B. D., McMahon, J. A., McMahon, A. P., & Papkoff, J. (1993). Wnt family proteins are secreted and associated with the cell surface. Molecular Biology of the Cell, 4(12), 1267-1275.

Takeda, N., Jain, R., LeBoeuf, M. R., Wang, Q., Lu, M. M., and Epstein, J. A. (2011). Interconversion between intestinal stem cell populations in distinct niches. Science 334, 1420-1424.

Thoma, G., Nuninger, F., Falchetto, R., Hermes, E., Tavares, G. A., Vangrevelinghe, E., and Zerwes, H. G. (2011). Identification of a potent Janus kinase 3 inhibitor with high selectivity within the Janus kinase family. Journal of medicinal chemistry 54, 284-288.

Thompson, N. and J. Lyons (2005). Recent progress in targeting the Raf/MEK/ERK pathway with inhibitors in cancer drug discovery. Curr Opin Pharmacol 5(4): 350-356.

Wiater, E., and Vale, W. (2003) Inhibin is an antagonist of bone morphogenetic protein signaling. J Biol Chem 278, 7934-7941.

Ueno, T., et al., (2007) Functional evaluation of the grafted wall with porcine-derived small intestinal submucosa (SIS) to a stomach defect in rats. Surgery. 142(3): p. 376-383.

van der Flier, L. G., and Clevers, H. (2009). Stem cells, self-renewal, and differentiation in the intestinal epithelium. Annual review of physiology 71, 241-260.

van Es, J. H., de Geest, N., van de Born, M., Clevers, H., and Hassan, B. A. (2010). Intestinal stem cells lacking the Math1 tumour suppressor are refractory to Notch inhibitors. Nat Commun 1, 1-5.

van Es, J. H., van Gijn, M. E., Riccio, O., van den Born, M., Vooijs, M., Begthel, H., Cozijnsen, M., Robine, S., Winton, D. J., Radtke, F., et al. (2005). Notch/gamma-secretase inhibition turns proliferative cells in intestinal crypts and adenomas into goblet cells. Nature 435, 959-963.

VanDussen, K. L., Carulli, A. J., Keeley, T. M., Patel, S. R., Puthoff, B. J., Magness, S. T., Tran, I. T., Maillard, I., Siebel, C., Kolterud, A., et al. (2012). Notch signaling modulates proliferation and differentiation of intestinal crypt base columnar stem cells. Development 139, 488-497.

Wada, A. (2009). GSK-3 inhibitors and insulin receptor signaling in health, disease, and therapeutics. Frontiers in bioscience: a journal and virtual library, 14, 1558-1570.

Wainwright, B. J., Scambler, P. J., Stanier, P., Watson, E. K., Bell, G., Wicking, C., . . . Pedersen, P. S. (1988). Isolation of a human gene with protein sequence similarity to human and murine int-1 and the *Drosophila* segment polarity mutant wingless. The EMBO Journal, 7(6), 1743-1748.

Wang, J., & Shackleford, G. M. (1996). Murine Wnt10a and Wnt10b: cloning and expression in developing limbs, face and skin of embryos and in adults. Oncogene, 13(7), 1537-1544.

Watanabe, K., Ueno, M., Kamiya, D., Nishiyama, A., Matsumura, M., Wataya, T., Takahashi, J. B., Nishikawa, S., Muguruma, K., and Sasai, Y. (2007). A ROCK inhibitor permits survival of dissociated human embryonic stem cells. Nature biotechnology 25, 681-686.

Wehner, D., W. Cizelsky, M. D. Vasudevaro, G. Ozhan, C. Haase, B. Kagermeier-Schenk, A. Roder, R. I. Dorsky, E. Moro, F. Argenton, M. Kuhl and G. Weidinger (2014). Wnt/beta-Catenin Signaling Defines Organizing Centers that Orchestrate Growth and Differentiation of the Regenerating Zebrafish Caudal Fin. Cell Rep 6(3): 467-481.

White, P. M., Doetzlhofer, A., Lee, Y. S., Groves, A. K., Seigil, N. (2006). Mammalian cochlear supporting cells can divide and trans-differentiate into hair cells. Nature 441, 984-987.

Wiater, E., and Vale, W. (2003) Inhibin is an antagonist of bone morphogenetic protein signaling. J Biol Chem 278, 7934-7941.

Wong, G. T., Manfra, D., Poulet, F. M., Zhang, Q., Josien, H., Bara, T., Engstrom, L., Pinzon-Ortiz, M., Fine, J. S., Lee, H. J., et al. (2004). Chronic treatment with the gamma-secretase inhibitor LY-411,575 inhibits beta-amyloid peptide production and alters lymphopoiesis and intestinal cell differentiation. J Biol Chem 279, 12876-12882.

Xia, W., R. J. Mullin, B. R. Keith, L. H. Liu, H. Ma, D. W. Rusnak, G. Owens, K. J. Alligood and N. L. Spector (2002). Anti-tumor activity of GW572016: a dual tyrosine kinase inhibitor blocks EGF activation of EGFR/erbB2 and downstream Erkl/2 and AKT pathways. Oncogene 21(41): 6255-6263.

Yang, Q., Bermingham, N. A., Finegold, M. J., and Zoghbi, H. Y. (2001). Requirement of Math1 for secretory cell lineage commitment in the mouse intestine. Science 294, 2155-2158.

Yilmaz, O. H., Katajisto, P., Lamming, D. W., Gultekin, Y., Bauer-Rowe, K. E., Sengupta, S., Birsoy, K., Dursun, A., Yilmaz, V. O., Selig, M., et al. (2012). mTORC1 in the Paneth cell niche couples intestinal stem-cell function to calorie intake. Nature. 486, 490-495.

Ying, Q. L., Wray, J., Nichols, J., Batlle-Morera, L., Doble, B., Woodgett, J., Cohen, P., and Smith, A. (2008). The ground state of embryonic stem cell self-renewal. Nature 453, 519-523.

Yui, S., et al., (2012). Functional engraftment of colon epithelium expanded in vitro from a single adult Lgr5+ stem cell. Nature Medicine 18(4): p. 618-623.

Yao M, Taylor R A, Richards M G, Sved P, Wong J, Eisinger D, Xie C, Salomon R, Risbridger G P, Dong Q. (2010) Prostate-regenerating capacity of cultured human adult prostate epithelial cells. Cells Tissues Organs. 191(3): 203-12.

Yu, P. B., Hong, C. C., Sachidanandan, C., Babitt, J. L., Deng, D. Y., Hoyng, S. A., Lin, H. Y., Bloch, K. D., and Peterson, R. T. (2008). Dorsomorphin inhibits BMP signals required for embryogenesis and iron metabolism. Nature chemical biology 4, 33-41.

Zhang, Q., Major, M. B., Takanashi, S., Camp, N. D., Nishiya, N., Peters, E. C., Ginsberg, M. H., Jian, X., Randazzo, P. A., Schultz, P. G., et al. (2007). Small-molecule synergist of the Wnt/beta-catenin signaling pathway. Proc Natl Acad Sci USA 104, 7444-7448.

Zhang, Y., et al. (2000). Coculture of bladder urothelial and smooth muscle cells on small intestinal. J Urol 164(3 Pt 2): p. 928-34; discussion 934-5.

Zhong, H., Zou, H., Semenov, M. V., Moshinsky, D., He, X., Huang, H., Li, S., Quan, J., Yang, Z., and Lin, S. (2009). Characterization and development of novel small-molecules inhibiting GSK3 and activating Wnt signaling. Molecular bioSystems 5, 1356-1360.

Zaharevitz, D. W., Gussio, R., Leost, M., Senderowicz, A. M., Lahusen, T., Kunick, C., Meijer, L., and Sausville, E. A. (1999). Discovery and initial characterization of the paullones, a novel class of small-molecule inhibitors of cyclin-dependent kinases. Cancer Res 59, 2566-2569.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A cell culture solution comprising an inhibitor of a Bone Morphogenic Protein, an agent that binds to the Leucine-rich repeat-containing G-protein coupled receptor 5, a Wnt agonist and a histone deacetylase 6 (HDAC) inhibitor.

2. The cell culture solution of claim 1, wherein the Wnt agonist is selected from the group consisting of: Wnt-1/Int-1, Wnt-2/Irp (Int-I-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, Wnt-16, R-spondin 1, R-spondin 2, R-spondin 3, R-spondin 4, Norrin, CHIR99021, lithium chloride (LiCl), BIO ((2'Z,3'E)-6-Bromoindirubin-3'-oxime), CHIR98014, SB 216763, SB 415286, 3F8, Kenpaullone, 1-Azakenpaullone, TC-G 24, TCS 2002, AR-A 014418, 2-amino-4-[3,4-(methylenedioxy)benzyl-amino]-6-(3-methoxyphenyl)pyrimidine, IQ 1, DCA, QS 11, WAY-316606, (hetero)arylpyrimidines, 10Z-Hymenialdisine, TCS 21311, TWS 119, GSK-3 Inhibitor IX, GSK-3 Inhibitor IV, GSK-3β Inhibitor II, GSK-3β Inhibitor I, GSK-3β Inhibitor XXVII, GSK-3beta Inhibitor XXVI, FRATtide, Cdk1/5 Inhibitor, Bikinin, and 1-Azakenpaullone.

3. The cell culture solution of claim 1, wherein the HDAC6 inhibitor is selected from the group consisting of Tubacin and Tubastatin A and Compound 7.

4. The cell culture solution of claim 1, wherein the inhibitor of a Bone Morphogenic Protein is selected from the group consisting of Noggin, Chordin, Follistatin, differential screening-selected gene aberrative in neuroblastoma (DAN), proteins comprising a DAN cysteine-knot domain, Sclerostin, Twisted Gastrulation, Uterine Sensitivity-Associated Gene-1, Connective-Tissue Growth Factor, Inhibin, BMP-3, and Dorsomorphin.

5. The cell culture solution of claim 1, further comprising an Epidermal Growth Factor.

6. The cell culture solution of claim 1, further comprising a Notch agonist selected from the group consisting of a Notch1 antibody (N1 Ab), Delta 1, Delta-like 3, Delta-like 4, Jagged 1, Jagged 2, delta/serrate/lag2 (DSL) peptide and Delta D.

7. A cell culture system comprising:
an epithelial stem cell or epithelial progenitor cell or a population of epithelial stem cells or epithelial progenitor cells;
R-spondin 1;
CHIR99021;
a histone deacetylase inhibitor; and
optionally an inhibitor of a Bone Morphogenic Protein.

8. The cell culture system of claim 7, wherein the histone deacetylase inhibitor is a Pan-HDAC inhibitor.

9. The cell culture system of claim 8, wherein the Pan-HDAC inhibitor is selected from the group consisting of Valproic acid, Trichostatin A, suberoylanilide hydroxamic acid and suberohydroxamic acid (SBHA).

10. The cell culture system of claim 8, wherein the histone deacetylase inhibitor is an HDAC6 inhibitor.

11. The cell culture system of claim 10, wherein the HDAC6 inhibitor is selected from the group consisting of Tubacin and Tubastatin A.

12. The cell culture system of claim 7, wherein the inhibitor of a Bone Morphogenic Protein is selected from the group consisting of Noggin, Chordin, Follistatin, DAN, proteins comprising a DAN cysteine-knot domain, Sclerostin, Twisted Gastrulation, Uterine Sensitivity-Associated Gene-1, Connective-Tissue Growth Factor, Inhibin, BMP-3, and Dorsomorphin.

13. The cell culture system of claim 7, further comprising an Epidermal Growth Factor.

14. The cell culture system of claim 7, further comprising a Notch agonist selected from the group consisting of a Notch1 antibody (N1 Ab), Delta 1, Delta-like 3, Delta-like 4, Jagged 1, Jagged 2, DSL peptide and Delta D.

15. A cell culture system comprising:
i) an epithelial stem cell or epithelial progenitor cell or a population of epithelial stem cells or epithelial progenitor cells;
R-spondin 1;
CHIR99021;
an atonal bHLH transcription factor 1 (Atoh1) inhibitor; and
optionally an inhibitor of a Bone Morphogenic Protein.

16. The cell culture system of claim 15, wherein the Atohl inhibitor is an inhibitory nucleic acid.

17. The cell culture system of claim 15, wherein the inhibitor of a Bone Morphogenic Protein is selected from the group consisting of Noggin, Chordin, Follistatin, DAN, proteins comprising a DAN cysteine-knot domain, Sclerostin, Twisted Gastrulation, Uterine Sensitivity-Associated Gene-1, Connective-Tissue Growth Factor, Inhibin, BMP-3, and Dorsomorphin.

18. The cell culture system of claim 15, further comprising an Epidermal Growth Factor.

19. The cell culture system of claim 15, further comprising a Notch agonist selected from the group consisting of a Notch1 antibody (N1 Ab), Delta 1, Delta-like 3, Delta-like 4, Jagged 1, Jagged 2, DSL peptide and Delta D.

* * * * *